(12) United States Patent
Sinkkonen et al.

(10) Patent No.: US 11,318,173 B2
(45) Date of Patent: May 3, 2022

(54) PROBIOTIC IMMUNOMODULATORY COMPOSITIONS

(71) Applicant: Uute Scientific Oy, Lohja (FI)

(72) Inventors: Aki Sinkkonen, Lahti (FI); Mira Grönroos, Lahti (FI); Heikki Hyöty, Tampere (FI); Olli-Heikki Laitinen, Tampere (FI); Noora Nurminen, Tampere (FI); Sami Oikarinen, Tampere (FI)

(73) Assignee: Uute Scientific Oy, Lohja (FI)

( * ) Notice: Subject to any disclaimer, the term of this patent is extended or adjusted under 35 U.S.C. 154(b) by 0 days.

(21) Appl. No.: 16/466,405

(22) PCT Filed: Dec. 7, 2017

(86) PCT No.: PCT/FI2017/050868
§ 371 (c)(1),
(2) Date: Jun. 4, 2019

(87) PCT Pub. No.: WO2018/104587
PCT Pub. Date: Jun. 14, 2018

(65) Prior Publication Data
US 2019/0343898 A1 Nov. 14, 2019

(30) Foreign Application Priority Data
Dec. 7, 2016 (FI) .................................. 20165932

(51) Int. Cl.
| | | |
|---|---|---|
| A61K 35/02 | (2015.01) | |
| A61K 35/742 | (2015.01) | |
| A61K 8/96 | (2006.01) | |
| A61K 8/99 | (2017.01) | |
| A61K 9/00 | (2006.01) | |
| A61K 35/10 | (2015.01) | |
| A61K 35/747 | (2015.01) | |
| A61K 35/00 | (2006.01) | |
| A61K 35/12 | (2015.01) | |

(52) U.S. Cl.
CPC ............ *A61K 35/742* (2013.01); *A61K 8/965* (2013.01); *A61K 8/99* (2013.01); *A61K 9/0014* (2013.01); *A61K 35/10* (2013.01); *A61K 35/747* (2013.01); *A61K 2035/115* (2013.01); *A61K 2035/122* (2013.01)

(58) Field of Classification Search
None
See application file for complete search history.

(56) References Cited

U.S. PATENT DOCUMENTS

| 5,826,273 | A | 10/1998 | Eckes |
| 9,457,077 | B2 | 10/2016 | Kovarik et al. |
| 9,511,099 | B2 | 12/2016 | Jones et al. |
| 2015/0037285 | A1 | 2/2015 | Blaser et al. |
| 2016/0113974 | A1 | 4/2016 | Jones et al. |

FOREIGN PATENT DOCUMENTS

| EP | 1372609 B1 | 9/2006 |
| EP | 2292731 A1 | 3/2011 |
| EP | 1538198 B1 | 10/2012 |
| WO | 2009/068474 A1 | 6/2009 |
| WO | 2014/145958 A2 | 9/2014 |
| WO | 2015/095241 A2 | 6/2015 |

OTHER PUBLICATIONS

Sallinen, H., Turve tehostaa aineenvaihduntaa. Keskisuomalainen [online], Mar. 31, 2009, https://www.ksml.fi/tanaan/Turve-tehostaa-aineenvaihduntaa/443955.
Schepetkin, I., et al., "Medical Drugs From Humus Matter: Focus on Mumie," Drug Development Research, 57(3): 140-159 (2002).
Sornplang, P., et al., "Probiotic isolates from unconventional sources: a review", Journal of Animal Science and Technology, vol. 58, (2016).
Hertzen, L. von, et al., "Disconnection of man and the soil: Reason for the asthma and atopy epidemic?", J Allergy Clin Immunol, vol. 117, No. 2: 334-344 (2016).
Alenius, H., et al., "Contrasting Immunological Effects of Two Disparate Dusts—Preliminary Observations," Int Arch Allergy Immunol, 149: 81-90 (2009).
Caporaso, J. G., et al., "Ultra-high-throughput microbial community analysis on the Illumina HiSeq and MiSeq platforms," The ISME Journal, 6: 1621-1624 (2012).
Caporaso, J. G., et al., "QIIME allows analysis of highthroughput community sequencing data," Nature Methods, 7(5) (2010).
Cinek, O., et al., "Imbalance of bacteriome profiles within the Finnish Diabetes Prediction and Prevention study: Parallel use of 16S profiling and virome sequencing in stool samples from children with islet autoimmunity and matched controls," Pediatric Diabetes (2016).
Cole, J. R., et al., "The Ribosomal Database Project: improved alignments and new tools for rRNA analysis," Nucleic Acids Research, 37: D141-D145 (2009).
Desantis, T. Z., et al., Greengenes, a Chimera-Checked 16S rRNA Gene Database and Workbench Compatible with ARB, Applied and Environmental Microbiology, 72(7): 5069-5072 (2006).
Dominguez-Bello, M. G., et al., "Partial restoration of the microbiota of cesarean-born infants via vaginal microbial transfer," Nature Medicine, 22(3): 250-254 (2016).
Edgar, R. C., et al., "UCHIME improves sensitivity and speed of chimera detection," Bioinformatics, 27 (16): 2194-2200 (2011).
Fakruddin, Md., et al., "Viable but Nonculturable Bacteria: Food Safety and Public Health Perspective," ISRN Microbiology (2013).
Veach, A. M., et al., "Woody plant encroachment, and its removal, impact bacterial and fungal communities across stream and terrestrial habitats in a tallgrass prairie ecosystem," FEMS Microbiology Ecology, 91(10) (2015).

(Continued)

*Primary Examiner* — Jennifer E Graser
(74) *Attorney, Agent, or Firm* — Elmore Patent Law Group, P.C.; Joseph C. Zucchero; Carolyn S. Elmore

(57) ABSTRACT

The invention discloses an immunomodulatory composition comprising non-culturable bacteria, a method of production and an article and an apparatus for its use and administration.

13 Claims, 16 Drawing Sheets

Specification includes a Sequence Listing.

(56) References Cited

OTHER PUBLICATIONS

Anderson, M. J., "A new method for non-parametric multivariate analysis of variance," Austral Ecology, 26: 32-46 (2001).
Bakken, J. S., "Fecal bacteriotherapy for recurrent Clostridium difficile infection," Anaerobe, 15: 285-289 (2009).
Berry, D., et al., "Barcoded Primers Used in Multiplex Amplicon Pyrosequencing Bias Amplification," Applied and Environmental Microbiology, 77(21): 7846-7849 (2011).
Fisher, R. A., "Statistical Methods for Research Workers," Ch. 4, Oliver and Boyd (1954).
Fumagalli, M., et al., "Parasites represent a major selective force for interleukin genes and shape the genetic predisposition to autoimmune conditions," The Journal of Experimental Medicine, 206 (6): 1395-1408 (2009).
Gower, J. C., "Some distance properties of latent root and vector methods used in multivariate analysis," Biometrika, 53: 325-338 (1966).
Huang, R., et al., "Effect of Probiotics on Depression: A Systematic Review and Meta-Analysis of Randomized Controlled Trials," Nutrients, 8 (483): 1-12 (2016).
Hughes, J. B., et al., "The Application of Rarefaction Techniques to Molecular Inventories of Microbial Diversity," Methods in Enzymology, 397: 292-308 (2005).
Hutkins, E. W., et al., "Prebiotics: why definitions matter." *Curr Opin Biotechnol.*, 37: 1-7 (2016).
Gibson, Glenn R., et al., "Dietary Modulation of the Human Colonic Microbiota: Introducing the Concept of Prebiotics," J. Nutr., 125: 1401-1412 (1995).
Huse, S. M., et al., "Ironing out the wrinkles in the rare biosphere through improved OTU clustering," Environmental Microbiology, 12(7): 1889-1898 (2010).
Koskinen, K., et al., "Spatially differing bacterial communities in water columns of the Northern Baltic Sea," FEMS Microbiol Ecol, 75: 99-110 (2011).
Kozich, J. J., et al., "Development of a Dual-Index Sequencing Strategy and Curation Pipeline for Analyzing Amplicon Sequence Data on the MiSeq Illumina Sequencing Platform," Applied and Environmental Microbiology, 79(17): 5112-5120 (2013).
Krebs, C. J., "Ecology: the experimental analysis of distribution and abundance." Fifth edition. Benjamin Cummings, San Francisco, California, USA (2001).
Krogvold, L., et al., "Detection of a Low-Grade Enteroviral Infection in the Islets of Langerhans of Living Patients Newly Diagnosed with Type 1 Diabetes," Diabetes, 64(5): 1682-1687 (2015).
Legendre, P., Numerical Ecology. 2nd English edition. Elsevier Science BV, Amsterdam (1998).
Love, M. I., et al., "Moderated estimation of fold change and dispersion for RNA-seq data with DESeq2," Genome Biology, 15: 1-21 (2014).
Magurran, A. E., "Measuring biological diversity," Blackwell Publishing: Oxford, UK. 2004.
Matisz, C. E., et al., "Adoptive transfer of helminth antigen-pulsed dendritic cells protects against the development of experimental colitis in mice," Eur. J. Immunol., 45: 3126-3139 (2015).
McFarland, L. V., et al., "Systematic review and meta-analysis: Multi-strain probiotics as adjunct therapy for Helicobacter pylori eradication and prevention of adverse events," United European Gastroenterology Journal, 4(4): 546-561 (2016).
McMurdie, P. J., et al., "phyloseq: An R Package for Reproducible Interactive Analysis and Graphics of Microbiome Census Data," PloS One, 8(4): e61217 (2013).
Muhleisen, A. L., et al., "Menopause and the vaginal microbiome," Maturitas, 91: 42-50 (2016).
Öqvist, C. K., et al., "Prokaryotic microbiota of recycled paper mills with low or zero effluent," J Ind Microbiol Biotechnol, 35: 1165-1173 (2008).
Petrof, E. O., "Stool substitute transplant therapy for the eradication of Clostridium difficile infection: 'RePOOPulating'the gut," Microbiome, 1: 1-12 (2013).
Pruesse, E., et al., "SILVA: a comprehensive online resource for quality checked and aligned ribosomal RNA sequence data compatible with ARB," Nucleic Acids Research, 35(21): 7188-7196 (2007).
Rossi, O., et al., "Faecalibacterium prausnitzii A2-165 has a high capacity to induce IL-10 in human and murine dendritic cells and modulates T cell responses," Scientific Reports, 6: 1-12 (2015).
Schloss, P. D., "Microbiology: An integrated view of the skin microbiome," Nature, 514: 44-45 (2014).
Schloss, P. D., et al., "Introducing mothur: Open-Source, Platform-Independent, Community-Supported Software for Describing and Comparing Microbial Communities," Applied and Environmental Microbiology, 75(23): 7537-7541 (2009).
Schloss, P. D., et al., Reducing the Effects of PCR Amplification and Sequencing Artifacts on 16S rRNA-Based Studies, PLoS ONE, 6(12): e27310 (2011).
Schmidt, T. S. B., et al., "Ecological Consistency of SSU rRNA-Based Operational Taxonomic Units at a Global Scale," PLoS Comput Biol 10(4): e1003594 (2014).
Schnorr, S. L., et al., "Gut microbiome of the Hadza hunter-gatherers," Nature Communications, 5: 1-12 (2014).
Schnorr, S. L., et al., "Gut microbiome of the Hadza hunter-gatherers," Supplemental Information.
Schuijs, M. J., et al., "The Helminth-Derived Immunomodulator AvCystatin Reduces Virus Enhanced Inflammation by Induction of Regulatory IL-10$^+$ T Cells," PLOS ONE, pp. 1-14 (2016).
Shannon, C. E., "A Mathematical Theory of Communication," The Bell System Technical Journal, vol. 27: 379-423, 623-656 (1948).
Sokol, H., et al., "Faecalibacterium prausnitzii is an anti-inflammatory commensal bacterium identified by gut microbiota analysis of Crohn disease patients," PNAS, 105(43): 16731-16736 (2008).
Stein, M. M., et al., "Innate Immunity and Asthma Risk in Amish and Hutterite Farm Children," The New England Journal of Medicine, 375(5): 411-421 (2016).
Stewart, E. J., "Growing Unculturable Bacteria," Journal of Bacteriology, 194(16): 4151-4160 (2012).
Sung, H., et al., "Microbiota-based treatments in alcoholic liver disease," World J Gastroenterol, 22(29): 6673-6682 (2016).
Taylor, L. H., et al., "Risk factors for human disease emergence," Phil. Trans. R. Soc. Lond. B, 356: 983-989 (2001).
Wang, Q., et al., "Naïve Bayesian Classifier for Rapid Assignment of rRNA Sequences into the New Bacterial Taxonomy," Applied and Environmental Microbiology, 73(16): 5261-5267 (2007).
Yatsunenko, T., et al., "Human gut microbiome viewed across age and geography," Nature, 486: 222-228 (2012).
Office Action dated Oct. 21, 2020 for Patent Application No. 20165932, received from the Finnish Patent and Registration Office.
Fyhrquist, N. et al., "*Acinetobacter* species in the skin microbiota protect against allergic sensitization and inflammation", J. Allergy Clin. Immunol., vol. 134, No. 6, 2014, 1301-1309.
Hoeksema, M. et al., "Treatment with Trichuris suis soluble products during monocyte-to-macrophage differentiation reduces inflammatory responses through epigenetic remodeling", The FASEB Journal, vol. 30, 2016, 2827-2836.
Pershina, E. et al., "Comparative Analysis of Prokaryotic Communities Associated with Organic and Conventional Farming Systems", PLoS ONE 10(12): e0145072. doi:10.1371/journal.pone.0145072.
Shannon, D. et al., "A comparative study of the microbiology of soils managed under organic and conventional regimes", Soil Use and Management, vol. 18, 2002, 274-283.
Volz, T. et al., "Nonpathogenic Bacteria Alleviating Atopic Dermatitis Inflammation Induce IL-10-Producing Dendritic Cells and Regulatory Tr1 Cells", Journal of Investigative Dermatology, vol. 134, 2013, 96-104.

PROBIOTIC IMMUNOMODULATORY COMPOSITIONS

FIELD

The present disclosure is related to the field of immunomodulatory compositions. In more detail, it relates to compositions obtainable by processing material derived from nature, to methods for their manufacturing and to their use.

BACKGROUND

Previously, immune system has been treated using cultivated probiotics that are either single bacterial strains or combinations of rare cultivated strains. The beneficial effects of these products cover reduced probability of diarrhea and other gastrointestinal symptoms. Their use has been also studied in the prevention of otitis media and in the treatment of alcoholic liver diseases (Sung et al. 2016), eradication of helicobacteria (McFarland et al. 2016), treatment of depression (Huang et al. 2016), maintenance of healthy vaginal microbiome during menopause (Muhleisen and Herbst-Kralovetz 2016) and in the context of many other immune health related problems. Probiotics are also recommended for pregnant women and for infants, as there is evidence that they reduce the probability of the upcoming child to develop atopy. Probiotic-related treatments are also on the market, such as Dirt shampoo where the active component is said to be a single, cultivated *Mycobacterium* species that has reduced mental disorders in rodents. Also parasitic worms and helminths have been experimented in immunotherapy (Fumagalli et al. 2009; Schuijs et al. 2016; Matisz et al. 2015).

In addition to probiotics, human vaginal fluids and human stool have been used to transfer microflora from human to human (Dominguez-Bello et al. 2016, Bakken 2009). The health effects of maternal vaginal fluids on infants born in cesarean section are unclear, and stool transfer i.e. fecal bacteriotherapy is known to cure *Clostridium difficile* infection (Bakken 2009). Due to potential pathogen transfer, the donor of vaginal fluids is always infant's own mother. As there are concerns of pathogen transmission, a synthetic mixture of cultivated strains has been proposed to avoid pathogenic microbes (Petrof et al. 2013). Fecal transplantation has been proven effective for only few diseases and not for diseases that are treated by modulating immune system.

Another, more traditional branch of treating immune system is the use of chemicals, like immunosuppressive drugs. Prebiotics that modify the activity of existing human microflora are available (Hutkins et al. 2016, Schloss 2014). The reason for the desired effect of prebiotics is in chemical compounds, such as dietary fibers, not in the microbiological content of prebiotics (Gibson, Roberfroid 1995). Natural allergens are also used to treat allergies, e.g. birch pollen is used to treat pollinosis. The combination of several animal and hey allergens is also marketed to prevent allergy. There are also speculative chemical-based treatments that are said to prevent or even cure allergies or immune system disorders.

The currently available treatments of immune system disorders and immune related diseases cover the use of chemicals (drugs, prebiotics and purified allergens). In addition, cultivated microbial strains and human excretions have been used for this purpose, but there is only limited evidence of their efficacy and their long-term use required for prophylaxis is not convenient for the subjects.

SUMMARY

In natural terrestrial environments and healthy human gut, a significant proportion—typically 40-99%—of bacteria are non-culturable. This results in enormous microbial diversity that is not properly utilized in known products targeting immune system. The reasons are that non-culturable microbial communities are spatially and temporally heterogeneous, they are not easily enriched, and that they often contain pathogenic species. In the current invention, the high microbial diversity is utilized in immunomodulatory compositions that lack the spatial and temporal heterogeneity of natural environments and contain only a limited amount of or no potentially pathogenic species.

In contrast to previous attempts to provide immunomodulatory compositions or microbiome transplantations comprising only a single or very few species of culturable bacteria, fecal or vaginal microbes, the present invention uses natural, safe, and microbiologically very rich material. An advantage of the present invention is that a beneficial change in the gut microbiome can be seen when using the present immunomodulatory composition. No such an effect has been obtained before when orally administered probiotic bacteria were used.

According to the first aspect is provided an immunomodulatory composition comprising a microbial community comprising non-culturable bacteria, wherein
  i. the microbial diversity of the immunomodulatory composition is at least 3 at Shannon diversity index;
  ii. the microbial richness of the immunomodulatory composition is at least 130 operational taxonomic units; and/or
  iii. the microbial abundance of the immunomodulatory composition is at least 1000000 bacterial 16S copies g-1 ww; and/or
  the abundance of pathogens in the immunomodulatory composition is not higher than found in everyday living environment.

In an embodiment of the first aspect the immunomodulatory composition comprises material obtainable by processing material derived from nature, wherein
  a. material derived from nature comprises a microbial community comprising non-culturable bacteria;
  b. the microbial diversity of material derived from nature is at least 3 at Shannon diversity index;
  c. the immunomodulatory composition comprises a microbial community comprising non-culturable bacteria; wherein
    i. the microbial diversity of the immunomodulatory composition is at least 3 at Shannon diversity index;
    ii. the microbial richness of the immunomodulatory composition is at least 130 operational taxonomic units; and/or
    iii. the microbial abundance of the immunomodulatory composition is at least 1000000 bacterial 16S copies g-1 ww; and
  d. the abundance of pathogens in the immunomodulatory composition is not higher than found in everyday living environment.

The inventors surprisingly found that the immunomodulatory composition can be used to modulate microbial diversity, increase microbial diversity, microbial abundance and microbial richness of a subject living in a modern society, preferably in urban conditions. The exposure is safe because pathogen levels can be controlled in the composition. This facilitates to reach similar or near similar microbial abundance (Example 1), diversity (Example 2) and richness (Example 1) as observed for subjects that have remarkably low abundance of autoimmune diseases and other immune system disorders, like allergies. Examples of these low-risk subjects cover traditional hunter-gatherers (Schnorr et al. 2014), children living on traditional dairy farms (Stein et al. 2016) and people living in societies where hygiene standards are not the same as in present-day Western societies (Yatsunenko et al. 2012). Without being bound to any theory, living in modern urban environment causes changes in the natural microbiome of the subject and home dust (Alenius et al. 2009), which may lead to disorders of the immune system or weaken its efficiency. When the subject is exposed to the immunomodulatory composition, the microbial diversity, abundance and richness or at least one of these factors is shifted closer to that observed among low-risk subjects, and therefore the immunomodulatory composition prevents or remedies the immune system related disorders and sicknesses, or improves the efficiency of the immune system. As evidenced by the examples, the present immunomodulatory composition causes increase in microbial abundance, richness, diversity and provides beneficial changes in the IL10-mediated immunoregulatory response (Example 3). An advantage obtainable with the immunomodulatory composition is that subjects receiving the immunomodulatory composition avoid risks of infection and other problems encountered by pathogens and pests. This is a striking difference with traditional hunter-gatherers and many nomads who also receive a rich microbial exposure but who suffer from pathogens and pests.

The processing, which is carried out to obtain the immunomodulatory composition, is preferably such that the resulting composition retains sufficiently non-culturable bacteria or at least their active components that are present in the material derived from nature, and that are able to produce an immunomodulatory effect.

It has been shown that beneficial microbial changes can induce IL-10 mediated immunoregulatory response for example in Crohn disease (Sokol et al. 2008; Rossi et al 2016). The immunomodulatory composition of the first aspect is able to induce a robust immunoregulatory IL-10 response in white blood cells, whereas the proinflammatory IFN-gamma response remains much weaker (Example 3). TGF-β is another cytokine with immunoregulatory characteristics. A suitable dosage of the immunomodulatory composition can be selected to induce immunoregulatory response without inducing inflammation. Both intact (living) and inactivated composition are able to induce a beneficial immunoregulatory response in white blood cells.

The immunomodulatory composition of the first aspect is fundamentally different from existing immunomodulatory compositions at least for two reasons: it comprises non-culturable microbial community that originates in a diverse environment, and its level of pathogens is controlled. In an embodiment the level of pathogens is controlled to a level not higher than found in everyday living environment.

According to an aspect is provide a topical composition comprising the immunomodulatory composition of the first aspect.

According to the second aspect is provided an immunomodulatory composition for use in regulating, maintaining and/or strengthening immune system and immunological regulation of a subject, the use comprising exposing the subject to the immunomodulatory composition according to the first aspect. In an embodiment such a use is a non-medical use.

According to another aspect is provided an immunomodulatory composition for medical use in regulating, maintaining and/or strengthening immune system and immunological regulation of a subject, the use comprising exposing the subject to the immunomodulatory composition according to the first aspect.

According to another aspect is provided an immunomodulatory composition for use in immunological regulation of a subject, the use comprising exposing the subject to the immunomodulatory composition according to the first aspect. In an embodiment such a use is a non-medical use.

According to another aspect is provided an immunomodulatory composition for medical use in immunological regulation of a subject, the use comprising exposing the subject to the immunomodulatory composition according to the first aspect.

In another aspect is provided an immunomodulatory composition for use in maintaining and strengthening immune system of a subject, the use comprising exposing the subject to the immunomodulatory composition according to the first aspect. In an embodiment such a use is a non-medical use.

In another aspect is provided an immunomodulatory composition for medical use in maintaining and strengthening immune system of a subject, the use comprising exposing the subject to the immunomodulatory composition according to the first aspect.

In another aspect is provided immunomodulatory composition of the preceding aspects is for medical treatment of allergy. In an embodiment the immunomodulatory composition is an IL-10 or TGF-β mediated immunomodulatory composition.

According to another aspect is provided an immunomodulatory composition comprising material derived from nature which contains non-culturable microbial community. In an embodiment the material comprises at least one of industrial, mining, agricultural, silvicultural, aquacultural, water purification, water filtration or peat production materials, including byproducts that are currently being used for other purposes without knowing, understanding an utilizing the immunomodulatory properties of the materials. The authors surprisingly found that these existing materials may be suitable for immunomodulatory compositions, provided that pathogen levels are controlled.

In another aspect is provided the immunomodulatory composition for non-medical regulating, maintaining and strengthening of immune system, wherein the subject is a human subject having a disorder of immunity or a human subject living in an urban environment wherein microbial diversity, richness and/or abundance is lower than in the material derived from nature.

According to the third aspect is provided a method for manufacturing an immunomodulatory composition according to the first aspect, the method comprising:

a. Providing material derived from nature to provide raw material;

b. Grinding raw material to obtain particulate or powdered material;

c. Homogenizing spatial variation of microbial community of the powdered material preferably by sieving and mixing;

d. Optionally drying material obtained in b-c to provide dried material wherein the number of living or metabolically active cells of pathogenic species or microbial metabolism decreases;
e. Optionally adding water, oil, carrier or solvent to material obtained in b-d to provide lotion, gel, cream or liquefied material; and
f. Optionally sterilizing material provided in b-d to provide sterilized material.

According to a fourth aspect is provided a method for manufacturing an immunomodulatory composition according to the first aspect, the method comprising
a. Providing material derived from nature to provide raw material;
b. Extracting the raw material to provide an extract;
c. Optionally evaporating the extract to provide gaseous material; and
d. Optionally condensing the evaporated extract.
e. Optionally sterilizing material provided in b-d to provide sterilized material.

According to a fifth aspect is provided a method for manufacturing the immunomodulatory composition of the first aspect, the method comprising:
a. Providing material derived from nature to provide raw material
b. Grinding the raw material to obtain particulate raw material;
c. Sieving the particulate raw material to provide sieved raw material;
d. Extracting the product obtained in step b., or c., to provide an extract;
e. Optionally lyophilizing the extract; and
f. Optionally sterilizing material provided in d or to provide sterilized material.

According to another aspect is provided a method for manufacturing an immunomodulatory composition according to the first aspect comprising material derived from nature, the method comprising:
a. Providing material derived from nature to provide raw material;
b. Optionally grinding raw material to obtain particulate or powdered material;
c. Optionally sieving material derived from nature or the particulate or powdered material to provide sieved material;
d. Optionally oven-drying raw material or material obtained in b-c to provide oven-dried material wherein the microbial community composition or its metabolism changes in oven-drying;
e. Optionally moisturizing raw material or material obtained in b-d to provide lotion-like or liquefied material;
f. Optionally lyophilizing raw material or material provided in b-e to provide lyophilized material;
g. Optionally sterilizing raw material or material provided in b-f to provide sterilized material;
h. Optionally evaporating material derived from nature or material provided in b-g to provide evaporated material; wherein
the method comprises at least step a and any combination of steps b-h performed successively.

According to another aspect is provided a method for manufacturing an immunomodulatory composition according to the first aspect comprising
a. Providing material derived from nature to provide raw material;
b. Optionally grinding the raw material to obtain particulate or powdered material;
c. Optionally sieving the particulate or powdered raw material to provide sieved material;
d. Optionally oven-drying the raw material to provide oven-dried material;
e. Optionally moisturizing the raw material to provide lotion-like or liquefied material;
f. Optionally lyophilizing the raw material to provide lyophilized material;
g. Optionally sterilizing the raw material to provide sterilized material;
h. Optionally evaporating the raw material to provide evaporated material;
i. Extracting the product obtained in step a., b., c., d., e., f., or g. to provide an extract;
j. Optionally lyophilizing the extract to provide the lyophilized extract;
k. Optionally oven-drying the extract to provide oven-dried extract;
l. Optionally evaporating the extract to provide gaseous material;
m. condensing the evaporated extract obtained in step l. to provide condensed material;
n. composting the raw material to provide composted material; and
wherein the method comprises at least step a. and any combination of steps b., c., d., e., f., g., h., i., j., k., l., m., and n.

According to the fifth aspect is provided an article for releasing the immunomodulatory composition of the first aspect comprising a compartment for the composition.

According to the sixth aspect is provided an apparatus for administering immunomodulatory composition of the first aspect, wherein the apparatus is configured to receive a replaceable unit dose of the immunomodulatory composition of the first aspect.

SEQUENCE LISTINGS

Figure 1:
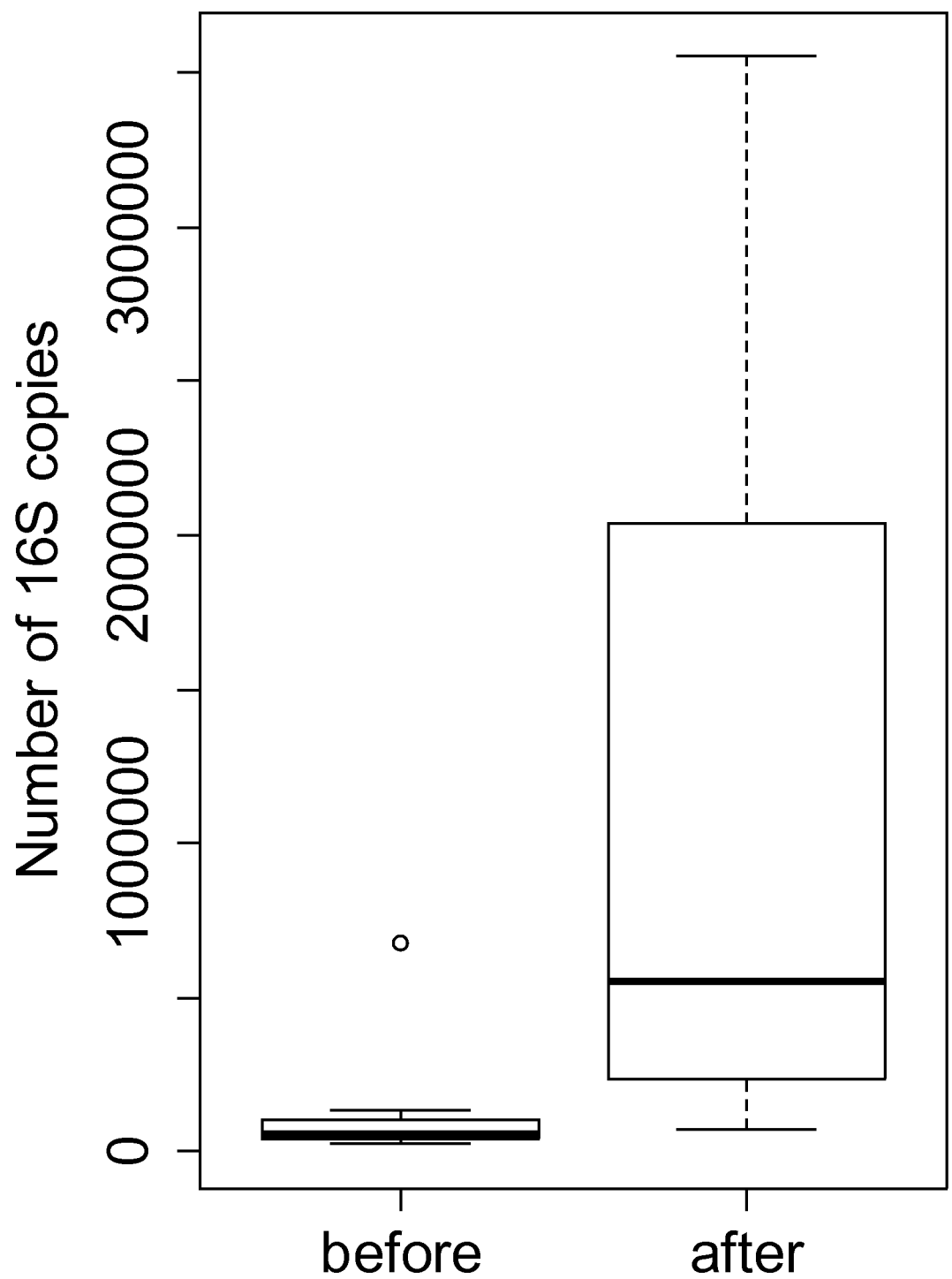
FIG. 1 discloses a box-plot showing the abundance as the number of bacterial 16S copies in hands before and after an exposure to different immunomodulatory compositions comprising non-culturable microbial community. The compositions are different composted and sieved agricultural byproducts and other sieved materials derived from nature. Thick line is the median, the boxes show the lower and upper hinges and whiskers show the most extreme data points. If the most extreme data point is at least 1.5 times the interquartile range of the box, it is shown as a circle. As FIG. 1 shows, the immunomodulatory composition of the first aspect comprising non-culturable microbial community increases microbial abundance on human skin.

SEQ ID NO 1: oligonucleotide pE
SEQ ID NO 2: oligonucleotide pF
SEQ ID NO 3: oligonucleotide 505F
SEQ ID NO 4: oligonucleotide 806R
SEQ ID NO 5: oligonucleotide pA_Illumin_FP
SEQ ID NO 6: oligonucleotide pD'_Illumin_RP
SEQ ID NO 7: oligonucleotide pA 1: AGAGTTTGATCMTGGCTCAG
SEQ ID NO 8: oligonucleotide pA 2: TAGAGAGTTTGATCMTGGCTCAG
SEQ ID NO 9: oligonucleotide pA 3: CTCTAGAGTTTGATCMTGGCTCAG
SEQ ID NO 10: oligonucleotide pD' 1: GTATTACCGCGGCTGCTG
SEQ ID NO 11: oligonucleotide pD' 2: CGTATTACCGCGGCTGCTG
SEQ ID NO 12: oligonucleotide pD' 3: TAGTATTACCGCGGCTGCTG
SEQ ID NO 13: oligonucleotide pD' 2: ATCTACACTCTTTCCCTACACGACGCTCTTCCGATCT
SEQ ID NO 14: oligonucleotide pD' 3: GTGACTGGAGTTCAGACGTGTGCTCTTCCGATCT

DETAILED DESCRIPTION

The present invention is based on the new finding that immunomodulatory composition based on the material derived from nature can be used to prevent or cure immune system associated disorders and diseases or to enhance the efficacy or to maintain the health of the immune system.

Methods to Determine Threshold Values

The parameters characterizing the present invention were determined as explained below. As is understood in the art, the skilled person may in special situation select an alternative or supplementary method for determining a parameter. Depending on the selected assay conditions, subsampling protocol, sampling depth, extraction method or Illumina kit or any other technical detail of the molecular biological or computational analysis may therefore provide different parameters compared to what is obtained in the characterizing parameters of the current invention. A change in a detail of the analysis may affect a threshold value. The examples below provide alternative protocols of determining threshold values. However, the parameters used in claims can be determined by the skilled person by following the teaching below.

Sample Preparation for MiSeq Sequencing

Samples are stored in deep freezer (<−70° C.) before DNA extraction. Material wet weight used in DNA extraction is 0.25 g. Total DNA is extracted from samples using PowerSoil® DNA Isolation Kit (MoBio Laboratories, Inc., Carlsbad, Calif., USA) according to the manufacturer's standard protocol and DNA is checked with agarose gel (1.5%) electrophoresis (120 V, 30 min). The total DNA concentration is measured with Quant-iT™ PicoGreen® dsDNA reagent kit (Thermo scientific, MA, USA). The DNA concentration is adjusted to 0.35-0.4 ng/µl in each sample. DNA is analyzed for bacterial (16S) communities using a two-step PCR approach to avoid a 3'-end amplification bias resulting from the sample-specific DNA tags (Berry et al. 2011). The V4 region within the 16S ribosomal RNA (rRNA) gene is amplified by primary PCR using 505F and 806R primers (Caporaso et al. 2012). Primary PCR is carried out in a reaction mixture (reaction volume 50 µl) consisting of 1 µl each of 10 mM deoxynucleoside triphosphates (dNTPs; Thermo scientific, MA, USA) 5 µl forward primer 505F (10 µM; 5'-GTGCCAGCMGCCGCGGTAA-3') and 5 µl reverse primer 806R (10 µM; 5'-GGACTACHVGGGTWTCTAAT-3'), 0.5 µl 2 U/µl Phusion Green Hot Start II High-Fidelity DNA polymerase (Thermo scientific, MA, USA), 10 µl 5× Green HF PCR buffer (F-537), 5 µl template DNA and 23.5 µl sterile water. The PCR reaction is run in a thermocycler as follows: initial denaturation at 98° C. for 5 min, followed by 25 cycles with denaturation at 94° C. for 1 min, annealing for 10 sec at 50° C. and extension for 1 min at 72° C., and then a final extension at 72° C. for 10 min. A negative control (sterile water) is used to detect and later adjust data for any possible contamination. DNA was detected with agarose gel (1.5%) electrophoresis (120 V, 1 h). The PCR products are purified using Agencourt AMPure XP solution (Beckman Coulter Ins.) to reduce carryover of primary PCR primers. The cleaned amplicons are diluted 1:5.

Cleaned and diluted primary PCR products are targeted in the secondary PCR (TagPCR). Reaction mixture to the TagPCR is equal as above except reverse primer include a 12 bp unique Multiplexing Identifier tag (MID-806R). Amplification program is the same as above except that only ten cycles are used. TagPCR products are detected on agarose gel (1.5%) electrophoresis (120 V, 1 h), purified with Agencourt AMPure, pooled and the DNA concentration is measured with PicoGreen. The sequencing is performed using Illumina MiSeq platform with a 2×300 bp version 3 kit sequencing kit according to manufacturer's protocol. The GeneRead DNA Library I Core Kit (Qiagen, catalog #180432) is used to ligate Illumina's TruSeq adapters to amplicons.

Sequence Processing

The paired sequences contained in reverse and forward fastq files are aligned into a contig. The resulted library is trimmed and screened to remove any mismatches with primer or DNA-tag sequences, ambiguous bases and homopolymers larger than 8 bp long. Sequences are aligned using Mothur version of SILVA bacterial reference sequences (version 102; Pruesse et al. 2007) and the sequences, which are not aligned to a reference alignment of the correct sequencing region are removed. Unique sequences and their frequency in each sample are identified, and then, almost identical sequences (>99% similar) are preclustered to minimize sequencing errors (Huse et al. 2010) and screened for chimeras (UCHIME, Edgar et al. 2011) using the abundant sequences as a reference. The chimeric sequences are removed. The sequences are classified using Mothur version of Bayesian classifier (Wang et al. 2007) with the RDP training set version 9 (Cole et al 2009). Sequences that are classified as Mitochondria, Chloroplast, Archaea, Eukaryota or unknown are removed. Operational taxonomic units (OTUs) are assigned at 97% identity. Rare OTUs that are represented with 10 or fewer sequences in the whole data are removed. For each OTU the number of sequences detected in control is subtracted from the samples and negative values are changed to zeros. Finally, all the samples are rarefied to 2000 sequences. If the sample includes less than 2000 sequences, it is not considered further.

qPCR Method

Quantitative PCRs are carried out with the Light Cycler 96 Quantitative real-time PCR machine (MJ Research, MA, USA). The forward primer is pE 5"-AAA CTC AAA GGA ATT GAC GG-3' (SEQ ID NO:1) and the reverse primer pF 5'-ACG AGC TGA CGA CAG CCA TG-3' (SEQ ID NO: 2) (Öqvist et al. 2008). All samples are run in triplicates in 20 µl reactions containing 10 µl 2× PowerUp SYBR Green Master Mix (Thermo scientific, MA, USA), 0.2 µl 20 mg/ml BSA, 0.5 µl of each primer (10 µM), and the sample template. A standard curve is included in every run to allow quantitation of the number of bacterial 16S copies present in the original sample. The q-PCR run is as follows: initial denaturation at 95° C. for 2 min, followed by 40 cycles of denaturation at 95° C. for 10 s, annealing for 20 sec at 53° C. and extension for 30 s at 72° C.

Terminology

As used herein, the term "comprising" includes the broader open meanings of "including", "containing", and "comprehending", as well as the narrower closed meanings of the expressions "consisting of" and "consisting only of".

The term immunomodulatory is multifaceted in the context of this application and it includes at least the following aspects: In one aspect it refers to the stimulation of the immune response to the foreign and harmful materials such as pathogens. It also refers to the overall enhancement of the health, function and potency of the immune system. It also refers to the training of the immune system to response appropriate and healthy ways for different stimuluses and to avoid unhealthy pathological responses. It also covers immunoregulatory and immunostimulatory aspects to tune the immune response in a healthy way and to avoid unhealthy responses. In one aspect it also refers to the maintaining of the healthy status of immune system and immune response or to slowing down the decline of the immune system and immune response for example in the cases of immune system affecting diseases and aging.

The term material derived from nature refers to soil material, plant material, algal, fungal or Protozoan material or non-human animal material, which comprises non-culturable bacteria, and wherein the amount of pathogenic bacteria and viruses drop during processing below or to the level that the subjects are exposed to in their everyday life. Alternatively, the level of pathogenic bacteria and viruses are continuously below or at the level that the subjects are exposed to in their everyday life.

The abundance of pathogens found in everyday living environment may vary. Example 7 provide example of abundances found in exemplary everyday living environments.

The term material derived from nature refers to any natural raw material or byproduct that comprises at least 40 different OTUs at at least 97% similarity level.

In an embodiment the microbial diversity of the immunomodulatory composition is at least 3 at Shannon diversity index at at least 97% similarity level; the microbial richness of the immunomodulatory composition is at least 130 operational taxonomic units at at least 97% similarity level; and/or the microbial abundance of the immunomodulatory composition is at least 1000000 bacterial 16S copies g-1 ww. In another embodiment the level of pathogens in the immunomodulatory composition is not higher or not significantly higher than found in everyday living environment.

In an embodiment the material derived from nature comprises agricultural material streams, such as agricultural plant waste or solid plant waste, milling waste, oil extraction waste, roots, peels, seeds, seed pods, leaves, litter, inflorescence, cones or membranes, or animal byproducts such as animal dung, sludge, internal organs, skin, eggshells, shells or carcasses or their parts.

In an embodiment the material derived from nature comprises silvicultural material streams, such as bark, saw dust, wood chip, shaved wood chip, pulp, needles, leaves, branches, roots, tree litter and other products and byproducts that contain microbial community comprising non-culturable bacteria;

In an embodiment the material derived from nature comprises aquacultural material streams, including byproducts, such as cultivated aquatic animals and their carcasses or body parts, algae, aquatic plants, plankton and debris from the organisms mentioned herein that contain microbial community comprising non-culturable bacteria;

In an embodiment the material derived from nature comprises water purification streams, including byproducts, such as material comprising non-culturable bacteria originating in water filtration systems.

In an embodiment the material derived from nature comprises material streams in production and mining industry, including byproducts, such as peat, plant debris, moss and microbial communities flourishing unintentionally during biomining.

In an embodiment the material derived from nature comprises a selected combination of composted and sieved soil and plant-based ingredients including 861 OTUs (≥97% similarity) from 19 phyla based on 16S rRNA sequencing. In an embodiment the two most abundant phyla are Bacteroidetes and Proteobacteria.

In an embodiment the material derived from nature does not comprise peat.

In another embodiment the material derived from nature does not comprise animal dung or human stool. Such an embodiment is advantageous because of easier control of pathogens and lower initial level of fast growing bacteria in the material.

The term material derived from nature also refers to industrial products that exist, comprise community in claim 1a, comprise at least 40 different OTUs at at least 97% similarity level and are produced and used only for other purposes outside this patent, regardless of their microbiological properties.

The term operational taxonomic unit (shortened as OTU) refers to clusters of 16S or 18S small subunit rRNA gene similarity and it is used as an approximation of microbial taxa (Schmidt et al. 2014). In the claims of the current patent application, we specifically define that the term OTU is determined using variable region 4 (i.e. V4) in bacterial 16S rRNA gene and 97% similarity. OTUs are clustered using nearest neighbor algorithm in Mothur where each of the sequences within an OTU are at most 3% distant from the most similar sequence in the OTU. (https://mothur.org/wiki/Cluster, accessed 5 Dec. 2016) This facilitates comparison of the claims presented herein to any other potential applications in the future. It should be noted that when analyzing the effect of the immunomodulatory composition, OTUs can be defined using other variable regions, such as variable regions 1-3 that were used in example 1.

The term non-culturable bacteria refers to bacteria that are viable and metabolically or physiologically active, but not culturable. The bacterial cells that form a colony on specific nutrient media are defined as culturable bacteria. So the bacteria that are metabolically or physiologically active but cannot be cultured on specific media are the viable but non-culturable bacteria (Fakruddin et al., 2013). Regarding this by using modern molecular recognition tools such as 16S rRNA sequencing the number of divisions of bacteria has grown from 11 to at least 85 after year 1989, and the majority of these divisions have no cultured representatives (Stewart, 2012).

The term abundance refers to the total number of 16S or 18S gene copies per g wet weight.

The term wet weight (shortened as ww) refers to sample weight wherein water is included. In an embodiment water content of a wet weight sample is 0.1-80%, such as 50%.

Terms subsampling rarefying and rarefaction (Hughes and Hellmann 2005) refer to a procedure where samples are scaled down to an equal number of sequences by randomly picking the same number of sequences from each sample.

The terms Shannon diversity index or Shannon index (Shannon, 1948) refer to a commonly used measure of diversity, which measures the uncertainty to correctly predict the taxa of the next individual collected (Krebs 2001). The index value increases when (1) the number of taxa increases and (2) the more evenly the abundances of sequences are distributed among taxa. The index can be calculated using different logarithmic bases but here the index is calculated using natural logarithm and thus the equation is as follows:

$$H = -\sum_{i=1}^{s} p_i \ln p_i$$

where $p_i$ is the proportional abundance of a taxon i.

The term richness refers to the number of OTUs in a sample. Preferably, richness refers to OTU similarity of 97%. Richness can also refer to the number of taxa (e.g. genera, classes, phyla) in a sample.

In an embodiment the immunomodulatory composition contains a diversity of metabolically almost inactive microbes that are rare in urban space and usually abundant in natural environments. Without being bound to any theory, they induce an immunoregulatory response in a subject exposed to them.

The term sterilizing or inactivation refers to irradiating, autoclaving, boiling, steaming and other methods suitable for inactivating or killing living microbes and pathogens or destroying their outer membranes.

In another embodiment the immunomodulatory composition comprises aqueous extract obtained by extracting material derived from nature by an aqueous solvent.

Pathogens

In an embodiment the material derived from nature is essentially free from pathogens.

In an embodiment the immunomodulatory composition is free from pathogens.

In an embodiment the level of pathogens in the immunomodulatory composition is below a level of 50 sequences per 0.25 g ww sample in bacterial genera that were classified as potentially pathogenic by Taylor et al. (2001). These comprise of the following genera: *Acinetobacter, Actinomyces, Aerococcus, Aeromonas, Arcobacter, Bacillus, Bacteroides, Bifidobacterium, Brevibacillus, Brevundimonas, Chryseobacterium, Corynebacterium, Fibrobacter, Finegoldia, Gemella, Lactobacillus, Legionella, Leptotrichia, Moraxella, Mycobacterium, Myroides, Neisseria, Nocardia, Paenibacillus, Prevotella, Pseudomonas, Pseudonocardia, Psychrobacter, Rhodococcus, Rickettsia, Saccharomonospora, Sphingomonas, Stenotrophomonas, Streptococcus,* and *Treponema*. As evidenced by example 7, the total number of sequences in all the potentially pathogenic bacterial genera listed by Taylor et al. (2001) is lower in the immunomodulatory composition than what is found in everyday living environment of urban children (sandpits on daycare yards). In an embodiment the pathogen refers to a strain of above genera having pathogenic characteristics.

In an embodiment the level of pathogens in the immunomodulatory composition is below a level of 100, 200, 300, 400 or 500 sequences per 0.25 g ww sample in bacterial genera that were classified as potentially pathogenic by Taylor et al. (2001).

In an embodiment the sample is subsampled.

In an embodiment, the level of certain pathogens is determined using cultivation in laboratory conditions. As evidenced by example 6, the manufacturing methods of the immunomodulatory composition guarantee that it lacks pathogenic *Pseudomonas aeruginosa*. In yet another embodiment of the first aspect the abundance of *Escherichia coli* and *Pseudomonas auriginosa* in the immunomodulatory composition is 0, as evidenced in examples 6 and 7.

In an embodiment, the level of pathogens is determined using a Q-PCR based method. As evidenced by example 5, the manufacturing methods of the immunomodulatory composition guarantee that it lacks the following viral and protozoan pathogens: enterovirus, rhinovirus, rotavirus, norovirus, *Giardia* and *Cryptosporidium*.

In an embodiment, the level of pathogens can be determined using e.g. Illumina sequencing of bacterial community. As evidenced by example 7, the manufacturing methods of the immunomodulatory composition guarantee that it lacks the following bacterial pathogenic genera: *Bacillus, Escherichia, Neisseria* and *Nocardia*.

Taxa

In an embodiment non-culturable bacteria that are present in the immunomodulatory composition are selected from the phyla Actinobacteria, Acidobacteria, Bacteroidetes, Firmicutes, Proteobacteria, or a combination thereof. Within Proteobacteria, the selection can be made from Alphaproteobacteria, Betaproteobacteria, Gammaproteobacteria. In the embodiment presented in example 3, non-culturable bacteria that are present in the immunomodulatory composition are selected from phyla Acidobacteria, Actinobacteria, Armatimonadetes, Bacteroidetes, BRC1, Chlamydiae, Chlorobi, Chloroflexi, Deinococcus-*Thermus*, Firmicutes, Gemmatimonadetes, Nitrospira, OD1, OP11, Planctomycetes, Proteobacteria, TM7, and Verrucomicrobia; classes Acidobacteria_Gp1, Acidobacteria_Gp10, Acidobacteria_Gp16, Acidobacteria_Gp17, Acidobacteria_Gp2, Acidobacteria_Gp21, Acidobacteria_Gp22, Acidobacteria_Gp3, Acidobacteria_Gp4, Acidobacteria_Gp6, Acidobacteria_Gp7, Actinobacteria, Alphaproteobacteria, Anaerolineae, Armatimonadetes_gp2_class_incertae_sedis, Armatimonadetes_gp5_class_incertae_sedis, Armatimonadia, Bacilli, Bacteroidetes_incertae_sedis_class_incertae_sedis, Bacteroidia, Betaproteobacteria, BRC1_class_incertae_sedis, Caldilineae, Chlamydiae, Clostridia, Deinococci, Deltaproteobacteria, Flavobacteria, Gammaproteobacteria, Gemmatimonadetes, Ignavibacteria, Nitrospira, OD1_class_incertae_sedis, OP11_class_incertae_sedis, Opitutae, Planctomycetacia, Spartobacteria, Sphingobacteria, Subdivision3, Thermomicrobia, TM7_class_incertae_sedis, and Verrucomicrobiae; orders Acidimicrobiales, Acidobacteria_Gp1_order_incertae_sedis, Acidobacteria_Gp10_order_incertae_sedis, Acidobacteria_Gp16_order_incertae_sedis, Acido- bacteria_Gp17_order_incertae_sedis, Acidobacteria_Gp2_order_incertae_sedis, Acidobacteria_Gp21_order_incertae_sedis, Acidobacteria_Gp22_order_incertae_sedis, Acidobacteria_Gp3_order_incertae_sedis, Acidobacteria_Gp4_order_incertae_sedis, Acidobacteria_Gp6_order_incertae_sedis, Acidobacteria_Gp7_order_incertae_sedis, Actinomycetales, Alphaproteobacteria_order_incertae_sedis, Alteromonadales, Anaerolineales, Armatimonadales, Armatimonadetes_gp2_order_incetae_sedis, Armatimonadetes_gp5_order_incetae_sedis, Bacillales, Bacteroidales, Bacteroidetes_incertae_sedis_order_incertae_sedis, Bdellovibrionales, BRC1_order_incertae_sedis, Caldilineales, Caulobacterales, Chlamydiales, Clostridiales, Deinococcales, Deltaproteobacteria_order_incertae_sedis, Desulfuromonadales, Flavobacteriales, Gammaproteobacteria_order_incertae_sedis, Gemmatimonadales, Hydrogenophilales, Ignavibacteriales, Lactobacillales, Legionellales, Methylococcales, Myxococcales, Nitrosomonadales, Nitrospirales, OD1_order_incertae_sedis, OP11_order_incertae_sedis, Opitutales, Planctomycetales, Pseudomonadales, Puniceicoccales, Rhizobiales, Rhodospirillales, Rubrobacterales, Solirubrobacterales, Spartobacteria_order_incertae_sedis, Sphaerobacterales, Sphingobacteriales, Subdivision3_order_incertae_sedis, TM7_order_incertae_sedis, Verrucomicrobiales, and Xanthomonadales; families Acetobacteraceae, Acidimicrobineae_incertae_sedis, Acidobacteria_Gp1_family_incertae_sedis, Acidobacteria_Gp10_family_incertae_sedis, Acidobacteria_Gp16_family_incertae_sedis, Acidobacteria_Gp17_family_incertae_sedis, Acidobacteria_Gp2_family_incertae_sedis, Acidobacteria_Gp21_family_incertae_sedis, Acidobacteria_Gp22_family_incertae_sedis, Acidobacteria_Gp3_family_incertae_sedis, Acidobacteria_Gp4_family_incertae_sedis, Acidobacteria_Gp6_family_incertae_sedis, Acidobacteria_Gp7_family_incertae_sedis, Actinospicaceae, Alicyclobacillaceae, Alphaproteobacteria_family_incertae_sedis, Alteromonadaceae, Anaerolineaceae, Armatimonadaceae, Armatimonadetes_gp2_family_incetae_sedis, Armatimonadetes_gp5_family_incetae_sedis, Bacteriovoraceae, Bacteroidetes_incertae_sedis_family_incertae_sedis, Bdellovibrionaceae, Bradyrhizobiaceae, BRC1_family_incertae_sedis, Caldilineaceae, Carnobacteriaceae, Caulobacteraceae, Clostridiaceae_1, Clostridiales_Incertae_Sedis_XVIII, Conexibacteraceae, Coxiellaceae, Cryomorphaceae, Cyclobacteriaceae, Cytophagaceae, Flammeovirgaceae, Flavobacteriaceae, Gammaproteobacteria_family_incertae_sedis, Gemmatimonadaceae, Geobacteraceae, Hydrogenophilaceae, Hyphomicrobiaceae, Ignavibacteriaceae, Lachnospiraceae, Methylobacteriaceae, Methylococcaceae, Micrococcaceae, Nannocystaceae, Nitrosomonadaceae, Nitrospiraceae, Nocardioidaceae, Nocardiopsaceae, OD1_family_incertae_sedis, OP11_family_incertae_sedis, Opitutaceae, Paenibacillaceae_1, Paenibacillaceae_2, Parachlamydiaceae, Pasteuriaceae, Peptostreptococcaceae, Planctomycetaceae, Polyangiaceae, Porphyromonadaceae, Pseudomonadaceae, Pseudonocardiaceae, Puniceicoccaceae, Rhizobiaceae, Rhodobiaceae, Rhodospirillaceae, Rubrobacteraceae, Ruminococcaceae, Saprospiraceae, Simkaniaceae, Sinobacteraceae, Spartobacteria_family_incertae_sedis, Sphaerobacteraceae, Sphingobacteriaceae, Streptococcaceae, Streptosporangiaceae, Subdivision3_family_incertae_sedis, Syntrophorhabdaceae, Thermoactinomycetaceae_1, Thermoactinomycetaceae_2, Thermomonosporaceae, TM7_family_incertae_sedis, Trueperaceae, Verrucomicrobiaceae, Xanthobacteraceae, and Xanthomonadaceae; and genera 3_genus_incertae_sedis, *Aciditerrimonas, Actinomadura, Actinospica, Adhaeribacter, Aequorivita, Algoriphagus, Alicyclobacillus, Alkanibacter, Alterococcus, Ammoniphilus, Aquicella, Arenibacter*, Armatimonadetes_gp2, Armatimonadetes_gp5, *Armatimonas* Armatimonadetes_gp1, *Arthrobacter, Asticcacaulis, Aureispira, Bacteriovorax, Bdellovibrio, Bellilinea, Blastopirellula, Bosea*, BRC1_genera_incertae_sedis, *Caldilinea, Cellvibrio, Chondromyces*, Clostridium_III, Clostridium_sensu_stricto, Clostridium_XI, Clostridium_XIVa, *Cohnella, Conexibacter, Crocinitomix, Cytophaga, Devosia, Dolosigranulum, Dongia, Dyadobacter, Emticicia, Enhygromyxa, Faecalibacterium, Flavobacterium, Fluviicola, Geminicoccus, Gemmata, Gemmatimonas, Geobacter, Gillisia*, Gp1, Gp10, Gp16, Gp17, Gp2, Gp21, Gp22, Gp3, Gp4, Gp6, Gp7, *Haliscomenobacter, Hymenobacter, Ignavibacterium, Labrys, Lactococcus, Lewinella, Longilinea, Luteolibacter, Lutibacter, Magnetospirillum, Marinobacter, Marinoscillum, Methylobacter, Methylobacterium, Methylocaldum, Nannocystis, Neochlamydia, Nitrosomonas, Nitrospira, Nocardioides, Nonomuraea*, OD1_genus_incertae_sedis, *Ohtaekwangia*, OP11_genus_incertae_sedis, *Opitutus, Parachlamydia, Parvibaculum, Pasteuria, Pedobacter, Pelagicoccus, Peredibacter, Petrimonas, Planctomyces, Planifilum, Pontibacter, Prosthecobacter, Proteiniclasticum, Pseudoxanthomonas, Reichenbachiella, Rhizobium, Rhizomicrobium, Rhodanobacter, Rhodomicrobium, Rhodopirellula, Roseomonas, Rubrobacter, Schlesneria, Simkania, Singulisphaera, Skermanella, Solimonas, Sorangium*, Spartobacteria_genera_incertae_sedis, *Sphaerobacter, Sphingobacterium, Spirosoma, Sporacetigenium, Stella, Steroidobacter, Symbiobacterium, Syntrophorhabdus, Thermoactinomyces, Thermobacillus, Thermobifida, Thermobispora, Thermoflavimicrobium, Thiobacillus*, TM7_genus_incertae_sedis, *Truepera, Tumebacillus, Verrucomicrobium, Wandonia, Winogradskyella*, and *Zavarzinella*, and at small frequencies also genera *Acinetobacter, Mycobacterium* and *Lactobacillus*.

In an embodiment of the first aspect, the immunomodulatory composition is free of at least one of the microbial taxa mentioned in the previous embodiment.

In yet another embodiment of the first aspect, the exact frequencies and abundances of microbial taxa mentioned above vary within the same product. The reason is that efficacy of the current invention is at least partially based on the overall effect of the immunomodulatory composition, not on the effect of individual strains.

In an embodiment of the first aspect processing comprises increasing at least one of usability, comfortability and safety, by using at least one of the following methods: grinding, sieving, pulverizing and mixing with an aqueous solution or lotion. This step provides the immunomodulatory composition in a form, which does not contain sharp edges that can injure a subject or cause infection.

In an embodiment of the first aspect, the total microbial abundance of the subject remains stable but the abundance of at least one microbial phylum, order, class, family, subfamily or genus increases immediately after the treatment on at least one tissue of the subject. In this embodiment, the increase is caused by at least one non-culturable OTU.

In an embodiment the subject is a mammal, such as an animal subject or a human subject, preferably a human subject.

In an embodiment of the first aspect the diversity of the material derived from nature is at least 3.5 at Shannon index or Shannon diversity index.

In an embodiment of the first aspect the diversity of the immunomodulatory composition is at least 4 at Shannon index or Shannon diversity index.

In an embodiment the microbial diversity of the immunomodulatory composition is indicated at Shannon diversity index by subsampling 2000 operational taxonomic units from a 0.25 g wet sample at the 97% similarity level of operational taxonomic units.

In an embodiment the microbial richness of the immunomodulatory composition is at least 130 OTUs calculated by rarefying 2000 operational taxonomic units from a 0.25 g wet sample at 97% similarity level.

In an embodiment the abundance of pathogens in the immunomodulatory composition is 0 or at the same or lower level as found in everyday living environment.

In an embodiment the immunomodulatory composition is biologically inactivated before use. Preferably at least one parameter describing richness, diversity or abundance is determined immediately before inactivation, such as any or each of parameters i-iii of the first aspect or parameter c. of an embodiment of the first aspect.

In an embodiment of the first aspect the richness of the immunomodulatory composition is at least 350 operational taxonomic units.

In an embodiment of the first aspect the microbial abundance of the immunomodulatory composition is at least 1 000 000 000 16 S and 18 S copies $g^{-1}$ ww.

In an embodiment of the first aspect the bacterial abundance of the immunomodulatory composition is at least 1 000 000 000 16 S copies $g^{-1}$ ww.

In a preferable embodiment in the immunomodulatory composition the proportion of non-culturable bacterial 16 S DNA is at least 1% of total bacterial 16 S DNA. In another embodiment, the proportion of non-culturable bacterial 16 S DNA is at least 10%. In a preferable embodiment, the proportion of non-culturable bacterial 16 S DNA is at least 50%. Immunomodulatory compositions complying with said parameters comprise a fraction of non-culturable bacteria, which is efficient to provide immunomodulatory effect in a subject.

In an embodiment in the present immunomodulatory composition the mean number of 16S copies/g (w/w) is at least 1.000.000.000, preferably at least 1.500.000.000, more preferably at least 3.000.000.000.

In an embodiment the present immunomodulatory composition is sieved and in it the mean number of 16S copies/g (w/w) is at least 4.000.000.000, preferably at least 5.000.000.000, more preferably at least 5.500.000.000.

In an embodiment the diversity of the immunomodulatory composition is at a level or near the level of the material derived from nature. In a preferred embodiment bacterial diversity is essentially the same in the material derived from nature and in the immunomodulatory composition. In another preferred embodiment bacterial diversity, richness and abundance are higher in the immunomodulatory composition than in the material derived from nature. The higher values are a result of processing. In an embodiment, sieved or filtered materials have more surface area per g ww and hence more microbes per g ww than raw materials. In another embodiment, a thorough mixing of different processed materials with different microbial communities increases diversity, richness and potentially also abundance of the resulting new immunomodulatory composition so that its diversity, richness and potentially also abundance are higher than in materials derived from nature.

In an embodiment of the first aspect the composition further comprises culturable bacteria. In another embodiment the culturable bacteria are added to the composition. In yet another embodiment the culturable bacteria comprise *Lactobacillus* or *Mycobacterium*.

In an embodiment the material derived from nature is composted. In another embodiment the material derived from nature comprises composted leaves, needles, peat, or a combination thereof. In yet another embodiment the level of coliform bacteria is controlled during composting.

In an embodiment the material derived from nature is inactivated. The inactivation process is selected from heat, radiation, filtration, freezing, chemical treatment or a combination thereof. Preferably the inactivation process is selected such that it provides material which is essentially free from living organisms, but which is able to elicit the same or similar immunomodulatory effect as the material derived from nature before inactivation. Example 3 provides an exemplary method to test suitability of the inactivation process for the present invention.

In an embodiment the spatial variation of the microbial community of the immunomodulatory composition is homogeneous and optionally the density of pathogens and other pests is controlled.

In an embodiment of the first aspect the processing comprises
 a) homogenizing spatial variation in microbial community;
 b) controlling pathogens levels and other pests using at least one inactivation method.

In an embodiment option a) comprises using at least one of the following methods: grinding, crushing, sieving, filtering, extraction with an aqueous solution.

In an embodiment option b) comprises using at least one of the following methods: homogenization, extraction, evaporation or at least one inactivation method.

Currently, soil materials, such as composted dressings, are manufactured for use in gardening and sieved and mixed coarsely. Then, mesh size is optimal for gardening purposes i.e. 8 mm or larger, typically 25-35 mm. In the current invention, the mesh size is preferably selected for homogenizing microbial community i.e. it is less than 8 mm, preferably 2-5 mm or even smaller. Optionally sieved material is to be mixed thoroughly, which affects microbial diversity, richness and abundance and homogenizes spatial variation in microbial community. The process may be used as a means for controlling the density of pathogens and other pests.

An advantage achieved with the embodiment is that a composition having a defined particle size and good storage stability can be obtained. An additional advantage is that the preparation is homogenous and its quality can be controlled in comparison to preparations based on unprocessed raw materials. Such a composition is easier to administer as accurate doses and it is more comfortable to use than unprocessed raw materials. It is also safer to use, as it does not contain sharp-edged large particles that can injure skin or other tissues.

Importantly, the inactivated or homogenous and quality controlled preparations have pathogen levels that are at or below those observed in everyday living environment, as evidenced in examples 5-7 for the composition according to the invention. This is a difference of the inventive composition in view of unprocessed raw material such as natural soil, peat, plant and animal materials and existing organic soil products; all these raw materials may contain patches of pathogens that can infect humans or toxins derived from pathogens. One of the reasons for the high levels of pathogens observed in example 7 is patchy distribution of microbial cells as the non-immunomodulatory compositions are not homogenized and mixed.

As evidenced by Example 3, the lyophilization and the optional extraction step preserve the immunomodulatory activity of the composition, while providing a composition which has better storage stability and easy application in formulations such as lotions, sprays, cosmetic products and other consumer products and baby and toddler products as shown in example 8.

In an embodiment the immunomodulatory composition has a level of pathogens encountered in everyday living environment, or an abundance of 0.

In another embodiment the pathogens is selected from enterovirus, rhinovirus, rotavirus, norovirus, *Giardia* and *Cryptosporidium*.

In an embodiment the level of pathogens is not more than 550 or less potentially pathogenic bacterial 16 S sequences per 0.25 g ww sample.

In an embodiment of the first aspect the immunomodulatory composition is essentially free from pathogens. In an embodiment the pathogens are selected from *E. coli, Salmonella, Klebsiella* or a combination thereof.

In an embodiment the level of pathogens is controlled during manufacturing process of the composition. In another embodiment the controlling is carried out at a level of genus or species of the pathogen.

In an embodiment of the first aspect the material derived from nature is soil or plant material.

In an embodiment the immunomodulatory composition has a microbial diversity of at least 3 at Shannon diversity index obtained by subsampling 2000 operational taxonomic units from a 0.25 g wet sample at the 97% similarity level of operational taxonomic units.

In an embodiment the immunomodulatory composition has a microbial richness of at least 130 operational taxonomic units (97% similarity level) calculated by rarefying to 2000 sequences from a sample of 0.25 g wet weight of the immunomodulatory composition.

In an embodiment the immunomodulatory composition is inactivated and the microbial richness, diversity or abundance determined immediately before the inactivation.

In an embodiment the microbial community comprises viable non-culturable bacteria and/or immunomodulatory components of viable non-culturable bacteria in the form of inactivated or killed bacteria.

In an embodiment of the first aspect the material derived from nature is selected from soil material; plant material; animal material excluding feces; microbial material from aqueous environment; sludge; compost; insects; algae; or material stream from industrial, agricultural, silvicultural, water purification, water filtration, aquacultural, mining or peat production, such as a byproduct; and moss from peat production areas.

In a preferable embodiment the material derived from nature is soil material and/or plant material.

In an embodiment of the first aspect the immunomodulatory composition comprises at least one microbial taxon selected from classes Acidobacteria_Gp1, Acidobacteria_Gp10, Acidobacteria_Gp16, Acidobacteria_Gp17, Acidobacteria_Gp2, Acidobacteria_Gp21, Acidobacteria_Gp22, Acidobacteria_Gp3, Acidobacteria_Gp4, Acidobacteria_Gp6, Acidobacteria_Gp7, Actinobacteria, Alphaproteobacteria, Anaerolineae, Armatimonadetes_gp2_class_incertae_sedis, Armatimonadetes_gp5_class_incertae_sedis, Armatimonadia, Bacilli, Bacteroidetes_incertae_sedis_class_incertae_sedis, Bacteroidia, Betaproteobacteria, BRC1_class_incertae_sedis, Caldilineae, Chlamydiae, Clostridia, Deinococci, Deltaproteobacteria, Flavobacteria, Gammaproteobacteria, Gemmatimonadetes, Ignavibacteria, Nitrospira, OD1_class_incertae_sedis, OP11_class_incertae_sedis, Opitutae, Planctomycetacia, Spartobacteria, Sphingobacteria, Subdivision3, Thermomicrobia, TM7_class_incertae_sedis, and Verrucomicrobiae; orders Acidimicrobiales, Acidobacteria_Gp1_order_incertae_sedis, Acidobacteria_Gp10_order_incertae_sedis, Acidobacteria_Gp16_order_incertae_sedis, Acidobacteria_Gp17_order_incertae_sedis, Acidobacteria_Gp2_order_incertae_sedis, Acidobacteria_Gp21_order_incertae_sedis, Acidobacteria_Gp22_order_incertae_sedis, Acidobacteria_Gp3_order_incertae_sedis, Acidobacteria_Gp4_order_incertae_sedis, Acidobacteria_Gp6_order_incertae_sedis, Acidobacteria_Gp7_order_incertae_sedis, Actinomycetales, Alphaproteobacteria_order_incertae_sedis, Alteromonadales, Anaerolineales, Armatimonadales, Armatimonadetes_gp2_order_incetae_sedis, Armatimonadetes_gp5_order_incetae_sedis, Bacillales, Bacteroidales, Bacteroidetes_incertae_sedis_order_incertae_sedis, Bdellovibrionales, BRC1_order_incertae_sedis, Caldilineales, Caulobacterales, Chlamydiales, Clostridiales, Deinococcales, Deltaproteobacteria_order_incertae_sedis, Desulfuromonadales, Flavobacteriales, Gammaproteobacteria_order_incertae_sedis, Gemmatimonadales, Hydrogenophilales, Ignavibacteriales, Lactobacillales, Legionellales, Methylococcales, Myxococcales, Nitrosomonadales, Nitrospirales, OD1_order_incertae_sedis, OP11_order_incertae_sedis, Opitutales, Planctomycetales, Pseudomonadales, Puniceicoccales, Rhizobiales, Rhodospirillales, Rubrobacterales, Solirubrobacterales, Spartobacteria_order_incertae_sedis, Sphaerobacterales, Sphingobacteriales, Subdivision3_order_incertae_sedis, TM7_order_incertae_sedis, Verrucomicrobiales, and Xanthomonadales; families Acetobacteraceae, Acidimicrobineae_incertae_sedis, Acidobacteria_Gp1_family_incertae_sedis, Acidobacteria_Gp10_family_incertae_sedis, Acidobacteria_Gp16_family_incertae_sedis, Acidobacteria_Gp17_family_incertae_sedis, Acidobacteria_Gp2_family_incertae_sedis, Acidobacteria_Gp21_family_incertae_sedis, Acidobacteria_Gp22_family_incertae_sedis, Acidobacteria_Gp3_family_incertae_sedis, Acidobacteria_Gp4_family_incertae_sedis, Acidobacteria_Gp6_family_incertae_sedis, Acidobacteria_Gp7_family_incertae_sedis, Actinospicaceae, Alicyclobacillaceae, Alphaproteobacteria_family_incertae_sedis, Alteromonadaceae, Anaerolineaceae, Armatimonadaceae, Armatimonadetes_gp2_family_incetae_sedis, Armatimonadetes_gp5_family_incetae_sedis, Bacteriovoracaceae, Bacteroidetes_incertae_sedis_family_incertae_sedis, Bdellovibrionaceae, Bradyrhizobiaceae, BRC1_family_incertae_sedis, Caldilineaceae, Carnobacteriaceae, Caulobacteraceae, Clostridiaceae_1, Clostridiales_Incertae_Sedis_XVIII, Conexibacteraceae, Coxiellaceae, Cryomorphaceae, Cyclobacteriaceae, Cytophagaceae, Flammeovirgaceae, Flavobacteriaceae, Gammaproteobacteria_family_incertae_sedis, Gemmatimonadaceae, Geobacteraceae, Hydrogenophilaceae, Hyphomicrobiaceae, Ignavibacteriaceae, Lachnospiraceae, Methylobacteriaceae, Methylococcaceae, Micrococcaceae, Nannocystaceae, Nitrosomonadaceae, Nitrospiraceae, Nocardioidaceae, Nocardiopsaceae, OD1_family_incertae_sedis, OP11_family_incertae_sedis, Opitutaceae, Paenibacillaceae_1, Paenibacillaceae_2, Parachlamydiaceae, Pasteuriaceae, Peptostreptococcaceae, Planctomycetaceae, Polyangiaceae, Porphyromonadaceae, Pseudomonadaceae, Pseudonocardiaceae, Puniceicoccaceae, Rhizobiaceae, Rhodobiaceae, Rhodospirillaceae, Rubrobacteraceae, Ruminococcaceae, Saprospiraceae, Simkaniaceae, Sinobacteraceae, Spartobacteria_family_incertae_sedis, Sphaerobacteraceae, Sphingobacteriaceae, Streptococcaceae, Streptosporangiaceae, Subdivision3_family_incertae_sedis, Syntrophorhabdaceae, Thermoactinomycetaceae_1, Thermoactinomycetaceae_2, Thermomonosporaceae, TM7_family_incertae_sedis, Trueperaceae, Verrucomicrobiaceae, Xanthobacteraceae, and Xanthomonadaceae; and genera 3_genus_incertae_sedis, *Aciditerrimonas, Actinomadura, Actinospica, Adhaeribacter, Aequorivita, Algoriphagus, Alicyclobacillus, Alkanibacter, Alterococcus, Ammoniphilus, Aquicella, Arenibacter,* Armatimonadetes_gp2, Armatimonadetes_gp5, *Armatimonas* Armatimonadetes_gp1, *Arthrobacter, Asticcacaulis, Aureispira, Bacteriovorax, Bdellovibrio, Bellilinea, Blastopirellula, Bosea,* BRC1_genera_incertae_sedis, *Caldilinea, Cellvibrio, Chondromyces, Clostridium*_III, *Clostridium_sensu_stricto, Clostridium*_XI, *Clostridium*_XIVa, *Cohnella, Conexibacter, Crocinitomix, Cytophaga, Devosia, Dolosigranulum, Dongia, Dyadobacter, Emticicia, Enhygromyxa, Faecalibacterium, Flavobacterium, Fluviicola, Geminicoccus, Gemmata, Gemmatimonas, Geobacter, Gillisia,* Gp1, Gp10, Gp16, Gp17, Gp2, Gp21, Gp22, Gp3, Gp4, Gp6, Gp7, *Haliscomenobacter, Hymenobacter, Ignavibacterium, Labrys, Lactococcus, Lewinella, Longilinea, Luteolibacter, Lutibacter, Magnetospirillum, Marinobacter, Marinoscillum, Methylobacter, Methylobacterium, Methylocaldum, Nannocystis, Neochlamydia, Nitrosomonas, Nitrospira, Nocardioides, Nonomuraea,* OD1_genus_incertae_sedis, *Ohtaekwangia,* OP11_genus_incertae_sedis, *Opitutus, Parachlamydia, Parvibaculum, Pasteuria, Pedobacter, Pelagicoccus, Peredibacter, Petrimonas, Planctomyces, Planifilum, Pontibacter, Prosthecobacter, Proteiniclasticum, Pseudoxanthomonas, Reichenbachiella, Rhizobium, Rhizomicrobium, Rhodanobacter, Rhodomicrobium, Rhodopirellula, Roseomonas, Rubrobacter, Schlesneria, Simkania, Singulisphaera, Skermanella, Solimonas, Sorangium, Spartobacteria_genera_incertae_sedis, Sphaerobacter, Sphingobacterium, Spirosoma, Sporacetigenium, Stella, Steroidobacter, Symbiobacterium, Syntrophorhabdus, Thermoactinomyces, Thermobacillus, Thermobifida, Thermobispora, Thermoflavimicrobium, Thiobacillus,* TM7_genus_incertae_sedis, *Truepera, Tumebacillus, Verrucomicrobium, Wandonia, Winogradskyellaand Zavarzinella, Acinetobacter, Mycobacterium* and *Lactobacillus*.

In an embodiment of the first aspect the immunomodulatory composition further comprises material from at least one eukaryote or virus selected from Fungi, bacteriophage, plant virus, Ecdysozoa, including Nematoda, Arachnida, Acari, Amobae, insects and other multicellular but microscopic soil organisms and unicellular eukaryotes such as Amoebozoa and unicellular fungi.

In an embodiment the immunomodulatory composition is in the form of a topical composition, lotion, cream, gel, powder, pill, food ingredient, drink constituent, detergent, conditioner, shampoo, soap, liquid soap, extract, dried extract, freeze-dried extract, spray, steam, water vapor, gas, aerosol or a dry mixture packed inside bags that allow the contact of the immunomodulatory composition with the subject. In another embodiment the immunomodulatory composition is in the form of, or packed inside, a container, package or packet, such as a jewel or accessory.

In another embodiment the immunomodulatory composition is in the form of a chip, granule, microparticle or a combination thereof. In another form the immunomodulatory composition is in the form of an infusion, steam, water vapor or an aqueous composition comprising active agents obtainable from the immunomodulatory composition.

In another embodiment the immunomodulatory composition is provided in a carrier. In an embodiment the carrier comprises aqueous vapour, aerosol or liquid.

In an embodiment the immunomodulatory composition is lyophilized and the liquid obtained during lyophilization is recovered.

In an embodiment the immunomodulatory composition is inactivated. Preferably the inactivation process at least partially exposes intracellular components to enhance immune response.

In an embodiment the immunomodulatory composition comprises at least one additive. The additive may be selected from a fragrant, preservative, coloring agent, moisturizer, bulking agent or stabilizer.

In an embodiment of the second aspect the use provides a change in the microbiome of the subject.

In an embodiment of the second aspect the use prevents a negative change in the diversity of the microbiome of the subject.

In an embodiment of the second aspect the exposure comprises inhalation, ingestion, touching or a combination thereof.

In an embodiment the exposure is by ingesting a dose unit comprising the immunomodulatory composition. In an embodiment the dose unit is a pill, or a capsule.

In an embodiment of the second aspect the exposure is continued for at least 2 weeks.

In an embodiment the exposure is carried out sequentially at intervals of not more than 7 days, preferably on daily basis.

In an embodiment of the second aspect the exposure is carried out sequentially at intervals of max 30 days. In another embodiment the exposure is daily. In another embodiment the exposure happens three times a day. In yet another embodiment the exposure is continuous and lasts for at least one month.

In an embodiment of the second aspect exposing comprises bringing an area on the skin of the subject in contact with the immunomodulatory composition for at least 1 second. In another embodiment the contact is for at least 10 s, 30 s, 1 min, 2 min, 3 min, 5 min, 10 min, 30 min, 1 h, 2 h, 3 h, 5 h or 12 h. In an embodiment the contact is continuous. The contact time can also be interrupted by a short interval after which the contact continues.

In an embodiment the area on the skin of the subject is hand or hands, foot or feet, head, neck, lip or lips, breast or breasts, genital area or face.

In an embodiment the exposure comprises direct hand exposure with the present immunomodulatory composition, or exposure with fabric packet containing the present immunomodulatory composition. In an embodiment the hands are rubbed optionally followed by washing the hands with water. In an embodiment the packet contains *Sphagnum* moss as the immunomodulatory composition.

In an embodiment of the second aspect
a. the subject has an altered microbial diversity and/or richness or abundance compared to a reference subject;
b. exposing is carried out at least until the microbial diversity, richness and/or abundance returns towards a level corresponding to the level of a reference subject or closer to the level of the reference subject; and
c. the reference subject is a subject having a microbial diversity, richness and/or abundance corresponding to a level observed for subjects living in a non-urban environment.

Preferably the reference subject has a healthy microbiome, which does not expose the reference subject to immunomodulatory disorders.

The use provides the subject with an increased microbial diversity, richness and/or abundance compared to the subject before exposure.

In an embodiment exposing is continued after reaching a predetermined level of microbial diversity, richness and/or abundance to maintain a diverse microbiome.

In an embodiment the internal microbial diversity of the subject increases upon exposure to the immunomodulatory composition. In an embodiment the internal microbial diversity is diversity of gut microbiome.

In an embodiment the exposure to the immunomodulatory composition selectively induces immunoregulatory response in the subject. In an embodiment the response is an IL-10 immunoregulatory response, or an IL10-mediated immunomodulatory response. In another embodiment inflammatory response is not increased. In yet another embodiment the response is a TGF-β immunoregulatory response, or an TGF-β-mediated immunomodulatory response. In another embodiment the immunoregulatory response is both an IL-10 mediated and TGF-β mediated immunomodulatory response.

In an embodiment the subject is a human subject having a disorder of immunity or a human subject living in an urban environment wherein microbial diversity, richness and/or abundance is lower than in the material derived from nature.

In an embodiment of the second aspect the subject is a human subject having a disorder of immunity or a subject having a risk to develop immune related disorder. In an embodiment the risk is due to inadequate microbial exposure.

Administering the immunomodulatory composition to subjects in need of strengthening their immune system may benefit from the administration.

In an embodiment of the third, fourth or the fifth aspect the drying is carried out by oven drying.

In an embodiment of the third, fourth or fifth aspect the obtained product is moisturized to provide lotion or liquefied material.

In an embodiment of the third, fourth or fifth aspect the process comprises an inactivating step.

In an embodiment of the third, fourth or fifth aspect the process comprises lyophilizing the material obtained in any of steps a-e and taking it directly to the sterilization step. In another embodiment the raw material is sterilized.

In an embodiment of the third, fourth or the fifth aspect the method comprises lyophilizing the material obtained in step b-e and taking it directly to the sterilization step.

In an embodiment of the third or the fourth aspect material derived from nature is extracted. Preferably extraction is carried out using an aqueous solvent, such as water.

In an embodiment of the third, fourth or fifth aspect the method comprises lyophilizing the material obtained in step d and taking it directly to step f.

In an embodiment of the third, fourth, or fifth aspect material derived from nature comprises plant material and the processing comprises grinding.

In another embodiment the material derived from nature comprises plant material and the processing comprises directly extracting material derived from nature.

In an embodiment of the third, fourth or fifth aspect the method comprises lyophilizing the material obtained in step a-d.

In an embodiment of the third aspect the method additionally comprises at least one of the following steps:
 i. sterilizing the raw material to provide sterilized material;
 ii. evaporating the raw material to provide evaporated material;
 iii. Extracting the product obtained in step a., b., c., d., e., f., or g. to provide an extract;
 iv. lyophilizing the extract to provide the lyophilized extract;
 v. oven-drying the extract to provide oven-dried extract;
 vi. evaporating the extract to provide gaseous material;
 vii. condensing the evaporated extract to provide condensed material;
 viii. composting the raw material to provide composted material.

In an embodiment of the third, fourth or fifth aspect an inactivation step is carried out to inactivate pathogens. In a preferred embodiment inactivation is by heat treatment. In another inactivation is carried out until the level of pathogens is low enough for safe external or internal use for a human subject.

In an embodiment of the third, fourth or fifth aspect the method further comprises grinding the raw material to a particle size of 1000 μm or smaller. In another embodiment, the particle size is less than 1000 μm in at least 50% of the mass of the immunomodulatory composition, as evidenced in example 10.

In an embodiment of the third, fourth or fifth aspect the method for manufacturing comprises further extracting the lyophilized raw material with an aqueous solution or organic solvent, and optionally drying and optionally resuspending into aqueous solution.

In an embodiment of the fifth aspect the compartment is configured to receive the composition in at least one unit dose form. In an embodiment the unit dose is a permeable or semi permeable bag, pouch, patch, packet or a container. In an embodiment the unit dose is made of cotton fabric enclosing the immunomodulatory composition. In another embodiment the unit dose contains immunomodulatory composition in a predetermined amount, such as a predetermined weight, volume, abundance, richness or diversity.

In an embodiment of the fifth aspect the compartment comprises a pocket adapted to receive a unit dose of the immunomodulatory composition and adapted to allow exposure of a subject to the immunomodulatory composition.

In an embodiment of the fifth aspect the article is selected from textile, fabric, a piece of headwear, a hat, sheet, pillow, duvet, blanket, mattress, and baby carrier.

In an embodiment of the fifth aspect the article is selected from
 textile, fabric, a piece of headwear, a hat, sheet, pillow, duvet, blanket, mattress, baby carrier;
 tissue paper, diaper, handkerchief, breastfeeding towel, feminine towel, pad, cushion, underlay;
 food such as beverage;
 pharmaceutical or personal care product such as pill, spray, toothpaste, lipstick, deodorant, mouthwash, talcum;
 cigarette;
 toy, building block, security blanket, comfort object, jewel;
 a piece of cloth, a children's cloth, a baby cloth, or a baby hat.

In an embodiment of the fifth aspect the article is a piece of cloth. In a preferred embodiment the cloth is a children's cloth, even more preferably a baby cloth, such as a baby hat.

In an embodiment of the sixth aspect the apparatus comprises means for providing aerosol of the immunomodulatory composition.

In an embodiment of the sixth aspect the apparatus is an air refresher, inhalator, nebulizer, or air moisturizer.

In an embodiment of the sixth aspect the apparatus is configured to receive a cartridge for the immunomodulatory composition. The immunomodulatory composition may be provided in liquid form inside the cartridge. The apparatus may further comprise means for evaporating, spraying or nebulizing the immunomodulatory composition.

In an embodiment the immunomodulatory composition is mixed to control amount of pathogens. By mixing the non-culturable bacteria compete with pathogens and culturable fast growing bacteria, and reduce their amount.

In an embodiment the material derived from nature is of non-human origin. In another embodiment the material derived from nature does not contain raw materials known to contain potential pathogens, such as feces or dung not treated with antibiotics.

In an embodiment the present immunomodulatory composition is used to spray plants, preferably edible plants. This embodiment is advantageous because it can be used to spray for example houseplants with which people are in contact with. It can also be used to spray edible plants in urban or rural gardens, which enhances their immunomodulatory effect upon use.

EXAMPLES

Example 1: Effect on Skin Bacterial Diversity

Methods
Sampling and Experiment

Two urban volunteers conducted the experiment. Fourteen different materials derived from nature were modified by sieving different composted, soil and plant based mixtures. The raw materials comprised of dung, horse dung, chicken dung, deciduous leaf litter, plant debris, horticultural peat, sludge, fine mineral soil such as silt as well as crushed tree bark mulch. Volunteers rubbed their hands in a test material for 20 seconds, washed their hands without soap in tap water for 5 seconds, and dried the hands with hand towels. The procedure was repeated until all test materials were tested. Materials were tested in random order. No more than two materials were tested in the same day and there was at least five hours between the tests. Volunteers did not wash their hands before exposures, in order to validate the changes in frequency, abundance and diversity of skin bacteria.

A skin swab (back of the right hand, 3×3 cm area, 9 wipes) was taken twice, immediately before exposure and immediately after drying hands with a hand towel. A cotton wool stick was first wetted in Tween® 20, used in sampling and cut to a sterile polyethene sample tube.

Sample Preparation to MiSeq Sequencing for Skin Samples

Skin swap samples were stored in deep freezer (<−70° C.) in tubes containing Tween 20 (MP Biomedicals) (0.1%)+ NaCl (0.1 M, J. T. Baker) before DNA extraction. Total DNA was extracted from samples using PowerSoil® DNA Isolation Kit (MoBio Laboratories, Inc., Carlsbad, Calif., USA) according to the manufacturer's standard protocol. The swap and the liquid (approximately 650 µl Tween+ NaCl) were transferred to the PowerBead tube for a homogenization and lysis procedure. DNA was checked with agarose gel (1.5%) electrophoresis (120 V, 30 min). Total DNA concentration was measured with Quant-iT™ PicoGreen® dsDNA reagent kit (Thermo scientific, MA, USA). DNA was analyzed for bacterial (16S) communities using a two-step PCR approach to avoid a 3'-end amplification bias resulting from the sample-specific DNA tags (Berry et. al 2011). The v1-3 regions within the 16S ribosomal RNA (rRNA) gene was amplified by primary PCR (three replicates from each sample) using pA and PD Illumina primers. Primary PCR was carried out in a reaction mixture (reaction volume 50 µl) consisting of 1 µl each of 10 mM deoxynucleoside triphosphates (dNTPs; Thermo scientific, MA, USA), 5 µl forward primer pA_Illum_FP (10 µM; ATCTACACTCTTTCCCTACACGACGCTCTTCCGATCTAGAGTTT-GATCMTGGCTCAG) and 5 µl reverse primer pD'_Illum_RP (10 µM; GTGACTGGAGTTCAGACGTGTGCTCTTCCGATCTGTAT-TACCGCGGCTGCTG), 0.5 µl 2 U/µl Phusion Green Hot Start II High-Fidelity DNA polymerase (Thermo scientific, MA, USA), 10 µl 5× Green HF PCR buffer (F-537), 5 µl template DNA and 23.5 µl sterile water. The PCR reaction was run in a thermocycler (MJ Research, MA, USA) as follows: initial denaturation at 98° C. for 5 min, followed by 30 cycles with denaturation at 94° C. for 1 min, annealing for 10 sec at 50° C. and extension for 1 min at 72° C., and then a final extension at 72° C. for 10 min. The PCR products were detected with agarose gel (1.5%) electrophoresis (120 V, 1 h). The PCR products were purified using Agencourt AMPure XP solution (Beckman Coulter Ins.).

Illumina adapter overhang nucleotide sequences were added to the 16S rRNA gene-specific sequences in the secondary PCR. The secondary PCR and sequencing was performed at the institute of biotechnology (University of Helsinki) using Illumina MiSeq platform. An approximately 500 bp fragment covering the V1-V3 variable regions of the 16S rRNA gene was amplified and using primers pA (mixture of 5'-AGAGTTTGATCMTGGCTCAG-3', 5'-TAGAG AGTTTGATCMTGGCTCAG-3', 5'-CTCTAGAGTTT-GATCMTGGCTCAG-3') and pD' (mixture of 5'-GTAT-TACCGCGGCTGCTG-3', 5'-CGTATTACCGCGGCT GCTG-3', 5'-TAGTATTACCGCGGCTGCTG-3'). The primers had 5' overhangs for Illumina sequencing 5'-ATC-TACACTCTTTCCCTACACGACGCTCTTCCGATCT-3' for pA and 5'-GTGACTGGAGTTCAGACGTGTG CTCTTCCGATCT-3' for pD'. The amplification was done using a two-step PCR protocol. In the second PCR-step full length adapters and Indexes were introduced. The PCR protocol was as described in Koskinen et. al. (2011). The sequencing was done as paired-end (300 bp+300 bp) on a MiSeq Illumina instrument using a v3 reagent kit.

Bacterial Abundance—qPCR Method

The q-PCRs of bacterial 16S rRNA were based on SYBR green detection. PCRs were carried out with the Light Cycler 96 Quantitative real-time PCR machine (MJ Research, MA, USA). The forward primer used was pE 5"-AAA CTC AAA GGA ATT GAC GG-3' (SEQ ID NO:1) and the reverse primer pF 5"-ACG AGC TGA CGA CAG CCA TG-3' (SEQ ID NO: 2) (Öqvist et al. 2008). All samples were run in triplicates in 20 µl reactions containing 10 µl 2× PowerUp SYBR Green Master Mix (Thermo scientific, MA, USA), 0.2 µl 20 mg/ml BSA, 0.5 µl of each primer (10 µM), and the sample template. A standard curve was included in every run to allow quantitation of the number of bacterial 16S copies present in the original sample. The q-PCR run was as follows: initial denaturation at 95° C. for 2 min, followed by 40 cycles of denaturation at 95° C. for 10 s, annealing for 20 sec at 53° C. and extension for 30 s at 72° C. Melting curve analysis on the amplicon was as follows: 95° C. for 10 s, 65° C. for 60 s, 97° C. for 1 s, 37° C. for 30 s with continuous measurement of the fluorescence signal. DNA of *Cupriavidus necator* JMP134 (DSM 4058) was used as the standard. The standard worked also as a positive control while sterile water was used as a negative control.

Sequence Processing

We analyzed the sequence data using Mothur-program (versions 1.36.1; Schloss et al. 2009). The sequence processing protocol partly followed the pipeline suggested by Schloss et al. (2011) and (Kozich et al. 2013). The paired sequences contained in reverse and forward fastq files were aligned into a contig. Sequences were trimmed and screened to remove any mismatches with primer or DNA-tag sequences, ambiguous bases and homopolymers larger than 8 bp long. Sequences were aligned using Mothur version of SILVA bacterial reference sequences (version 102; Pruesse et al. 2007) and the sequences which were not aligned to a reference alignment of the correct sequencing region were removed. Unique sequences and their frequency in each sample were identified, and then, almost identical sequences (>99% similar) were preclustered to minimize sequencing errors (Huse et al. 2010) and screened for chimeras (UCHIME, Edgar et al. 2011) using the abundant sequences as a reference. The chimeric sequences were removed. We calculated a pairwise distance matrix for unique sequences and clustered OTUs at 97% sequence similarity using the nearest neighbor algorithms. Sequences were classified using the Mothur version of Bayesian classifier (Wang et al. 2007) with the RDP training set version 9 (Cole et al 2009). Sequences classified to Chloroplast, Mitochondria, unknown, Archaea and Eukaryota were removed from the analyses. Rare OTUs that were represented with 10 or fewer sequences in the whole data were removed. Finally, all the samples were rarefied to 7388 sequences which was the minimum total number of sequences in a sample.

Statistical Methods

The Wilcoxon signed-rank test was used for comparing the number of bacterial 16S copies in hands before and immediately after exposure. The Wilcoxon signed-rank test is used for comparing two related samples when the population cannot be assumed to be normally distributed. Wilcoxon signed-rank test was also used for comparing taxonomic richness and Shannon diversity index before and after exposure.

The difference between bacterial composition in hands before and immediately after exposure was studied using permutational multivariate analysis of variance (PERMANOVA; Anderson 2001). PERMANOVA was run using R package vegan and a function adonis. This analysis was not run for Acidobacteria because one of the samples did not include any Acidobacteria. Analysis was based on Bray-Curtis distance and it was conducted for both relative abundance data as well as for presence-absence data.

Results

Wilcoxon signed rank test showed that number of bacterial 16S copies was significantly larger after the exposure on immunomodulatory compositions compared to the number of copies before exposure (p-value=0.001709, V=6) (FIG. 1).

Figure 2A:
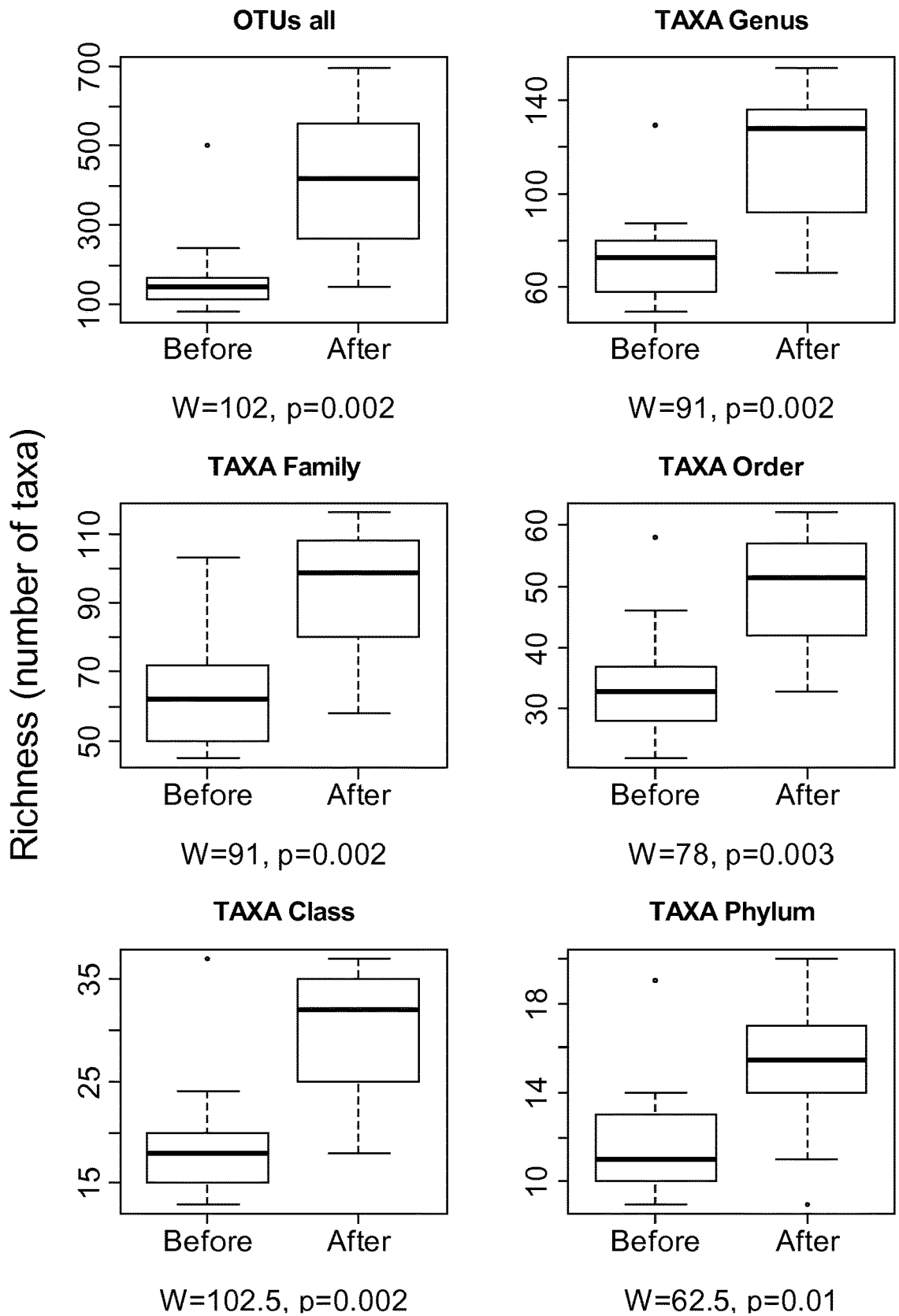
FIG. 2A-B discloses box-plots showing bacterial richness before and after an exposure of hands to different immunomodulatory compositions comprising non-culturable microbial community. The compositions are different composted and sieved agricultural byproducts and other sieved materials derived from nature. Thick line is the median, the boxes show the lower and upper hinges and whiskers show the most extreme data points. If the most extreme data point is at least 1.5 times the interquartile range of the box, it is shown as a circle. P-values and statistics (W) are based on Wilcoxon signed rank test. A) Number of OTUs and number of taxa at different taxonomic levels. B) Number of OTUs within five dominant phyla (Phyl.), number of OTUs for unclassified bacteria at phylum level (Phyl. unclassified) and number of OTUs within three classes (Alpha-, Beta- and Gammaproteobacteria). As FIG. 2 shows, the immunomodulatory composition comprising non-culturable microbial community increases microbial richness on human skin, and it also increases the richness within major bacterial phyla, classes and unclassified bacteria on human skin.
Figure 2B:
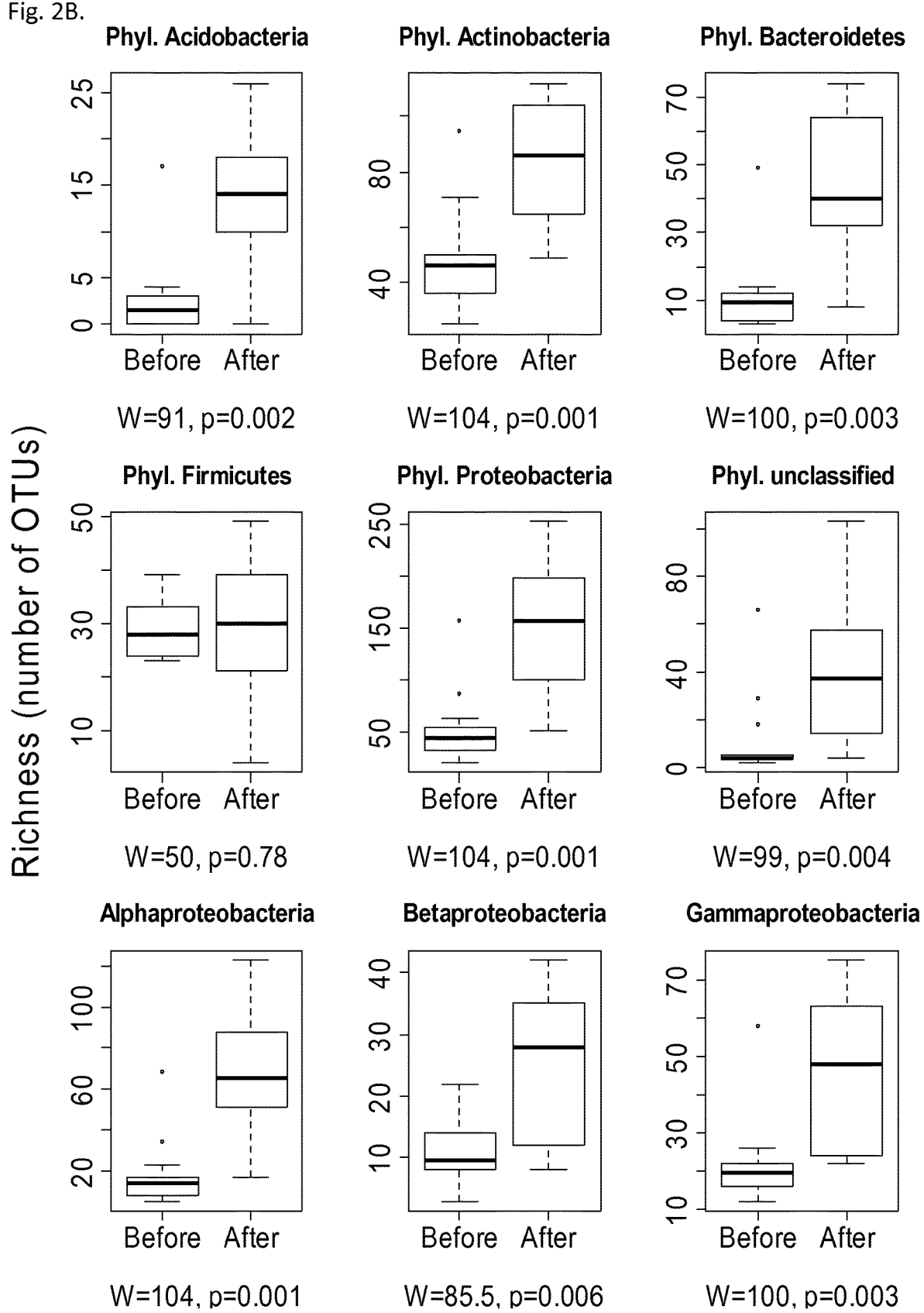
Figure 3A:
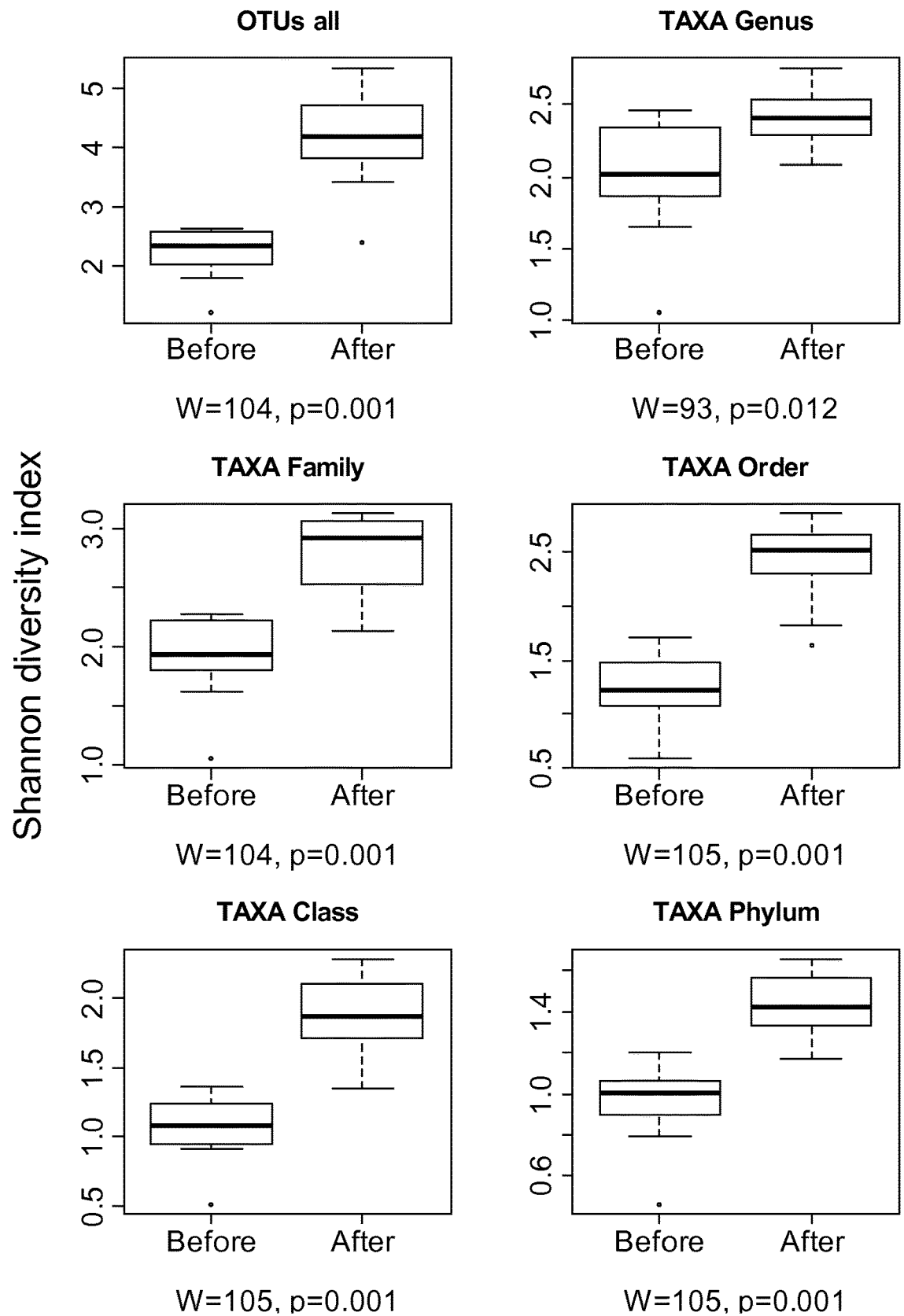
FIG. 3A-3B discloses box-plots showing bacterial diversity before and after an exposure of hands to different immunomodulatory compositions comprising non-culturable microbial community. The compositions are different composted and sieved agricultural byproducts and other sieved materials derived from nature. Thick line is the median, the boxes show the lower and upper hinges and whiskers show the most extreme data points. If the most extreme data point is at least 1.5 times the interquartile range of the box, it is shown as a circle. P-values and statistics (W) are based on Wilcoxon signed rank test. A) Shannon diversity index based on all OTUs and taxa at different taxonomic levels. B) Shannon diversity index based on OTUs within five dominant phyla (Phyl.), number of OTUs for unclassified bacteria at phylum level (Phyl. unclassified) and number of OTUs within three classes (Alpha-, Beta- and Gammaproteobacteria). As FIG. 3 shows, the immunomodulatory composition comprising non-culturable microbial community increases microbial diversity on human skin, and it also increases the diversity within major bacterial phyla, classes and unclassified bacteria on human skin.
Figure 3B:
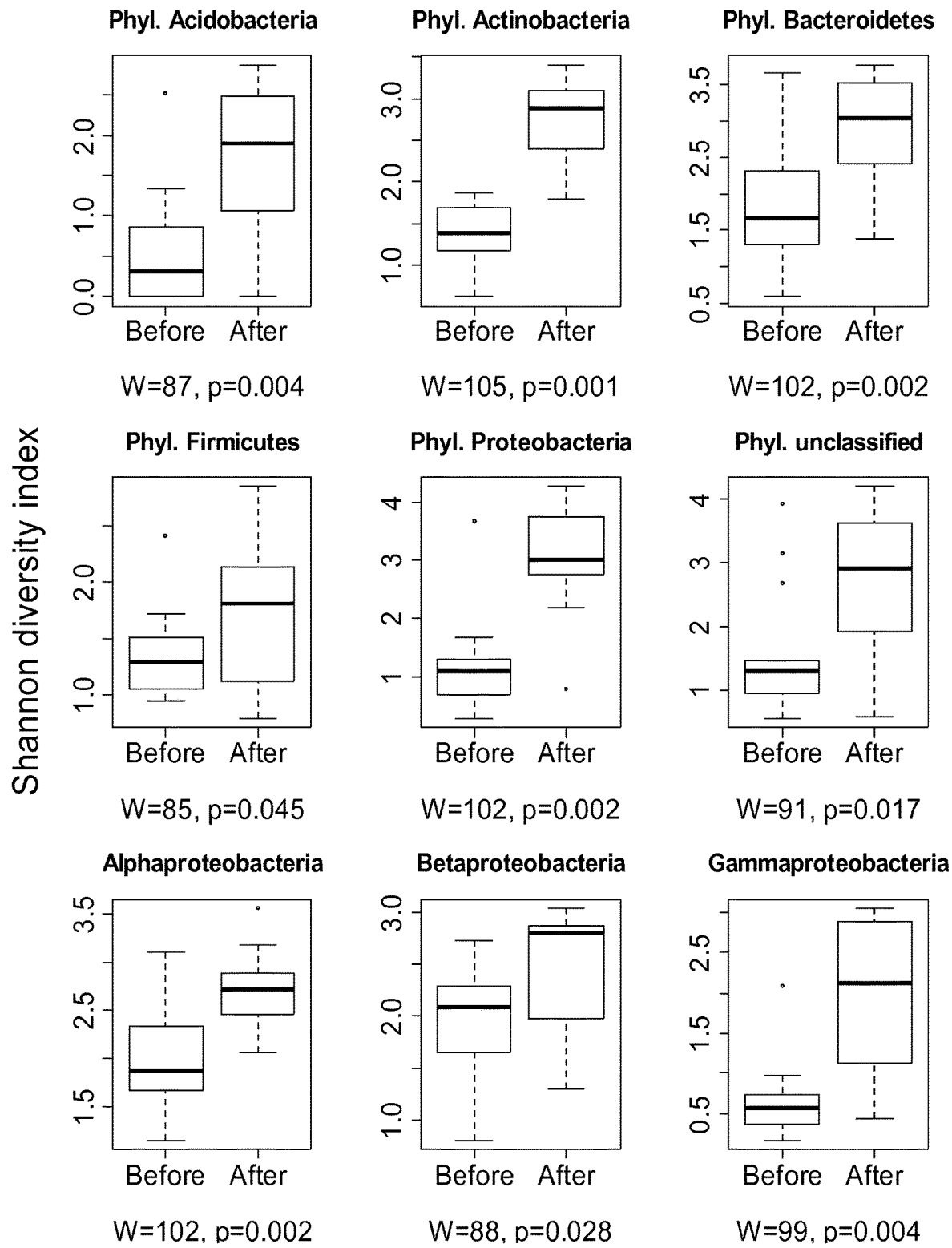

Richness (FIG. 2) and Shannon diversity index (FIG. 3) were significantly (p<0.05) higher after exposure in all tested taxonomic groups excluding the difference in richness for phylum Firmicutes. PERMANOVA showed that bacterial composition was significantly different in hands after exposure compared to the bacterial composition before exposure in all tested taxonomic groups (Table 1).

TABLE 1

P-values for the difference between bacterial composition in hands before and after exposure to immunomodulatory compositions based on permutational multivariate analysis of variance (PERMANOVA). Analysis was based on Bray-Curtis distance for relative abundances and presence-absence data. Analysis was not run for Acidobacteria because one of the samples did not include any Acidobacteria.

|  | Abundance data | Presence-absence data |
|---|---|---|
| OTUs all | 0.001 | 0.001 |
| TAXA Genus | 0.001 | 0.001 |
| TAXA Family | 0.001 | 0.001 |
| TAXA Order | 0.001 | 0.001 |
| TAXA Class | 0.001 | 0.001 |
| TAXA Phylum | 0.002 | 0.001 |
| OTUs within Phylum Actinobacteria | 0.001 | 0.001 |
| OTUs within Phylum Bacteroidetes | 0.002 | 0.002 |
| OTUs within Phylum Firmicutes | 0.007 | 0.001 |
| OTUs within Phylum Proteobacteria | 0.001 | 0.001 |
| OTUs within Phylum unclassified | 0.001 | 0.001 |
| OTUs within Class Alphaproteobacteria | 0.001 | 0.001 |
| OTUs within Class Betaproteobacteria | 0.001 | 0.002 |
| OTUs within Class Gammaproteobacteria | 0.003 | 0.001 |

As the results show, bacterial abundance, richness and diversity on skin could be increased after exposure to the immunomodulatory composition according to the invention. The effect was found at different taxonomic levels in the whole bacterial community, and within major phyla and classes. As the results further show (Table 1), the immunomodulatory compositions also changed bacterial community composition in hands. The technical effect is that the current invention is suitable for increasing bacterial abundance, richness and diversity of urban subjects.

Example 2—Effects of Immunomodulatory Composition on Fecal Diversity

Methods

Experimental Groups, Exposure and Sampling

Fourteen urban volunteers (healthy adults, age 27-63 years) participated in the experiment, which followed a case-control design. The pairs were matched for sex, age (difference max 11 years), pet ownership (no pet or dog), and dwelling type (apartment building, row house, detached house). One person of the pair was randomly picked to be part of the case group while the other became part of the control group.

The case group conducted two weeks' exposure, i.e. they rubbed their hands in a soil and plant based immunomodulatory composition three times every day: before breakfast, before dinner/evening snack, and before going to bed. Each exposure lasted for 10-20 seconds after which the study subjects were instructed to wash their hands with tap water but without soap for five seconds and pad their hands dry with a towel.

The soil and plant based immunomodulatory composition was manufactured by sieving and combining various commercially available, composted soil materials. The general ingredients for these soil-types were various compositions of industrial composts (raw materials cattle dung, horse dung, chicken dung, deciduous leaf litter, plant debris, horticultural peat, sludge, fine mineral soil such as silt as well as crushed tree bark mulch). The immunomodulatory composition consisted of four major ingredients (three types of composted soil materials and dried *Sphagnum* moss) and eight minor ingredients (peat and different composted soil materials). Before mixing, the major and minor components were sieved with Ø 5 mm and Ø 2 mm sieves, respectively, except for the moss that was dried and crushed and mixed. The combined ratio for the test material was 4:1:0.5 for each major composted materials, moss and each minor materials, respectively.

Stool samples were collected from the study subjects just before the start of the exposure (day 0), immediately after the exposure period (day 14), and three weeks after the exposure had ended (day 35). All study subjects were given a Pneumococcus vaccination immediately after the two weeks' exposure period.

Sample Preparation to MiSeq Sequencing for Stool Samples

The total DNA was extracted from 30-60 milligrams of frozen unprocessed stool sample using the PowerSoil DNA isolation kit (MoBio, Carlsbad, Calif.) according to manufacturer's protocol. One water sample was added into each extraction batch.

The microbiome was assessed using the variable region 4 of the 16S bacterial ribosomal gene. Amplification was done using 17 µl of AccuPrime Pfx SuperMix (Invitrogen, Waltham, Mass.), 1 µl of template DNA and µl of paired set of index primers (Schloss et al. 2011). Amplification was initiated with denaturation at 95° C. for 5 minutes, followed by 30 cycles of denaturation, 95° C., 15 seconds, primer annealing, 55° C., 30 seconds and extension, 68° C., 1 minute. Products were checked by 1% agarose gel electrophoresis (100V for 30 minutes). PCR products were diluted in water and purified with Ampure magnetic beads (Beckman Coulter, Fullerton, Calif.). The PCR products were quantified with KAPA Library quantification kit (Kapa Biosystems, Wilmington, Mass.) and further were equalized according to the results. Mock community, which is a mix of bacterial DNA of a known content, was used as positive control for next generation sequencing (NGS).

Sequencing was performed on a MiSeq machine (Illumina, San Diego, Calif.) with a 2×250 bp version 2 sequencing kit according to manufacturer's protocol.

Sequence Processing

Stool NGS data was processed and analyzed using mothur (version 1.36.1; Schloss et al. 2009), custom python scripts, and QIIME (Caporaso et al., 2010). The sequence processing protocol partly followed the pipeline suggested by Schloss et al. (2011) and (Cinek et al., 2016). The paired sequences contained in reverse and forward fastq files were aligned into a contig. Sequences were trimmed and screened to remove any mismatches with primer or DNA-tag sequences, ambiguous bases and homopolymers larger than 8 bp long. Sequences were aligned using Mothur version of SILVA bacterial reference sequences (version 102; Pruesse et al. 2007) and the sequences which were not aligned to a reference alignment of the correct sequencing region were removed. Unique sequences and their frequency in each sample were identified and screened for chimeras (usearch academic version, http://www.drive5.com/usearch) using the abundant sequences as a reference. The chimeric sequences were removed. We calculated a pairwise distance matrix for unique sequences and clustered OTUs at 97% sequence similarity using the nearest neighbor algorithms. Sequences were classified using the Mothur version of Bayesian classifier (Wang et al. 2007) with the RDP training set version 9 (Cole et al 2009). Sequences classified to Chloroplast, Mitochondria, unknown, Archaea and Eukaryota were removed from the analyses. Green genes (DeSantis et al., 2006) core imputed reference was further integrated for building phylogenetic tree required for further downstream statistical analysis.

Statistical Methods

The R language platform was used for statistical testing and plotting. Key packages include the microbial package Phyloseq V16.2 (McMurdie & Holmes, 2013) and fold change estimation Deseq2 (Love, Huber, & Anders, 2014). The purpose of statistical analyses was to find out if the immunomodulatory composition changes richness and ecosystem diversity in fecal samples. Differences in fecal bacterial richness between cases and controls were analyzed using Fisher diversity index i.e. Fisher's alpha (Magurran 2004). Ecosystem diversity was tested using Bray-Curtis dissimilarity data (Legendre and Legendre 1998). Changes and rates of change between the start (day 0) and the end (day 14) of the exposure were especially important, as the composition change should be directly comparable to the exposure effects on gut microbiome.

Subsampling was accomplished using phyloseq function rarefy_even_depth with sample sum of 2000 reads to filter rare OTUs and at the same time to preserve maximal bacterial diversity representation. All samples within case and controls passed this threshold. The difference between bacterial composition in stool before and after exposure was calculated using rate of change in sample diversity between days 0 and 14. The second measure was ecosystem diversity (Bray-Curtis) dissimilarity scores between days 0 and 14.

Rate of change of Fisher diversity index and ecosystem diversity measured as Bray-Curtis dissimilarity were divided to two equally large groups for Fisher's exact test (Fisher 1954).

Medians were used as cut points so that values below median formed one group (n=7) and values above median another group (n=7). Thereafter cases and controls were compared.

Results and Interpretation

We focus on sample species richness and ecosystem diversity dissimilarities results related to change over time points in concordance with experiment design.

Fisher diversity index values of sample species richness varied between 0.027 and 0.084. There were no differences between cases and controls in the actual values, but the rate of change from day 0 to day 14 was different (Table 2). Six out of seven cases belonged to the above median group and therefore the p-value in Fisher's exact test was 0.029. Table 2 thus shows the increased sample diversity (6 out of 7 cases) from day 0 to day 14, using Fisher diversity index.

Figure 4:
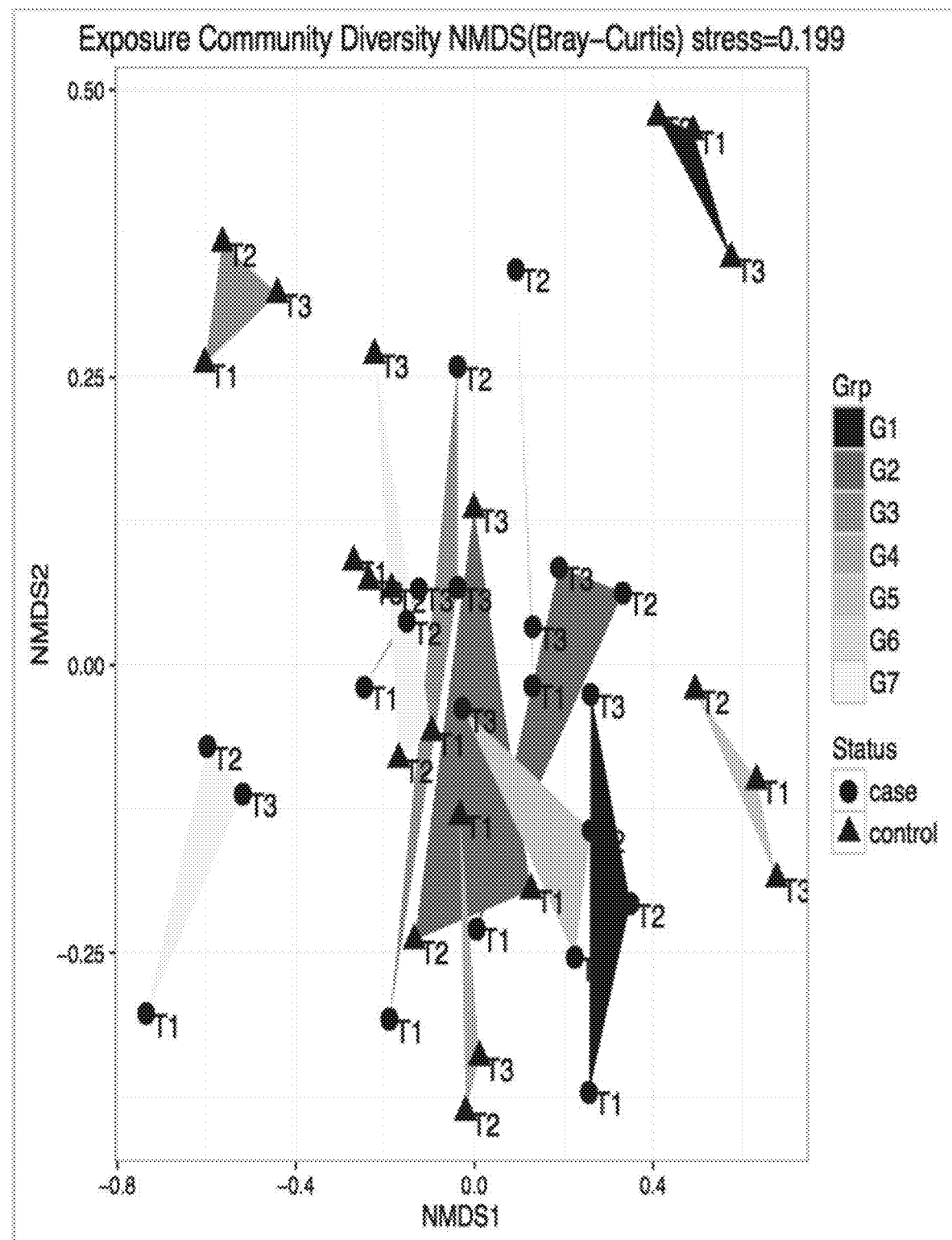
FIG. 4. The bacterial ecosystem diversity i.e. community composition of fecal samples in two groups of volunteers. The case group exposed their hands to an immunomodulatory composition three times a day for two weeks. The control group did not receive the immunomodulatory composition. Dissimilarity in community composition between groups was plotted using Non-Metric Multidimensional Scaling (NMDS) with Bray-Curtis dissimilarity data (details in example 2). Table 2 has calculations used in revealing statistically significant ecosystem diversity changes (Fisher's exact test, P-Value 0.029) between exposed and non-exposed subjects. Together with Table 2, the technical effect is that the external use of the immunomodulatory composition according to the current invention can increase species change and diversity in stool microbial community.

Values of Bray-Curtis dissimilarity index of ecosystem diversity varied between 0.21 and 0.46. The values were higher in the case than the control group. Six out of seven cases belonged to the above median group and therefore the p-value in Fisher's exact test was 0.029. Table 2 thus shows that the case group exhibited higher amount of species change (6/7). To illustrate the difference between cases and controls, FIG. 4 shows ecosystem diversity as measured with Bray-Curtis distance with NMDS ordinates. The graph nodes are labeled with time and case/control variables.

As the results confirm, volunteer subjects exposed to the immunomodulatory composition, from day 0 to day 14, had higher rates of change in species richness and higher amount of species change in stool samples compared to non-exposed volunteers. This is an impactful revelation as gut microbiota has been linked to numerous immune diseases including inflamed bowel systems, type 1 diabetes, and Crohn's disease. A technical effect is that the external use of the immunomodulatory composition as described herein can lead to an internal increase in microbial diversity.

TABLE 2

Sample richness changes as measured by rate of change in Fisher diversity index and ecosystem diversity as measured by Bray-Curtis dissimilarity between days 0 and 14. P = 0.029 in Fisher's exact test for both variables.

| Pairs | Rate of change, Case | Rate of change, Control | Ecosystem diversity, Case | Ecosystem diversity, Control |
| --- | --- | --- | --- | --- |
| 1 | 0.032 | 0.027 | 0.399 | 0.369 |
| 2 | 0.130 | 0.013 | 0.397 | 0.290 |
| 3 | 0.041 | −0.073 | 0.217 | 0.267 |
| 4 | 0.078 | −0.073 | 0.322 | 0.229 |
| 5 | −0.034 | 0.024 | 0.301 | 0.288 |
| 6 | 0.032 | 0.089 | 0.384 | 0.253 |
| 7 | 0.081 | −0.039 | 0.462 | 0.257 |

Example 3—Peripheral Blood Mononuclear Cell Stimulation with Extracted and Freeze Fried Immunomodulatory Composition Methods Approximately 1 liter of sieved immunomodulatory composition (details in Example 2) was taken in a clean plastic container. Ultra-pure Milli-Q water was poured slowly into the container and mixed thoroughly until the soil was saturated (i.e. water started dripping when the wet soil was held in hand). Approximately 800 ml water was needed for saturation. The soil water mixture was kept inside a laminar hood at room temperature for 4 hours covered with a lid but holes on the side walls of the container allowed adequate air circulation. The soil-water mixture was then hand-squeezed using sterilized laboratory gloves over an ethanol-cleaned 250 µm sieve placed above another sterile plastic container. The extract was collected in separate 50 ml Falcon tubes. All the samples were frozen at −20° C. prior to freeze-drying. Approximately 48 hours was needed for the freeze drying process to complete.

The extracted and freeze fried immunomodulatory composition was resuspended in the original volume of MilliQ water. The suspended extract was clarified by low speed centrifugation (5 min 50 g) and filtered with 35 µm filter. The supernatant was directly used in the stimulation tests. Alternatively it was heat inactivated by 5 minutes treatment at 120° C. or was further filtered twice using first 1 µm and subsequently 0.45 µm filters. Both heat inactivated and filtered extracts were also used in stimulation tests. In addition, a mixture of anti-CD3 and anti-CD28 antibodies was used as a positive control that is known to stimulate immune responses in white blood cells.

Blood was drawn into CPT tubes (Sodium Citrate Vacutainer® CPT™ Mononuclear Cell Preparation Tube, BD) and centrifuged according to the tube manufacturers' instructions. Peripheral blood mononuclear cells (PBMCs) were isolated from the tubes, washed twice with RPMI 1640 medium (Life Technologies, Carlsbad, Calif., USA) and placed at 2×106 cells/mL in RPMI 1640 supplemented with 10% human AB serum (inactivated, Sigma-Aldrich, St. Louis, Mo., United States), 1% penicillin-streptomycin (PAA Laboratories, Pasching, Austria), and 1% L-glutamine (Life Technologies, Carlsbad, Calif., USA). Dilutions of the immunomodulatory composition and stimulant suspensions were prepared in supplemented RPMI medium, added to the PBMC containing wells and incubated for 24 or 48 hours at 37° C. and 5% CO2. Final concentrations of control stimulants in the wells were 5 and 0.5 µg/mL for CD3 and CD28, respectively. The cell culture supernatants were collected and IFN-gamma and IL-10 levels were measured in supernatants with ELISA (eBioscience, San Diego, Calif., USA) according to manufacturers' instructions.

Results and Interpretation

Figure 5A:
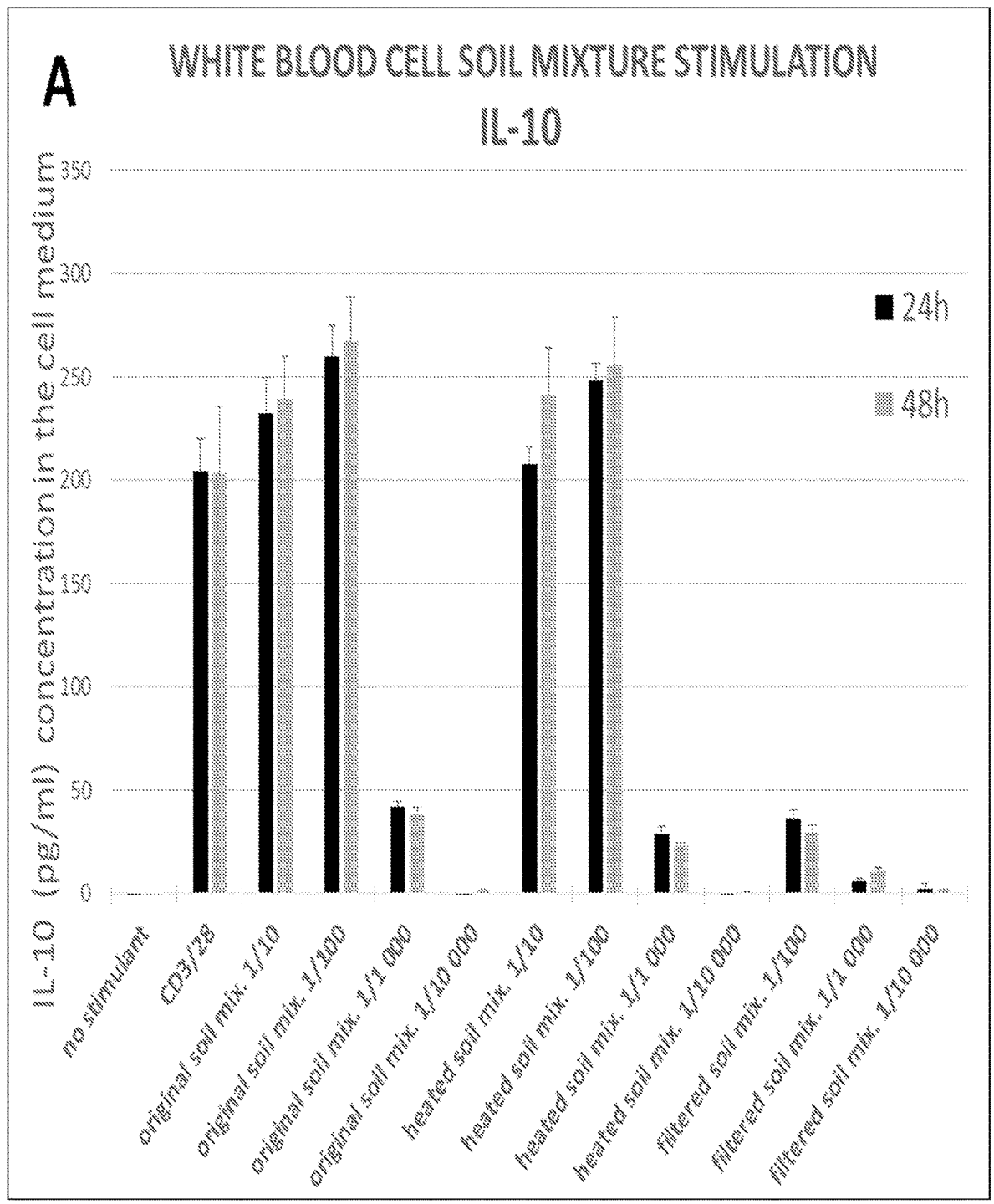
FIG. 5. Stimulation of the peripheral blood mononuclear cells (PBMCs) with the extracted, freeze-dried and resuspended immunomodulatory composition that is called as soil mixture extract in FIG. 5. PBMCs were stimulated either with resuspended i.e. original, heat inactivated or filtered immunomodulatory composition for 24 and 48 hours. Stimulation by anti-CD3/CD28 was used as a positive control in the stimulation experiment. Panel A shows the IL-10 expression in PBMCs and panel B shows the IFN-gamma (i.e. IFNg) expression compared to positive anti-CD3/28 control. The technical effect is that the immunomodulatory composition according to the current invention can induce predominantly immunoregulatory IL-10-type responses while it does not induce proinflammatory IFN-gamma-type responses. In addition, killing the bacteria by heat-treatment did not abolish IL-10 responses while elimination of bacteria by filtration through 0.45 μm filter decreased IL-10 responses considerably. This indicates that the favorable immunoregulatory effect is dependent of the presence of bacteria in the immunomodulatory composition.
Figure 5B:
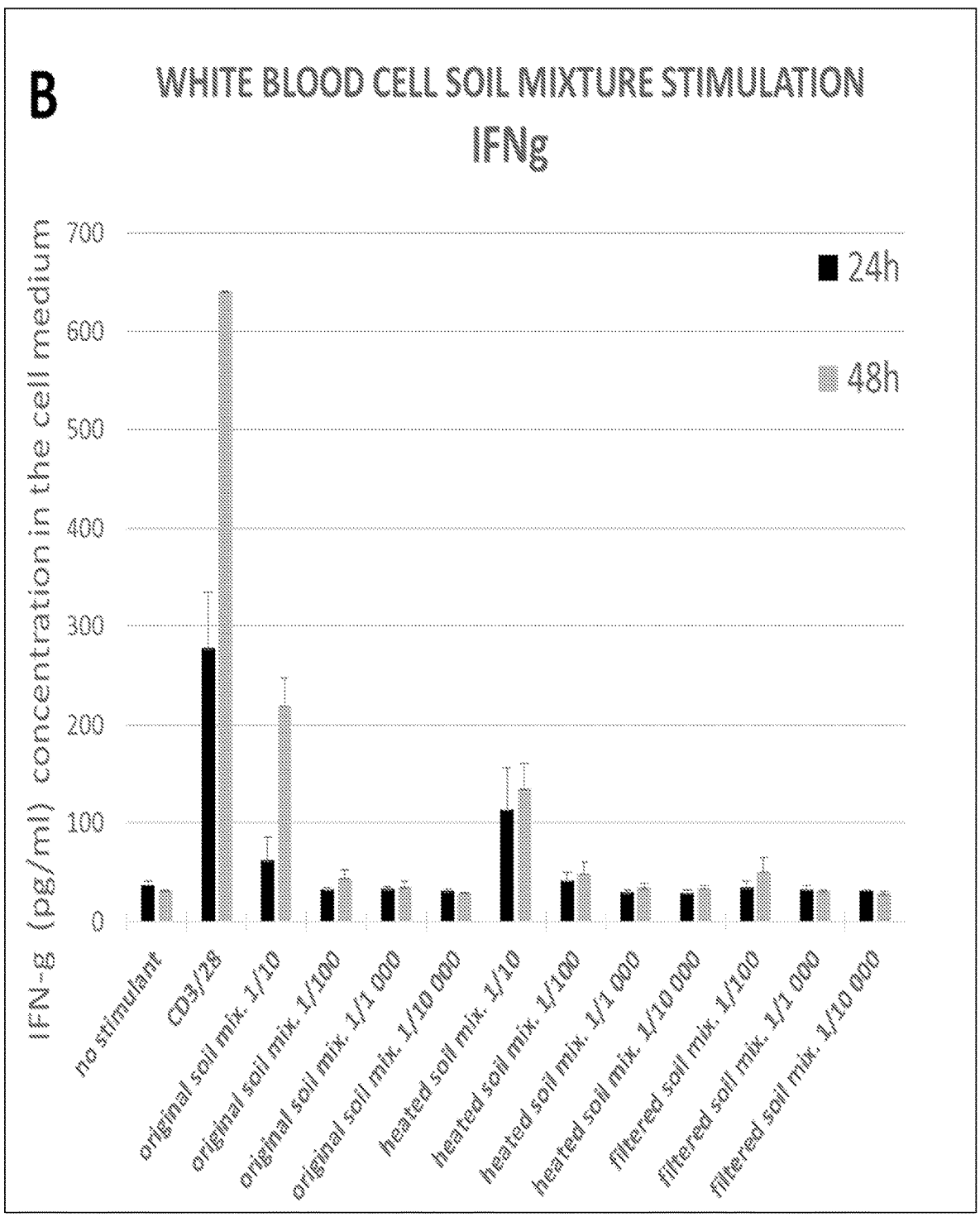

FIG. 5. panel A shows the IL-10 expression in PBMCs induced by the extracted, freeze-dried and resuspended immunomodulatory composition determined at 24 and 48 hours post treatment time points. The positive control consisted of anti-CD3/28 antibodies. Both non-treated and heat treated immunomodulatory compositions gave strong interleukin-10 (IL-10) induction down to dilution 1/100 and to lesser at 1/1000 dilution at both time points. In contrast, the induction of the filtered composition was lower and only detectable in dilution 1/100.

FIG. 5. panel B shows that the extracted, freeze-dried and resuspended immunomodulatory composition induce a lower interferon-gamma (IFN-g) expression compared to positive anti-CD3/28 control. The induction was detected only at dilution 1/10 for non-treated soil mixture at 48 h time point and weakly for heat treated immunomodulatory composition at dilution 1/10 at both studied time points. All other treatments and dilutions were not able to generate any induction compared to negative control.

The results show that the extracted, freeze-dried and resuspended immunomodulatory composition is able to induce a robust immunoregulatory IL-10 response in white blood cells, whereas the proinflammatory IFN-gamma response is much weaker. It is possible to find a suitable dosage of the immunomodulatory composition to induce immunoregulatory response without inducing inflammation. This also shows that both intact (living) and heat inactivated immunomodulatory composition are able to induce a beneficial immunoregulatory response in white blood cells. In contrast, the ability of filtered composition which lacks bacteria to induce IL-10 was clearly decreased. The technical effect is that the immunomodulatory composition according to the current invention can induce immunoregulatory response without inducing inflammation, and this property depends on the presence of bacteria in this composition. Hence, the immunomodulatory compositions according to the current invention are able to induce a strong immunoregulatory response, which is beneficial to prevent or treat immune mediated disorders and to activate immune system in a beneficial way.

Example 4—Comparison of Richness, Diversity and Abundance in Urban Mineral Soils, Materials Derived from Nature and Immunomodulatory Compositions Methods Materials Compared Immunomodulatory compositions comprising non-culturable microbial community, their raw materials, mineral soil materials and natural organic soils were compared to find out potential differences in microbial richness, diversity and abundance.

Organic soil materials derived from nature were manufactured as in example 1. They were divided to two separate groups, those that comprised only non-coniferous composted materials derived from nature (called jointly as Organic materials—non-coniferous), and those that contained also peat or coniferous plant parts (called jointly as Organic materials—coniferous). Sieved immunomodulatory composition was manufactured as in example 2. Sieved immunomodulatory composition consisted of two separate mixing batches that were not manufactured simultaneously. Freeze dried immunomodulatory composition was manufactured as in example 3. Organic raw materials derived from nature consisted of *Sphagnum* mosses of different geographic origin (3 samples), peat of different geographic origin (2 samples) and two types of wood mulch. Pieces of natural forest soil (1 m$^2$ each) were taken from two sources of different geographic origin. They were cut from forest and transferred immediately to laboratory where sampling was made. Commercially available mineral soil materials were received from Rudus Oy in May 2016. The materials consisted of playsand 0/2 mm, playground gravel ⅛ mm, stone dust 0/3 mm, coarse gravel 2/5 mm, and coarse sand 0/8 mm.

Sampling of the Sieved Immunomodulatory Composition

Preparation of the sieved immunomodulatory composition is described in example 2. Altogether eight samples were taken. Four samples were taken from each batch of the immunomodulatory composition. As sieved immunomodulatory composition was divided into 5 l buckets before sampling, each sample was taken from a separate bucket. After sampling, the buckets were distributed to study subjects in the case group of example 2.

Sampling of the Freeze Dried Immunomodulatory Composition

Freeze dried extract was prepared following the same method described in Example 3, i.e. the sieved immunomodulatory composition described above was used. Three samples of the freeze dried extract were used for extraction and sequencing. Additional 3 samples were also used in qPCR.

Sampling of Materials Derived from Nature

The materials derived from nature were mixed thoroughly before sampling. Samples were taken from 5 separate spots. Distance between spots was at least 3 cm. Sample size was 2 g. They consisted of four types of organic materials. Seven samples belonged to the group Organic soil—non-coniferous, and seven to the group Organic soil—coniferous. Seven samples were organic raw materials derived from silvicultural and peat production activities (Organic raw material). Natural forest soils were sampled as follows: sample size 2 g, 5 subsamples per soil, the distance between sampling points was at least 10 cm, subsamples were pooled and mixed thoroughly before molecular analyses.

Sampling of Mineral Soils

Mineral soil types were sampled separately. Sampling was done with a sterile polyethene spoon and the sample was freezed in a clean polyethene freezer bag. All the materials are used particularly in planning of urban spaces e.g. outdoor areas of daycare centers.

Sample Preparation to MiSeq Sequencing

Sample preparation to MiSeq sequencing was done according to Veach et al. (2015). Samples were stored in deep freezer (<−70° C.) before DNA extraction. For each sample, approximately 0.25 g soil was used for DNA extraction. For organic soils, three sample replicates were extracted and pooled before sequencing. For freeze dried extract and mineral soils, no replicates were used. Total DNA was extracted from samples using PowerSoil® DNA Isolation Kit (MoBio Laboratories, Inc., Carlsbad, Calif., USA) according to the manufacturer's standard protocol. Three organic soil samples were extracted using Power-Max® DNA Isolation Kit (one sample from each of the following groups: Organic soil—coniferous, Organic raw material and Natural forest). DNA was checked with agarose gel (1.5%) electrophoresis (120 V, 30 min). Total DNA concentration was measured with Quant-iT™ PicoGreen® dsDNA reagent kit (Thermo scientific, MA, USA). The DNA concentration was adjusted to 0.35-0.4 ng/μl to each sample. DNA was analyzed for bacterial (16S) communities using a two-step PCR approach to avoid a 3'-end amplification bias resulting from the sample-specific DNA tags (Berry et al. 2011). The V4 region within the 16S ribosomal RNA (rRNA) gene was amplified by primary PCR as triplicates using 505F and 806R primers (Caporaso et al. 2012). Primary PCR was carried out in a reaction mixture (reaction volume 50 μl) consisting of 1 μl each of 10 mM deoxynucleoside triphosphates (dNTPs; Thermo scientific, MA, USA) 5 μl forward primer 505F (10 μM; 5'-GTGCCAGCMGCCGCGGTAA-3') and 5 μl reverse primer 806R (10 μM; 5'-GGACTACHVGGGTWTCTAAT-3'), 0.5 μl 2 U/μl Phusion Green Hot Start II High-Fidelity DNA polymerase (Thermo scientific, MA, USA), 10 μl 5× Green HF PCR buffer (F-537), 5 μl template DNA and 23.5 μl sterile water. The PCR reaction was run in a thermocycler (MJ Research, MA, USA) as follows: initial denaturation at 98° C. for 5 min, followed by 25 cycles with denaturation at 94° C. for 1 min, annealing for 10 sec at 50° C. and extension for 1 min at 72° C., and then a final extension at 72° C. for 10 min. A positive control (*Cupriavidus necator* JMP134, DSM 4058) was included in PRC runs to ensure that the PCR worked, and a negative control (sterile water) was run to detect any possible contamination. DNA was detected with agarose gel (1.5%) electrophoresis (120 V, 1 h). The PCR products were purified using Agencourt AMPure XP solution (Beckman Coulter Ins.) to reduce carryover of primary PCR primers. Triplicates of the cleaned amplicons were pooled and diluted 1:5.

Cleaned and diluted primary PCR products were targeted in the secondary PCR (TagPCR). Reaction mixture to the TagPCR was equal as above except reverse primer included a 12 bp unique Multiplexing Identifier tag (MID-806R). Amplification program was the same as above except there were only seven cycles for soil products and ten cycles for other samples. TagPCR products were detected on agarose gel (1.5%) electrophoresis (120 V, 1 h), purified with Agencourt AMPure, pooled and the DNA concentration was measured with PicoGreen. The sequencing was performed at the Kansas State University using Illumina MiSeq platform. The sequencing was performed using Illumina MiSeq platform with a 2×300 bp version 3 kit sequencing kit according to manufacturer's protocol. The GeneRead DNA Library I Core Kit (Qiagen, catalog #180432) was used to ligate Illumina's TruSeq adapters to amplicons.

qPCR Method

Quantitative PCR was conducted following same method described in Example 1.

Sequence Processing

We analyzed the sequence data using mothur-program (version 1.35.1 for organic soils and v.1.38.1 for other samples; Schloss et al. 2009). The sequence processing protocol partly followed the pipeline suggested by Schloss et al. (2011) and (Kozich et al. 2013). The paired sequences contained in reverse and forward fastq files were aligned into a contig. The resulted library was trimmed and screened to remove any mismatches with primer or DNA-tag sequences, ambiguous bases and homopolymers larger than 8 bp long. Sequences were aligned using Mothur version of SILVA bacterial reference sequences (version 102; Pruesse et al. 2007) and the sequences which were not aligned to a reference alignment of the correct sequencing region were removed. The samples having more than 20 000 sequences were rarefied to 20 000 sequences. At this point of sequence processing, the samples having less than 20 000 sequences were retained without rarefying. Unique sequences and their frequency in each sample were identified, and then, almost identical sequences (>99% similar) were preclustered to minimize sequencing errors (Huse et al. 2010) and screened for chimeras (UCHIME, Edgar et al. 2011) using the abundant sequences as a reference. The chimeric sequences were removed. The sequences were classified using Mothur version of Bayesian classifier (Wang et al. 2007) with the RDP training set version 9 (Cole et al 2009). Sequences that were classified as Mitochondria, Chloroplast, Archaea, Eukaryota or unknown were removed. Operational taxonomic units (OTUs) were assigned at 97% identity. Rare OTUs that were represented with 10 or fewer sequences in the whole data were removed. Some contamination was evident based on controls and thus the samples were adjusted based on the number sequences in each OTU that were found in controls. This was done by taking into account the initial rarefaction to 20 000 sequences of some samples. First, the sample wise proportions for each OTU were calculated. Second, the expected number of sequences for each OTU without the initial rarefaction was calculated using the proportions and the total number of sequences in each sample prior the initial subsampling. Third, for each OTU the number of sequences detected in control was subtracted from the samples and negative values were changed to zeros. Fourth, the proportion of sequences removed from each sample was detected and this proportion of sequences was removed from the data. Finally, all the samples were rarefied to 2000 sequences which is a compromise to have adequate number of sequences but not to lose too many samples. Three mineral soil samples had fewer number of sequences and were thus removed in this stage.

Results

TABLE 3

Number of OTUs i.e. bacterial richness was the highest in immunomodulatory compositions and the lowest in mineral soils. Materials derived from nature and natural forest soil had higher values than mineral soil, but most of them were lower than in immunomodulatory compositions. N = number of samples.

| | | Number of OTUs | | | |
|---|---|---|---|---|---|
| | N | Min | Max | Mean | StdDev |
| Freeze dried immunomodulatory composition | 3 | 436 | 485 | 462 | 25 |
| Sieved immunomodulatory composition | 8 | 303 | 413 | 361 | 38 |
| Organic soil - coniferous | 7 | 194 | 377 | 297 | 66 |
| Organic soil - non coniferous | 7 | 234 | 431 | 295 | 75 |
| Organic raw material | 7 | 173 | 270 | 226 | 40 |
| Moss | 3 | 173 | 270 | 229 | 50 |
| Peat | 2 | 216 | 239 | 228 | 16 |
| Wood mulch | 2 | 174 | 268 | 221 | 66 |
| Natural forest soil | 2 | 201 | 248 | 225 | 33 |
| Mineral soil-aggregate producer | 2 | 111 | 115 | 113 | 3 |

TABLE 4

Bacterial diversity measured as Shannon diversity index was the highest in immunomodulatory compositions and the lowest in mineral soils. Materials derived from nature and natural forest soil had higher values than mineral soil, but most of them were lower than in immunomodulatory compositions. N = number of samples.

| | | Shannon diversity index | | | |
|---|---|---|---|---|---|
| | N | Min | Max | Mean | StdDev |
| Freeze dried immunomodulatory composition | 3 | 5.13 | 5.32 | 5.23 | 0.09 |
| Sieved immunomodulatory composition | 8 | 4.26 | 4.96 | 4.66 | 0.22 |
| Organic soil - non coniferous | 7 | 3.81 | 5.04 | 4.28 | 0.46 |
| Organic soil - coniferous | 7 | 3.27 | 4.88 | 4.18 | 0.58 |
| Natural forest soil | 2 | 3.42 | 3.86 | 3.64 | 0.31 |
| Organic raw material | 7 | 2.51 | 4.13 | 3.55 | 0.57 |
| Moss | 3 | 3.23 | 4.05 | 3.73 | 0.44 |
| Peat | 2 | 3.41 | 3.64 | 3.52 | 0.16 |
| Wood mulch | 2 | 2.51 | 4.13 | 3.32 | 1.14 |
| Mineral soil - aggregate producer | 2 | 2.00 | 2.23 | 2.11 | 0.16 |

TABLE 5

Number of 16S copies i.e. bacterial abundance was the highest in immunomodulatory compositions and some organic soil materials and the lowest in mineral soils. N = number of samples.

| | | Number of 16S copies / g ww | | | |
|---|---|---|---|---|---|
| | N | Min | Max | Mean | StdDev |
| Organic soil - non coniferous | 7 | 2266053616 | 11597309791 | 6500195142 | 3477329482 |
| Sieved immunomodulatory composition | 8 | 2973155588 | 8992822967 | 5523895583 | 2344838596 |
| Natural forest soil | 2 | 4251867322 | 4859912127 | 4555889725 | 429952605 |
| Freeze dried immunomodulatory composition | 6 | 2258383975 | 4298476160 | 3462470836 | 820174162 |
| Sequencedsamples | 3 | 2258383975 | 3817652251 | 3203707982 | 830776015 |
| Other samples | 3 | 2697259440 | 4298476160 | 3721233691 | 889185419 |
| Organic raw material | 7 | 2735331 | 8843828910 | 1874346153 | 3450616262 |
| Moss | 3 | 834284072 | 8843828910 | 3656248947 | 4498366725 |
| Peat | 2 | 134146375 | 140448369 | 137297372 | 4456183 |
| Wood mulch | 2 | 2735331 | 2735331 | 2735331 | — |
| Organic soil - coniferous | 7 | 472000000 | 2356536589 | 1571529885 | 646043086 |
| Mineral soil - aggregate producer | 5 | 22064 | 699967 | 179643 | 292351 |
| Sieved immunomodulatory composition - neg. control | 1 | 16436 | 16436 | 16436 | — |
| Freeze dried neg. Control | 1 | 24640 | 24640 | 24640 | — |
| Mineral soil neg. Control | 1 | 9706 | 9706 | 9706 | — |

As evidenced in Tables 3-5, microbial richness i.e. number of OTUs, diversity i.e. Shannon index and abundance i.e. number of 16S copies are higher in immunomodulatory compositions than commercially available mineral soil materials designed for urban planning. The technical effect is that immunomodulatory compositions—if used as defined in the embodiments of the current invention—increase microbial richness, diversity and abundance of a subject, preferably a human subject in urban environment. Hence, immunomodulatory composition according to the current invention had high microbial richness, diversity and abundance, which is beneficial to prevent or treat immune mediated disorders and to activate immune system in a beneficial way. Importantly, mean diversity, richness and abundance in mineral soils from aggregate producer are lower than in claims 1-2. As these and similar materials are commonly used in the living environment of urban subjects, the technical effect of the immunomodulatory compositions is that they change microbiota of urban subjects.

Example 5—Testing Viral and Protozoan Pathogens in Soil Samples

Methods

Immunomodulatory compositions presented in examples 1 and 2 were tested for viral and protozoan pathogens by Q-PCR. Samples were extracted by PowerSoil DNA Isolation Kit or PowerSoil Total RNA Isolation Kit. Samples were tested for enterovirus, rhinovirus, rotavirus, norovirus, *Giardia* and *Cryptosporidium* by Q-PCR as described in (Krogvold et al., 2015) Cut-off limit for positive sample was less than 42 Ct-value. Validity of Q-PCR tests was monitored by spiking known amount of target RNA in the samples. Spiked samples were analyzed by Q-PCR and results were compared to positive control.

Results and Interpretation

All samples were negative for tested viruses and parasites. The result indicates that used manufacture procedures produce material safe for use since it is free of studied viral and protozoan human pathogens.

Example 6—*Pseudomonas* Pathogens

The sieved immunomodulatory composition described in example 2 and the freeze dried immunomodulatory composition described in example 3 were tested for the presence of *Pseudomonas aeruginosa* with a selective medium containing cetrimide (0.3 g/L). Cetrimide agar is commonly and successfully used as a selective medium for the isolation of *Pseudomonas aeruginosa* from various sources as only this species of *Pseudomonas* is capable of producing fluorescein and pyocyanin pigments when grown on cetrimide. In other words, while *Pseudomonas aeruginosa* forms blue colonies, other species of *Pseudomonas* from white colonies. Bacteria that do not belong to *Pseudomonas* are inhibited by the presence of cetrimide on the growth medium.

Test material dilutions, plating and incubation:

Ten grams of the sieved immunomodulatory composition was weighed into 95 ml of milliQ water, and the mixture was shaken vigorously for few minutes (dilution $A=10^{-1}$). From this a dilution series of 4 dilutions ($B=10^{-2}, C=10^{-3}, D=10^{-4}$, and $E=10^{-5}$) were made by measuring 9 ml of milliQ water into 15 ml Falcon tube and adding 1 ml of previous dilution to the tube thus giving a 100 fold dilution in each step. Each dilution was vortexed for few seconds and 100 μL was plated on a cetrimide plate (Sigma cat #22470) using a standard sterile technique. Three replicates of each dilution were plated.

The freeze dried immunomodulatory composition was dissolved in ~45 ml of milliQ water and vortexed lightly into a homogenous suspension. This was centrifuged for 5 minutes (50×g), and the supernatant was filtered with a 10 μM filter (Whatman cyclopore track etched membrane cat #7060-4715). The filtered immunomodulatory composition was then diluted and plated as described above.

A part of the filtered immunomodulatory composition was further processed via heat-inactivation, i.e. the suspension was boiled on a hot plate for 5 minutes. The evaporated water was then replaced (with milliQ water) to make the suspension up to the initial volume. This was then diluted and plated as described above.

The plates were incubated away from light at 30° C. for 18 hours and then another 24 hours at room temperature (22° C.).

Results:

After the incubation period, no visible colonies were observed on any plate containing filtered or heat-inactivated immunomodulatory compositions. Similarly, no colonies grew on the cetrimide agar plated with sieved immunomodulatory composition dilutions B-E. On the plate containing the dilution A of the sieved immunomodulatory composition there were few white colonies, but their colour and appearance were not those of *Pseudomonas aeruginosa* colonies but colonies of another species of *Pseudomonas*.

The technical effect is that the immunomodulatory compositions are free of *Pseudomonas aeruginosa*. Hence, the immunomodulatory compositions can be used without a risk of *Pseudomonas aeruginosa* infection.

Example 7: Potential Bacterial Pathogens in Illumina Sequencing

Methods

Sampling, Sample Preparation and Sequence Processing

Here we compared freeze dried immunomodulatory composition (3 samples) to mineral soil samples from soil aggregate producer (5 samples), to mineral soils from daycare yards (6 samples) and to natural forest samples (2 samples). Samples from soil aggregate producer, from daycare yard and from natural forest soil represent a normal environment that urban people encounter in their everyday life.

Mineral soil samples were collected from playgrounds of 3 daycare centers in the city center in Lahti, Finland. Altogether 6 samples from yards of the daycare centers were collected. Surface soil (depth 1-2 cm) was collected. At each of the three daycare yards, the first sample was taken from a sandbox. The second sample was taken from other site with mineral soil, such as under a swing set. For each sample, three ca. 2 g subsamples were collected, pooled and mixed thoroughly. Distance between subsampling points was at least 30 cm.

The sampling of other sample types, sample preparation and sequence processing of these samples has been described in example 4. However, here we used genus level data i.e. the OTUs were assigned to genera. During the sequence processing in Mothur, the sequences were classified using the Mothur version of Bayesian classifier (Wang et al. 2007) with the RDP training set version 9 (Cole et al 2009) and a consensus taxonomy for each OTU was generated. Then, the number of sequences in each OTU that had been classified into same genus were summed. Additionally, we used data that was processed in three different ways. First, we used data that was subsampled (rarefied) to 2000 sequences as was also used in example 4. Three mineral soil samples from soil aggregate producer had less than 2000 sequences and thus were not included in this comparison, but these samples were included in the other two data variants. Second, we used this same data without subsampling. And third, we used the unsubsampled data and converted it to relative abundances (i.e. number of sequences was divided with total number of sequences in a sample and multiplied with 100 to provide percentage frequency of each genus in each sample). Unsubsampled data was used because subsampling can remove some rare OTUs belonging to potentially pathogenic genera.

Data Processing

We first inspected the minimum, maximum, mean and standard deviation in each of the four groups of samples for nine genera that include pathogenic species. These were *Acinetobacter*, *Bacillus*, *Lactobacillus*, *Mycobacterium*, *Neisseria*, *Nocardia*, *Pseudomonas*, *Sphingomonas* and *Streptococcus*.

Then, we picked all the genera that have been listed to include potentially pathogenic species in Taylor et al. (2001) appendix A. We counted the abundance i.e. the sum of the number of sequences in each genera. Then we counted the minimum, maximum, mean and standard deviation in each of the four groups of samples.

Results

The mean and maximum of the abundance of each of the selected genera was always lower or equal in freeze dried immunomodulatory composition compared to the three other sample groups that represent the normal environment that urban people encounter in their everyday life (Tables 6-8). The abundance of potentially pathogenic genera, measured as 16S copies, was low in the immunomodulatory composition no matter if the data was subsampled (Table 6), non-subsampled (Table 7) or relative abundance data was compared (Table 8). This supports the view that the immunomodulatory composition is safer to handle than mineral soil at daycare yards, and safer or equally safe as commercial mineral soil products.

Altogether 34 genera of all the 136 genera listed in Taylor et al. (2001) were found in the whole data. Mineral soil samples from daycare yard had the highest number (i.e. 23) of potentially pathogenic genera (Table 9). Also samples from soil aggregate producer included more (i.e. 19) genera than freeze dried immunomodulatory composition and natural forest soil which had 15 and 14 genera, respectively. None of the genera were unique to freeze dried immunomodulatory composition meaning that if a genus was found from freeze dried immunomodulatory composition, it was also found from one of the reference samples that represent the normal environment that urban people encounter in their everyday life.

When all the sequences that belong to the potentially pathogenic genera listed in Taylor et al. (2001) were summed, the mean and maximum values were lower in the freeze dried immunomodulatory composition than mineral soil at daycare yards and this result was robust for data management type (Table 9). Also when considering relative abundances, mineral soils samples from aggregate producer had higher amount of sequences belonging to potentially pathogenic genera. Noteworhily, as evidenced in Table 9, the between-sample variability is virtually missing in the total number of potentially pathogenic bacterial 16 S sequences.

As seen in Tables 6-8, the abundance and relative abundance of *Lactobacillus*, *Mycobacterium* and *Acinetobacter* are low in the immunomodulatory composition. This means that the beneficial strains isolated in those genera cannot be the reason for the strong immunoregulatory response evidenced in the example 3. The technical effect is that the strong immunoregulatory response is caused by the immunomodulatory composition comprising non-culturable microbial community as described in the current invention.

The technical effects of the findings are that the immunomodulatory compositions according to the present invention are safe to use, partially because their quality is homogeneous. Importantly, the immunomodulatory composition did not contain any potentially pathogenic genera that were not present in everyday urban living environment. Because the richness and diversity of non-pathogenic genera are exceptionally high in the immunomodulatory composition (Example 4), another technical effect is that the immunomodulatory compositions according to the present invention expose urban subjects to rich microbial community without an additional risk of infections. This decreases the abundance of immune mediated disorders.

TABLE 6

Number of sequences of potentially pathogenic genera detected in samples of freeze dried immunomodulatory composition, mineral soils from aggregate producers, surface mineral soils from daycare yards and natural forest soils. Subsampling was done to 2000 sequences.

| | Acinetobacter | Bacillus | Lactobacillus | Mycobacterium | Neisseria | Nocardia | Pseudomonas | Sphingomonas | Streptococcus |
|---|---|---|---|---|---|---|---|---|---|
| *Data: adjusted for control, subsampled to 2000* | | | | | | | | | |
| *Freeze dried immunomodulatory composition (n = 3)* | | | | | | | | | |
| Min | 2 | 0 | 0 | 1 | 0 | 0 | 1 | 14 | 0 |
| Max | 4 | 0 | 1 | 2 | 0 | 0 | 11 | 19 | 0 |
| Mean | 3 | 0 | 0 | 1 | 0 | 0 | 6 | 17 | 0 |
| St Dev | 1 | 0 | 1 | 1 | 0 | 0 | 5 | 3 | 0 |
| *Mineral soil - aggregate producer (n = 2)* | | | | | | | | | |
| Min | 1 | 0 | 0 | 0 | 0 | 0 | 7 | 7 | 0 |
| Max | 2 | 0 | 1 | 1 | 0 | 0 | 16 | 9 | 2 |
| Mean | 2 | 0 | 1 | 1 | 0 | 0 | 12 | 8 | 1 |
| St Dev | 1 | 0 | 1 | 1 | 0 | 0 | 6 | 1 | 1 |
| *Mineral soil - daycare yard (n = 6)* | | | | | | | | | |
| Min | 2 | 0 | 0 | 5 | 0 | 0 | 3 | 50 | 0 |
| Max | 9 | 0 | 1 | 15 | 0 | 0 | 28 | 125 | 0 |
| Mean | 4 | 0 | 0 | 10 | 0 | 0 | 16 | 83 | 0 |
| St Dev | 3 | 0 | 1 | 4 | 0 | 0 | 10 | 28 | 0 |
| *Natural forest soil (n = 2)* | | | | | | | | | |
| Min | 0 | 0 | 0 | 3 | 0 | 0 | 0 | 0 | 0 |
| Max | 6 | 0 | 0 | 33 | 0 | 1 | 6 | 1 | 0 |
| Mean | 3 | 0 | 0 | 18 | 0 | 1 | 3 | 1 | 0 |
| St Dev | 4 | 0 | 0 | 21 | 0 | 1 | 4 | 1 | 0 |

TABLE 7

Number of sequences of potentially pathogenic genera detected in samples of freeze dried immunomodulatory composition, mineral soils from aggregate producers, surface mineral soils from daycare yards and natural forest soils. No subsampling.

| | Acinetobacter | Bacillus | Lactobacillus | Mycobacterium | Neisseria | Nocardia | Pseudomonas | Sphingomonas | Streptococcus |
|---|---|---|---|---|---|---|---|---|---|
| *Data: adjusted for control, unsubsampled* | | | | | | | | | |
| *Freeze dried immunomodulatory composition (n = 3)* | | | | | | | | | |
| Min | 5 | 0 | 0 | 12 | 0 | 0 | 3 | 99 | 0 |
| Max | 19 | 0 | 2 | 15 | 0 | 0 | 7 | 134 | 1 |
| Mean | 13 | 0 | 1 | 14 | 0 | 0 | 5 | 111 | 0 |
| St Dev | 7 | 0 | 1 | 2 | 0 | 0 | 2 | 20 | 1 |
| *Mineral soil - aggregate producer (n = 5)* | | | | | | | | | |
| Min | 0 | 0 | 0 | 0 | 0 | 0 | 0 | 5 | 0 |
| Max | 9 | 0 | 3 | 5 | 0 | 0 | 22 | 192 | 10 |
| Mean | 3 | 0 | 1 | 1 | 0 | 0 | 6 | 55 | 2 |
| St Dev | 4 | 0 | 1 | 2 | 0 | 0 | 9 | 78 | 4 |
| *Mineral soil - daycare yard (n = 6)* | | | | | | | | | |
| Min | 5 | 0 | 0 | 38 | 0 | 0 | 9 | 363 | 0 |
| Max | 56 | 0 | 1 | 92 | 1 | 1 | 56 | 969 | 1 |
| Mean | 27 | 0 | 1 | 60 | 0 | 0 | 31 | 594 | 0 |
| St Dev | 20 | 0 | 0 | 23 | 0 | 0 | 21 | 230 | 1 |
| *Natural forest soil (n = 2)* | | | | | | | | | |
| Min | 0 | 0 | 0 | 38 | 0 | 0 | 0 | 0 | 0 |
| Max | 21 | 0 | 0 | 249 | 0 | 15 | 0 | 1 | 0 |
| Mean | 11 | 0 | 0 | 144 | 0 | 8 | 0 | 1 | 0 |
| St Dev | 15 | 0 | 0 | 149 | 0 | 11 | 0 | 1 | 0 |

TABLE 8

Relative number of sequences of potentially pathogenic genera detected in samples of freeze dried immunomodulatory composition, mineral soils from aggregate producers, surface mineral soils from daycare yards and natural forest soils. No subsampling.

Data: adjusted for control, relative abundances

| | Acinetobacter | Bacillus | Lactobacillus | Mycobacterium | Neisseria | Nocardia | Pseudomonas | Sphingomonas | Streptococcus |
|---|---|---|---|---|---|---|---|---|---|
| Freeze dried immunomodulatory composition (n = 3) | | | | | | | | | |
| Min | 0.0 | 0.0 | 0.0 | 0.1 | 0.0 | 0.0 | 0.1 | 0.7 | 0.0 |
| Max | 0.1 | 0.0 | 0.0 | 0.1 | 0.0 | 0.0 | 0.4 | 1.0 | 0.0 |
| Mean | 0.1 | 0.0 | 0.0 | 0.1 | 0.0 | 0.0 | 0.3 | 0.8 | 0.0 |
| St Dev | 0.1 | 0.0 | 0.0 | 0.0 | 0.0 | 0.0 | 0.1 | 0.2 | 0.0 |
| Mineral soil - aggregate producer (n = 5) | | | | | | | | | |
| Min | 0.0 | 0.0 | 0.0 | 0.0 | 0.0 | 0.0 | 0.0 | 0.3 | 0.0 |
| Max | 0.1 | 0.0 | 0.3 | 0.0 | 0.0 | 0.0 | 0.6 | 9.7 | 0.1 |
| Mean | 0.0 | 0.0 | 0.1 | 0.0 | 0.0 | 0.0 | 0.2 | 2.7 | 0.0 |
| St Dev | 0.0 | 0.0 | 0.1 | 0.0 | 0.0 | 0.0 | 0.3 | 4.0 | 0.0 |
| Mineral soil - daycare yard (n = 6) | | | | | | | | | |
| Min | 0.0 | 0.0 | 0.0 | 0.3 | 0.0 | 0.0 | 0.1 | 3.1 | 0.0 |
| Max | 0.4 | 0.0 | 0.0 | 0.6 | 0.0 | 0.0 | 1.3 | 6.5 | 0.0 |
| Mean | 0.2 | 0.0 | 0.0 | 0.4 | 0.0 | 0.0 | 0.7 | 4.2 | 0.0 |
| St Dev | 0.1 | 0.0 | 0.0 | 0.1 | 0.0 | 0.0 | 0.5 | 1.3 | 0.0 |
| Natural forest soil (n = 2) | | | | | | | | | |
| Min | 0.0 | 0.0 | 0.0 | 0.3 | 0.0 | 0.0 | 0.0 | 0.0 | 0.0 |
| Max | 0.2 | 0.0 | 0.0 | 1.7 | 0.0 | 0.1 | 0.4 | 0.0 | 0.0 |
| Mean | 0.1 | 0.0 | 0.0 | 1.0 | 0.0 | 0.1 | 0.2 | 0.0 | 0.0 |
| St Dev | 0.1 | 0.0 | 0.0 | 1.0 | 0.0 | 0.1 | 0.3 | 0.0 | 0.0 |

TABLE 9

Sum of sequences of potentially pathogenic bacteria detected in samples of freeze dried immunomodulatory composition, mineral soils from aggregate producers, surface mineral soils from daycare yards and natural forest soils. Results based on unsubsampled and subsampled data as well as relative abundance data are shown. Also the number of potentially pathogenic genera is shown.

| | Number of sequences in potentially pathogenic genera | | | | Number of potentially pathogenic genera |
|---|---|---|---|---|---|
| Data: adjusted for control, unsubsampled | | | | | |
| | Mean | Min | Max | StDev | |
| Freeze dried immunomodulatory composition | 317 | 303 | 341 | 21 | 15 |
| Mineral soil - aggregate producer | 115 | 7 | 217 | 103 | 19 |
| Mineral soil - daycare yard | 974 | 574 | 1350 | 281 | 23 |
| Natural forest soil | 223 | 166 | 279 | 80 | 14 |
| Data: adjusted for control, subsampled to 2000 | | | | | |
| | Mean | Min | Max | StDev | |
| Freeze dried immunomodulatory composition | 47 | 36 | 56 | 10 | |
| Mineral soil - aggregate producer | 30 | 30 | 30 | 0 | |
| Mineral soil - daycare yard | 141 | 108 | 175 | 29 | |
| Natural forest soil | 32 | 24 | 40 | 11 | |
| Data: adjusted for control, relative abundances | | | | | |
| | Mean | Min | Max | StdDev | |
| Freeze dried immunomodulatory composition | 2.4 | 2.3 | 2.4 | 0 | |
| Mineral soil - aggregate producer | 4.0 | 1.3 | 10.9 | 4 | |
| Mineral soil - daycare yard | 6.9 | 5.0 | 9.0 | 1 | |
| Natural forest soil | 1.6 | 1.2 | 1.9 | 1 | |

Example 8—Baby and Toddler Product Descriptions

Packets of Immunomodulatory Material

Figure 6:
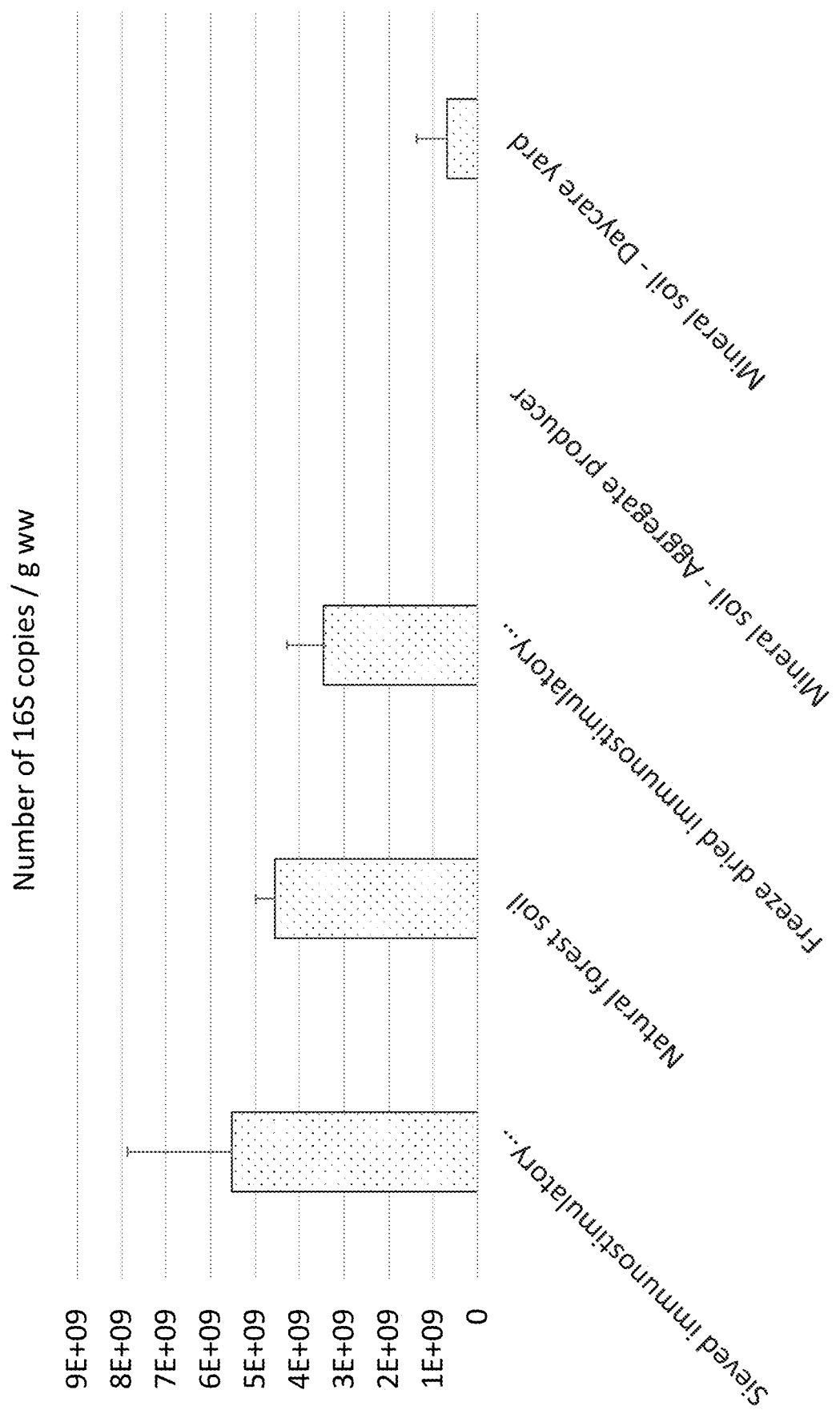
FIG. 6. Microbial abundance as indicated by number of 16 S sequences in the sieved immunomodulatory composition described in example 2, natural forest soils described in examples 4 and 7, freeze dried immunomodulatory composition described in example 3, commonly used mineral soil materials from aggregate producer described in examples 4 and 7, and mineral soils collected at urban daycare yards described in example 7. For microbial diversity, richness, pathogen levels and sampling details, see examples 2-7. Note that the values in Mineral soil—Aggregate producer are very low, and that those in Mineral soil—Daycare yard are lower than in natural forests and immunomodulatory compositions. The technical effect is that immunomodulatory compositions according to the current invention are suitable for modifying microbial communities of a subject.

Examples of the immunomodulatory compositions that can be used herein are dried and sieved moss (particle size less than 1 mm), sieved composition used in example 2 and freeze dried and inactivated immunomodulatory composition used in example 3. These materials are suitable for modifying skin microbial community as their microbial abundance, diversity and richness are high, and they do not contain sharp particles. An example of high microbial abundance of the immunomodulatory compositions is given in FIG. 6.

The packets containing immunomodulatory composition are made of a gossamer-like fabric. A layer of immunomodulatory composition is placed inside the packets, and they come in two sizes: 15×21 cm (A5) and 10×10 cm. The smaller packet has been tested for choking hazard with a test cylinder (small objects choke tester) provided by Tukes (Finnish Safety and Chemical Agency). According to the test, the packets do not pose a choking hazard. The smaller immunomodulatory packets are used as part of infant hats and security blankets. The bigger immunomodulatory packets are used with the other products. The thin permeable fabric of the packets allows the immunomodulatory components of the material pass through on the skin of the user. Thus, the microbial community on the skin changes as evidenced in example 9.

Infant Hat

The infant hat is made of cotton jersey, and inside its front (covering the forehead) there is a pocket for the immunomodulatory packet (10×10 cm). The size of the hat is 60-86 cm (3 months to 3 years), and it can be adjusted by tying the top end of the hat with a ribbon, hair elastic, or equivalent.

The immunomodulatory packet that is placed inside the hat has been tested for choking hazard with a choke tube tester by Tukes, and as a result no choking hazard exists. The immunomodulatory components of material are able to pass through the layers of fabric and thus act on the skin of the forehead as evidenced in example 9.

Figure 7:
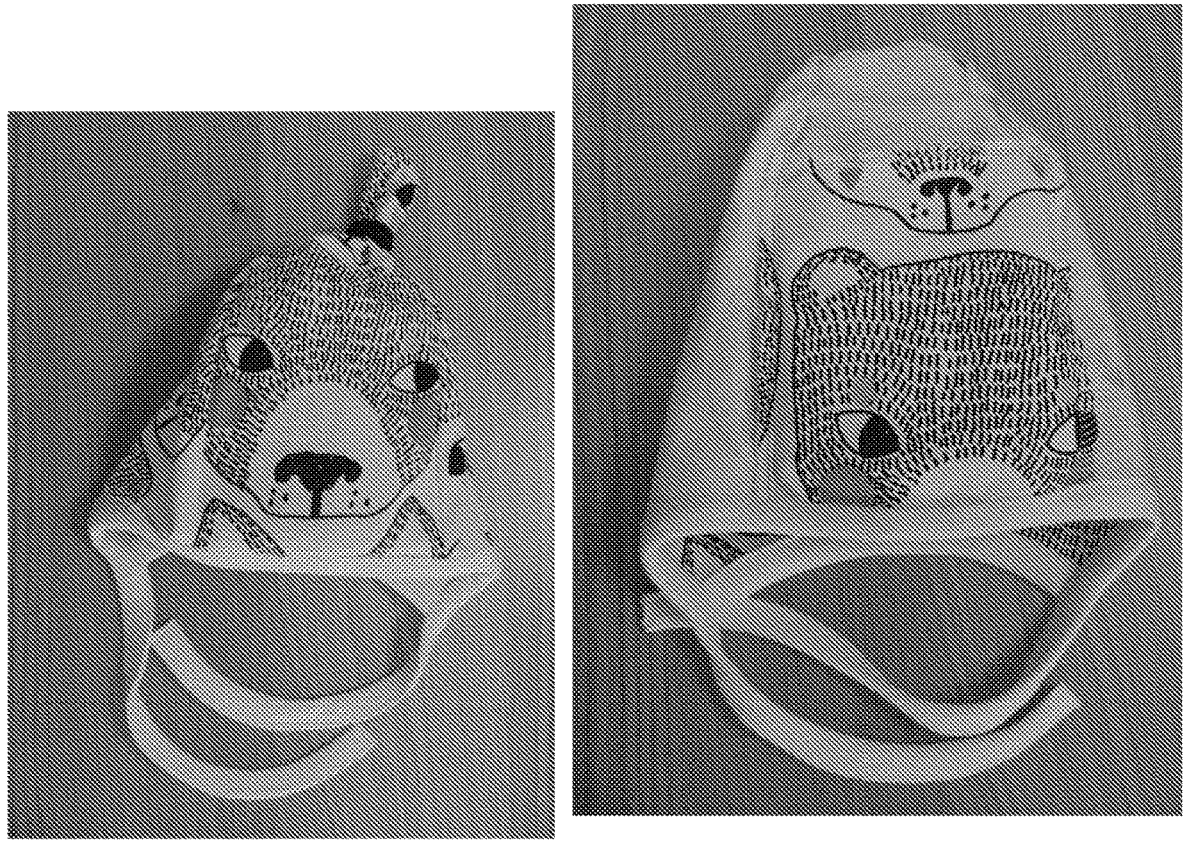
FIG. 7. Infant hat with tied top (left) and the same infant hat inside out (right). Note the pocket for the immunomodulatory packet. The technical effect is that forehead skin becomes in contact with small particles of immunomodulatory composition. This will in turn activate immunoregulatory mechanisms i.e. lead to a technical effect. This technical effect can partially also be produced by inhaling the immunomodulatory components while using the product.
Figure 8:
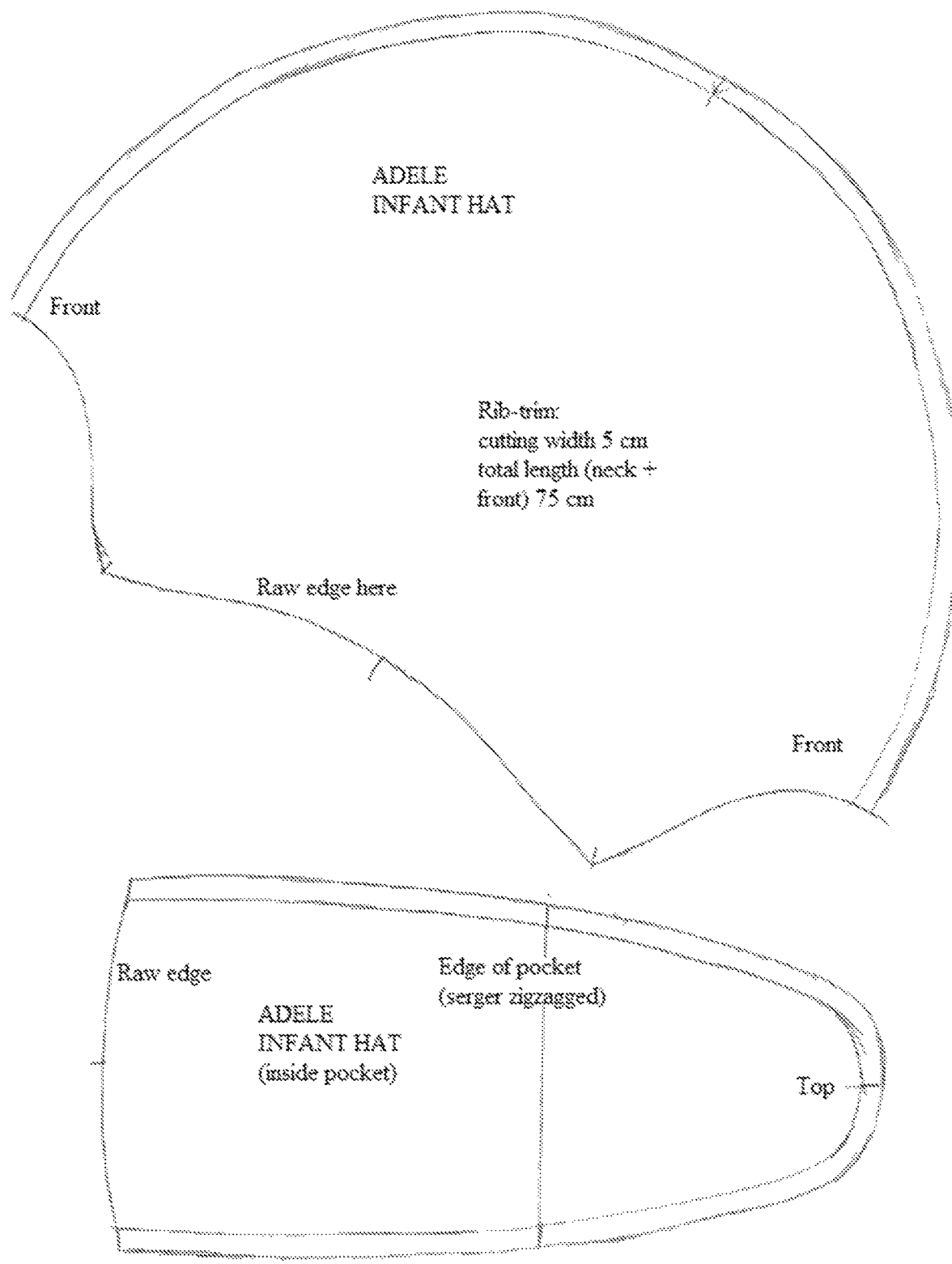
FIG. 8. Sketch of infant hat (not to scale) shown in FIG. 7.

Infant hat is illustrated in FIGS. 7 and 8. Technical effect is described in FIG. 7.

Building Blocks

Figure 9:
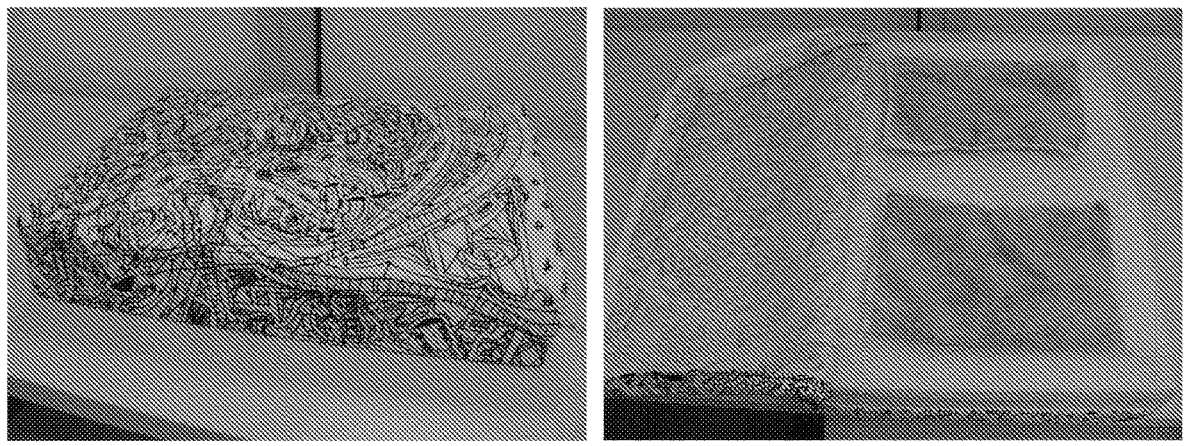
FIG. 9. Building block (left) and interior of building block (right). In interior, two packets of immunomodulatory composition are visible. Blocks enable the immunomodulatory components of the immunomodulatory material to scatter on and around the children while using the product. This will in turn activate immunoregulatory mechanisms i.e. lead to a technical effect. This technical effect can partially also be produced by inhaling the immunomodulatory components while using the product.

Another example of an article is in the form of foam building blocks covered with cotton fabric, and they are 7×37×50 cm in size. They are illustrated and the technical effect is described in FIG. 9. Children can safely climb on the blocks, lift up the blocks, and build with the blocks. These activities enable the immunomodulatory components of the immunomodulatory material to scatter on and around the children. This will in turn activate immunoregulatory mechanisms i.e. a technical effect. This technical effect can partially also be produced by inhaling the immunomodulatory components while using the product.

The fabric cover has a zipper, and four immunomodulatory packets (15×21 cm) can be placed inside the cover. The packets can be changed regularly or when advised.

The packets can only be removed by undoing the zipper on the cover. The cover is made of 100% cotton fabric. The cotton fabric used here has been certified according to Öko-Tex 100 standard in the product class I (the highest level of product class), but this certification is not necessary for the desired effect. The other fabric parameters are: 100% cotton, plain weave, average yarn number of 18.33, decitex measurement per single yarn is 500. The chemicals and dyes used for the making of the fabric are in accordance with the Reach regulation of the European Union.

Infant Security Blanket

Figure 10:
FIG. 10. Infant security blanket. Packet of immunomodulatory composition is within the top that is tied with a ribbon into a bundle. The infant security blankets have similar technical effects as the other products: the immunomodulatory component of the material passes through the fabric layers and reaches the skin activating immunoregulatory mechanisms. As with the other products, the technical effect can partially be caused by inhaling the immunomodulatory components while using the product.
Figure 11:
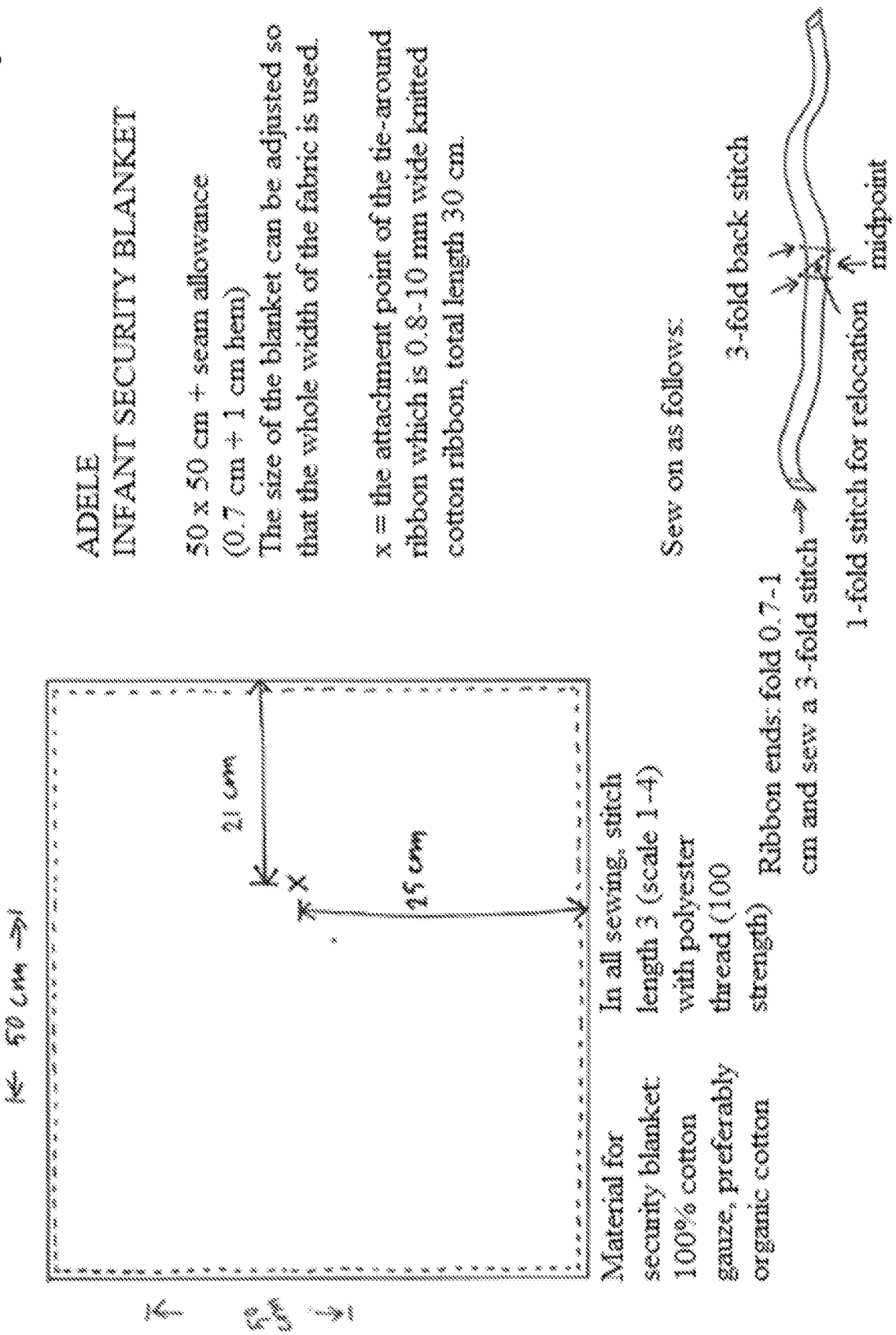
FIG. 11. Sketch of infant security blanket.

Another example of an article is an infant security blanket illustrated in FIG. 10 and FIG. 11. It is made of gauze-like cotton fabric, and it fulfills the above mentioned security standards. It is a square piece of fabric that is 50×50 cm in size. A 30 cm long cotton ribbon is sewn near the middle of the square, and the attachment point of the ribbon divides the ribbon into two equal lengths (=15 cm and 15 cm). This length was chosen because it will not pose a choking hazard. The piece of fabric is then folded in half, and the immunomodulatory packet (10×10 cm) is inserted in the middle and secured in place by tying the ends of the ribbon around the fabric.

The standards for safety of children's clothing or toys do not apply to infant security blankets. General provisions, however, require general consumer goods to be safe. The immunomodulatory packet placed inside the security blanket has been tested with the small objects choke tester provided by Tukes to exclude any choking hazard.

Pillow Case and Duvet Cover

Figure 12:
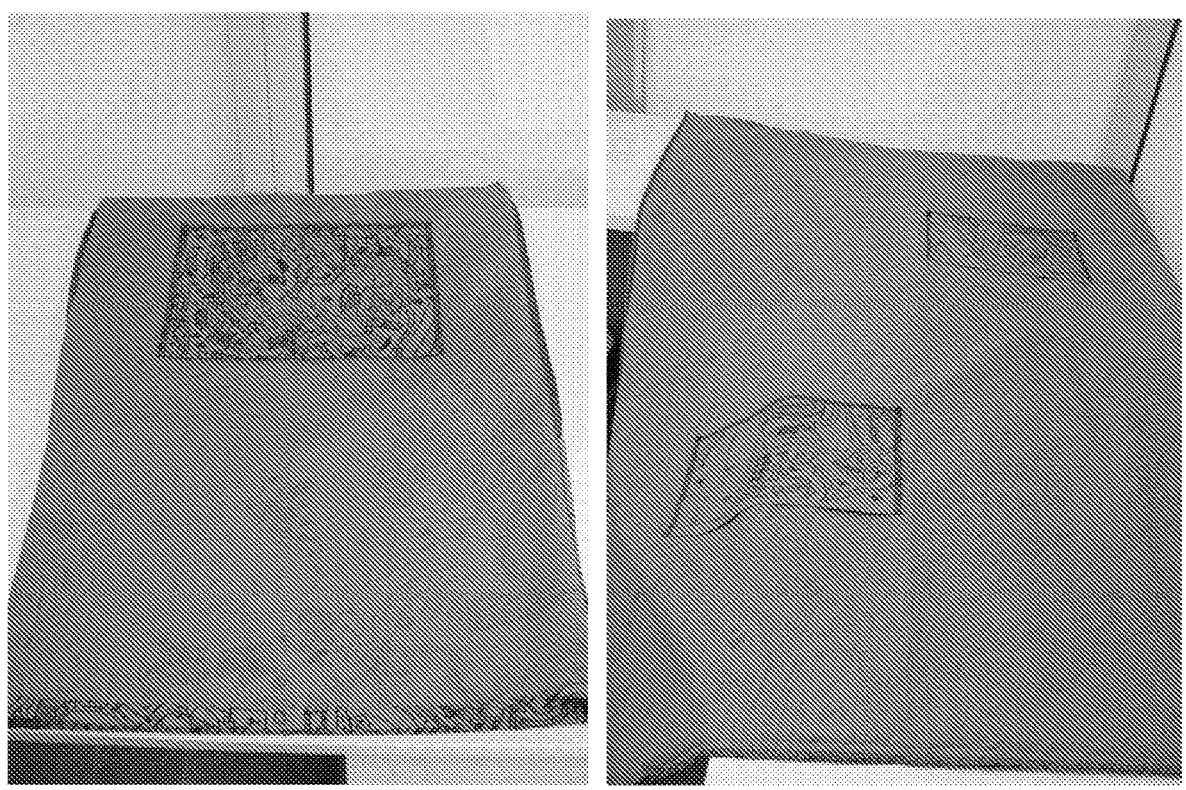
FIG. 12 Pillow case inside out (left) and duvet cover inside out (right). The technical effect of stimulating the immunoregulatory system here is analogous to the other products. The immunomodulatory component of the immunomodulatory composition passes through the layers of fabric and reaches the skin activating immunoregulatory mechanisms. Similar technical effect can, in part, also be triggered by the inhalation of the immunomodulatory components of the material while using the product.

The pillow case and the duvet cover are sized for children: the pillow case is 40×50 cm whereas the duvet cover is 80×115 cm. There are two and four pockets for the immunomodulatory packets inside the pillow case and the duvet cover, respectively. The pockets are sewn inside the covers, and they are A5 (15×21 cm) in size. The pockets are located on both sides of the inserted pillow or blanket, and they need to accessed from inside to remove the immunomodulatory packets as the packets are locked in place by the pocket folds. The pockets are as inconspicuous as possible for the user and should not cause any lumps or bulges on the surface of a pillow or a blanket. The pillow case and duvet cover are illustrated and their technical effect is described in FIG. 12.

Example 9. Skin Bacterial Composition Before and after Use of Immunomodulatory Composition Methods Testing the Packets and Sampling The immunomodulatory composition used herein was dried, crushed and mixed *Sphagnum* moss (particle size less than 1 mm). A layer of immunomodulatory composition was placed inside a fabric packet of size 10×10 cm. Three different types of fabrics were tested: airlaid material ST047DIA (thickness 0.44 mm), airlaid material DS100 (thickness 0.85 mm) and cotton fabric. Airlaid materials are used for manufacturing different kind of products such as table tops, napkins, and laboratory pads. Cotton fabric was the same material which was used in baby and toddler products described in example 8.

Two volunteers conducted the experiment. Both volunteers tested one packet made of ST047DIA and one packet made either of DS100 or cotton fabric. The packets were placed on the inner forearms of the volunteers. Packets were tied on with a clean disposable self-adhesive bandage. The volunteers were exposed to the packets for 3 hours and 45 minutes. Skin swabs (5×5 cm area, 10 seconds) were taken just before placing the packets and immediately after they were removed. A stick with a cotton wool tip was first wetted in Tween® 20, used in sampling and placed into a sterile polyethylene sample tube.

Bacterial composition on skin before and after use of the packets was compared to the bacterial composition in the Spagnum moss that was used as a raw material for the packets. The preparation of the moss sample is described in example 4.

Sample Preparation to MiSeq Sequencing for Skin Swab Samples

Skin swab samples were stored in deep freezer (<−70° C.) in tubes containing Tween 20 (MP Biomedicals) (0.1%)+ NaCl (0.1 M, J. T. Baker) before DNA extraction. Total DNA was extracted from samples using PowerSoil® DNA Isolation Kit (MoBio Laboratories, Inc., Carlsbad, Calif., USA) according to the manufacturer's standard protocol. The swab was transferred to the PowerBead tube for a homogenization and lysis procedure. DNA was checked with agarose gel (1.5%) electrophoresis (120 V, 30 min). Total DNA concentration was measured with Quant-iT™ PicoGreen® dsDNA reagent kit (Thermo scientific, MA, USA).

The V4 region within the 16S ribosomal RNA (rRNA) gene was amplified by primary PCR as triplicates using 505F and 806R primers (Caporaso et al. 2012). Primary PCR was carried out in a reaction mixture (reaction volume 50 µl) consisting of 1 µl each of 10 mM deoxynucleoside triphosphates (dNTPs; Thermo scientific, MA, USA) 5 µl forward primer 505F (10 µM; 5'-GTGCCAGC MGCCGCGGTAA-3') and 5 µl reverse primer 806R (10 µM; 5'-GGACTACHVGGGTWTCTAAT-3'), 0.5 µl 2 U/µl Phusion Green Hot Start II High-Fidelity DNA polymerase (Thermo scientific, MA, USA), 10 µl 5× Green HF PCR buffer (F-537), 5 µl template DNA and 23.5 µl sterile water. The PCR reaction was run in a thermocycler (MJ Research, MA, USA) as follows: initial denaturation at 98° C. for 5 min, followed by 30 cycles with denaturation at 94° C. for 1 min, annealing for 10 sec at 50° C. and extension for 1 min at 72° C., and then a final extension at 72° C. for 10 min. A positive control (*Cupriavidus necator* JMP134, DSM 4058) was included in PRC runs to ensure that the PCR worked, and a negative control (sterile water) was run to detect any possible contamination. DNA was detected with agarose gel (1.5%) electrophoresis (120 V, 1 h). The PCR products were purified using Agencourt AMPure XP solution (Beckman Coulter Ins.) to reduce carryover of primary PCR primers. Triplicates of the cleaned amplicons were pooled and diluted 1:5.

Cleaned and diluted primary PCR products were targeted in the secondary PCR (TagPCR). Reaction mixture to the TagPCR was equal as above except reverse primer included a 12 bp unique Multiplexing Identifier tag (MID-806R). Amplification program was the same as above except there were only seven cycles for soil products and ten cycles for other samples. TagPCR products were detected on agarose gel (1.5%) electrophoresis (120 V, 1 h), purified with Agencourt AM Pure, pooled and the DNA concentration was measured with PicoGreen. The sequencing was performed at the Kansas State University using Illumina MiSeq platform. The sequencing was performed using Illumina MiSeq platform with a 2×300 bp version 3 kit sequencing kit according to manufacturer's protocol. The GeneRead DNA Library I Core Kit (Qiagen, catalog #180432) was used to ligate Illumina's TruSeq adapters to amplicons.

Sequence Processing

Sequence data for skin swab samples and the moss sample were analyzed together using Mothur-program (version v.1.38.1; Schloss et al. 2009). The sequence processing protocol followed the same protocol described in example 4, with the exception that samples were processed unrarefied until the end of the protocol. For each OTU the number of sequences found in negative controls (extraction negative, per negative) were subtracted from each sample. The final OTU-table was rarefied to 2000 similarly as in example 4.

Data Analyses

Number of OTUs, Shannon diversity and Fisher's alpha were calculated using functions diversity, fisher.alpha and specnumber in R package vegan. Principal Coordinate Analysis (Gower 1966) was performed using cmdscale function in R package stats.

Results

Figure 13:
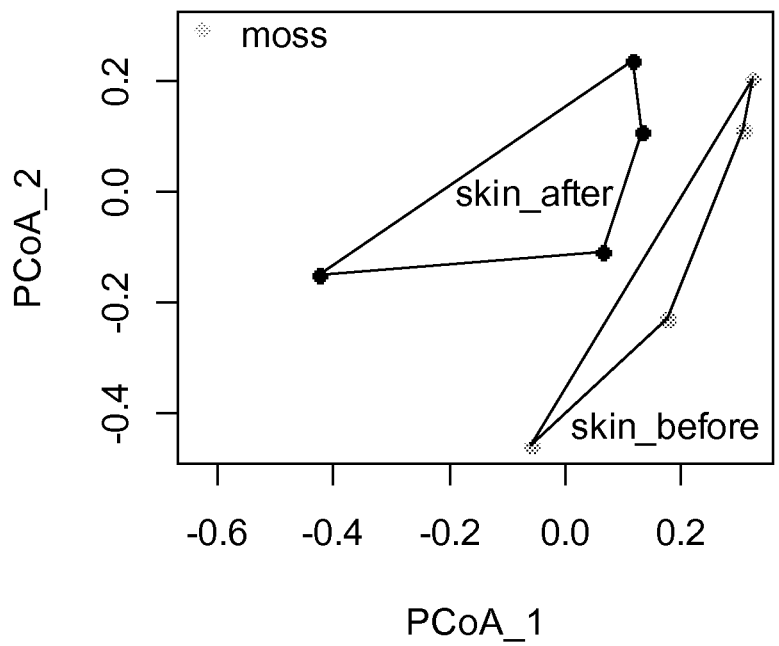
FIG. 13 shows the effect of a packet containing an immunomodulatory composition on skin microbial community. Skin swab samples before and after the use of packets filled with the immunomodulatory composition have different bacterial communities. Also the bacterial community composition of material derived from nature, i.e., non-processed *Sphagnum* moss is shown. For details of manufacturing the immunomodulatory composition, see Example 9. The ordination method is principal coordinate analysis. For abundance data, the variance explained by the first and second axes are 44.5% and 27.6%, respectively. For presence-absence data, the variance explained by the first and second axes are 37.7% and 18.0%, respectively. Figures visualize the technical effect how the use of the packets with immunomodulatory composition shifted the bacterial community composition on skin; changes in richness and diversity are shown in Table 10.
Figure 13:
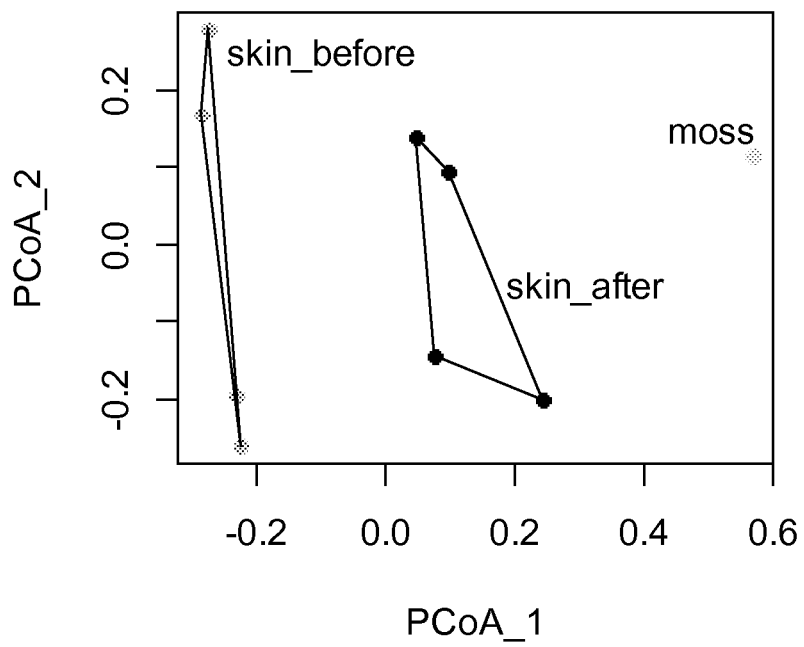
Figure 14:
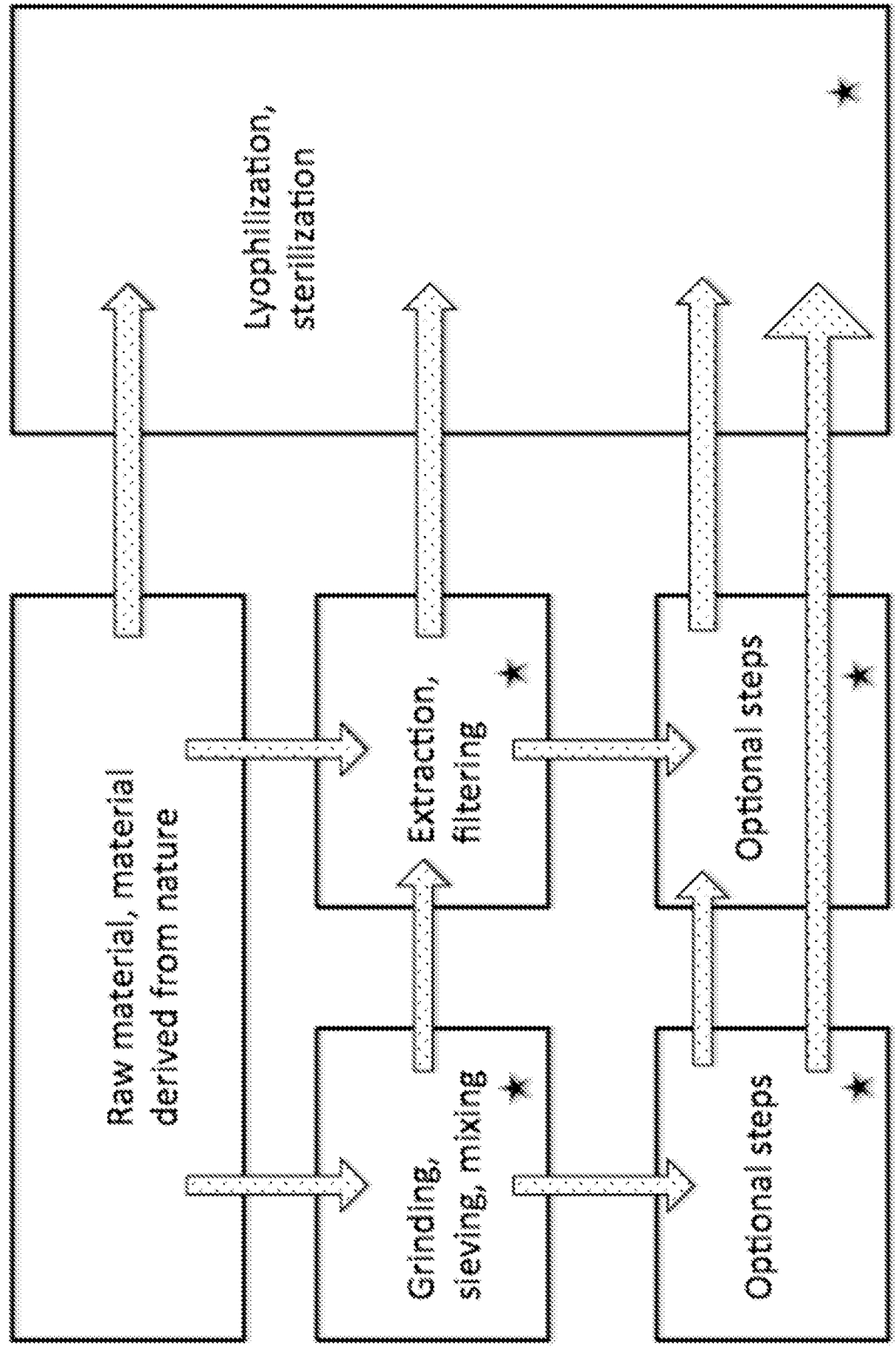
FIG. 14 is a flow diagram showing alternative processing pathways to manufacture the immunomodulatory composition from the material derived from nature as a raw material. Star denotes a step in which immunomodulatory composition can be recovered.

Bacterial richness, Shannon diversity index and Fisher alpha were always higher in samples taken after the use of packets containing immunomodulatory composition compared to the samples taken before the use, see Table 10. The bacterial community composition in skin swab samples was different, depending on whether the immunomodulatory composition was used or not, see FIG. 13. The technical effect is that the use of the immunomodulatory composition changes skin microbial community, e.g. it increases Shannon diversity index and bacterial richness.

TABLE 10

Bacterial richness (i.e. number of OTUs), Shannon diversity index i.e. Shannon index and Fisher alpha of skin swab samples taken before and after the use of packets filled with an immunomodulatory composition. Also the values for Spagnum moss used as raw material to manufacture the immunomodulatory composition are shown.

| Bag type | Sample | Number of OTUs | Shannon index | Fisher alpha |
|---|---|---|---|---|
| DS100 | Before | 123 | 2.74 | 28.94 |
| DS100 | After | 159 | 3.27 | 40.59 |
| Cotton fabric | Before | 85 | 2.62 | 18.01 |
| Cotton fabric | After | 142 | 3.59 | 34.93 |
| S1047DIA_1 | Before | 109 | 2.41 | 24.75 |
| S1047DIA_1 | After | 141 | 2.87 | 34.61 |
| S1047DIA_2 | Before | 103 | 2.90 | 23.01 |
| ST047DIA_2 | After | 136 | 3.27 | 33.00 |
| Moss | | 194 | 3.46 | 53.07 |

Example 10. Particle Size in the Sieved Immunomodulatory Composition

Sieved immunomodulatory composition was manufactured as described in example 2, e.g. Ø 5 mm and Ø 2 mm sieves were used. To find out particle sizes of the remaining particles, 50 g of soil mixture was dried overnight (~18 hrs) at 70° C. Weight after drying was 26.48 g. This was sieved through 5 sieves with Retsch AS 200 analytical sieve shaker with amplitude of 50 s-1 for 10 minutes. The results show that >50% or particles were smaller than Ø (Table 11). Together with the results of the previous examples, the technical effect is that sieving is suitable for manufacturing immunomodulatory compositions that are safe and effective.

TABLE 11

Aperture size of particles in the sieved immunomodulatory mixture.

| aperture size (micron) | sieve weight (g) | total weight after sieving (g) | soil on sieve (g) | % |
|---|---|---|---|---|
| 1000 | 304.32 | 316.57 | 12.25 | 46.3 |
| 500 | 305.5 | 311.43 | 5.93 | 22.4 |
| 250 | 281.82 | 286.06 | 4.24 | 16.0 |
| 125 | 263.79 | 265.89 | 2.1 | 7.9 |
| 63 | 251.4 | 252.42 | 1.02 | 3.9 |
| collecting pan | 353.66 | 354.6 | 0.94 | 3.5 |

Example 11

The experimental setup of example 2 was followed. In short, seven healthy adults that live in urban conditions were in control group that continued normal life. At the same time, 7 healthy adults that live in urban conditions were in an exposure group that "washed" their hands with an immunomodulatory preparation 3 times a day for two weeks. Otherwise also the exposure group lived normal life. The immunomodulatory preparation is described in example 2. Stool microbiota was sampled and analyzed as in experiment 2, in the beginning and in the end of the experiment. Skin microbiota was sampled and analyzed similarly to example 1, in the beginning and in the end of the experiment. The skin microbial sample was always taken from the forearm, while only palms and fingers were exposed to the immunomodulatory material.

We compared the change in microbial diversity in the exposure group to the expression of an immunoregulatory cytokines (TGF-beta) in peripheral blood mononuclear cells (PBMCs) at the end of the exposure period. The change in both in skin and stool microbial diversity was associated with TGF-beta expression ($R2=0.971$, $p=0.001$).

The results show that the immunomodulatory material described in this invention causes an immunomodulatory effect according to the current invention.

Without limiting the scope and interpretation of the patent claims, certain technical effects of one or more of the aspects embodiments disclosed herein are listed in the following: A technical effect is increased microbial diversity on or in a human or animal subject. A technical effect is increased microbial richness on or in a human or animal subject. A technical effect is increased microbial abundance on or in a human or animal subject. A technical effect is induced IL-10 expression on or in a human or animal subject. A technical effect is altered IFN-gamma expression on or in a human or animal subject. These five technical effects are shown in examples 1-3.

A technical effect of wearing or playing or otherwise being in contact with an immunomodulatory product is increased microbial diversity, richness and/or abundance as evidenced in examples 8-9 and 1-3.

A technical effect of immunomodulatory compositions obtainable by processing material derived from nature is more comfortable texture and feel of the immunomodulatory composition; natural materials, particularly soil and plant parts, have particles with sharp edges that can hurt. These sharp edged particles are removed in e.g. sieving, as in examples 2 and 10.

A technical effect of modification of material derived from nature is high diversity, richness and abundance or non-culturable microbes in immunomodulatory compositions, as evidenced in example 4.

A technical effect of freeze drying or sterilization is reduced or missing activity of pathogens. The modifications, however, still facilitate the immunostimulation by immunomodulatory compositions, as evidenced in example 3.

A technical effect of sieving and many other modifications described above is reduced heterogeneity of material derived from nature, as shown in example 7. In heterogeneous materials, patches of single microbial strains are likely, which allows high abundance of pathogenic OTUs. Another technical effect is absence or low abundance of pathogenic microbes, as evidence in examples 5-7. Pathogenic microbes in natural materials, such as soil, are the reason why soil and other natural products are not safe be used as such to modulate immune system.

A technical effect of several modifications, e.g. sieving and filtering, is non-existing risk of multicellular parasites such as lice and ticks, because these are too large to pass sieving, filtering, or unable to survive in sterilization or evaporation.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

REFERENCES

Anderson M J (2001) A new method for non-parametric multivariate analysis of variance. Austral Ecol 26: 32-46.
Bakken J S (2009) Fecal bacteriotherapy for recurrent *Clostridium difficile* infection. Anaerobe 15: 285-289. doi: 10.1016/j.anaerobe.2009.09.007.
Berry D, Mahfoudh K B, WagnerM, et al. (2011) Barcoded primers used in multiplex amplicon py-rosequencing bias amplification. Appl Environ Microb 77: 7846-9.
Caporaso, J. G., Kuczynski, J., Stombaugh, J., Bittinger, K., Bushman, F. D., Costello, E. K., . . . Knight, R. (2010). QIIME allows analysis of high-throughput community sequencing data. Nature Methods, 7(5), 335-6. http://doi.org/10.1038/nmeth.f.303
Cinek, Ondrej, & et al. (2016). Imbalance of bacteriome profiles within the Finnish DIPP study: parallel use of 16S profiling and virome sequencing in stool samples from children with islet autoimmunity and matched controls. Pediatric Diabetes, In press.
Cole, J. R., Wang, Q., Cardenas, E., Fish, J., Chai, B., Farris, R. J., Kuluam-Syed_hoideen, A. S., McGarrell, D. M., Marsh, T., Garrity, G. M. &. Tiedje, J. M. (2009). The Ribosomal Database Project: Improved alignments and new tools for rRNA analysis. Nucleic Acids Research 37, D141-D145.
DeSantis, T. Z., Hugenholtz, P., Larsen, N., Rojas, M., Brodie, E. L., Keller, K., . . . Andersen, G. L. (2006).

Greengenes, a chimera-checked 16S rRNA gene database and workbench compatible with ARB. Applied and Environmental Microbiology, 72(7), 5069-72. http://doi.org/10.1128/AEM.03006-05

Dominguez-Bello M G, De Jesus-Laboy K M, Shen N, Cox L M, Amir A, Gonzalez A, Bokulich N A, Song S J, Hoashi M, Rivera-Vinas J I, Mendez K, Knight R, Clemente J C (2016) Partial restoration of the microbiota of cesarean-born infants via vaginal microbial transfer. Nature Medicine 22: 250-253. doi:10.1038/nm.4039

Edgar R. C., Haas B. J., Clemente J. C., Quince C. & Knight R. (2011) UCHIME improves sensitivity and speed of chimera detection. Bioinformatics 27, 2194-2200.

Fakruddin, M., Mannan, K. S. Bin, Andrews, S., Fakruddin, M., Mannan, K. S. Bin, & Andrews, S. (2013). Viable but nonculturable bacteria: food safety and public health perspective. ISRN Microbiology, 2013, 703813. http://doi.org/10.1155/2013/703813

Fisher, R. A. (1954). Statistical Methods for Research Workers. Oliver and Boyd. ISBN 0-05-002170-2.

Gower, J. C. (1966) Some distance properties of latent root and vector methods used in multivariate analysis Biometrika 53: 325-338.

Huang R, Wang K, Hu J. Effect of Probiotics on Depression: A Systematic Review and Meta-Analysis of Randomized Controlled Trials. Nutrients. 2016 Aug. 6; 8(8). pii: E483. doi: 10.3390/nu8080483.

Hughes J B & Hellmann J J (2005) The application of rarefaction techniques to molecular inventories of microbial diversity. Methods in enzymology, 397: 292-308. DOI: 10.1016/S0076-6879(05)97017-1

Hutkins R W, Krumbeck J A, Bindels L B, Cani P D, Fahey G Jr., Goh Y J, Hamaker B, Martens E C, Mills D A, Rastal R A, Vaughan E, Sanders M E (2016). "Prebiotics: why definitions matter". Curr Opin Biotechnol. 37: 1-7. doi:10.1016/j.copbio.2015.09.001. PMC 4744122free to read. PMID 26431716.

Fumagalli M, Pozzoli U, Cagliani R, Comi G P, Riva S, et al. (2009) Parasites represent a major selective force for interleukin genes and shape the genetic predisposition to autoimmune conditions. The Journal of experimental medicine 206: 1395-1408. doi: 10.1084/jem.20082779 PMID: 19468064

Gibson G R, Roberfroid M B (June 1995). "Dietary modulation of the human colonic microbiota: introducing the concept of prebiotics". J Nutr. 125 (6): 1401-1412. PMID 7782892.

Huse S. M., Welch D. M., Morrison H. G. & Sogin M. L. (2010) Ironing out the wrinkle in the rare bioshphere through improved OTU clustering. Environmental Microbiology 12, 1889-1898.

Koskinen K1, Hultman J, Paulin L, Auvinen P, Kankaanpää H. (2011) Spatially differing bacterial communities in water columns of the northern Baltic Sea. FEMS Microbiol Ecol. 75: 99-110.

Kozich J. J., Westcott S. L., Baxter N. T., Highlander S. K. & Schloss P. D. (2013) Development of dual-index sequencing strategy and curation pipeline for analyzing amplicon sequence data on MiSeq illumina sequencing platform. Applied and Environmental Microbiology 79, 5112-5120.

Krebs, C. (2001) Ecology: the experimental analysis of distribution and abundance. Fifth edition. Benjamin Cummings, San Francisco, Calif., USA. ISBN 0-321-04289-1.

Krogvold, L., Edwin, B., Buanes, T., Frisk, G., Skog, O., Anagandula, M., . . . Dahl-Jørgensen, K. (2015). Detection of a low-grade enteroviral infection in the islets of langerhans of living patients newly diagnosed with type 1 diabetes. Diabetes, 64(5), 1682-7. http://doi.org/10.2337/db14-1370

Legendre P, Legendre L. 1998. Numerical ecology. 2nd English edition. Elsevier Science B V, Amsterdam.

Love, M. I., Huber, W., & Anders, S. (2014). Moderated estimation of fold change and dispersion for RNA-seq data with DESeq2. Genome Biology, 15(12), 550. http://doi.org/10.1186/s13059-014-0550-8

Magurran, A. E., 2004, Measuring biological diversity, Blackwell Publishing: Oxford, U K.

Matisz C E, Leung G, Reyes J L, Wang A, Sharkey K A, McKay D M. Adoptive transfer of helminth antigen-pulsed dendritic cells protects against the development of experimental colitis in mice. Eur J Immunol. 2015 November; 45(11):3126-39.

McFarland L V, Huang Y, Wang L, Malfertheiner P. Systematic review and meta-analysis: Multi-strain probiotics as adjunct therapy for *Helicobacter pylori* eradication and prevention of adverse events. United European Gastroenterol J. 2016 August; 4(4):546-61. doi: 10.1177/2050640615617358.

McMurdie, P. J., & Holmes, S. (2013). phyloseq: an R package for reproducible interactive analysis and graphics of microbiome census data. PloS One, 8(4), e61217. http://doi.org/10.1371/journal.pone.0061217

Muhleisen A L and Herbst-Kralovetz M M. Menopause and the vaginal microbiome. Maturitas. 2016 September; 91:42-50. doi: 10.1016/j.maturitas.2016.05.015.

Öqvist, C. et al. 2008. Prokaryotic microbiota of recycled paper mills with low or zero effluent. J Ind Microbiol Biotechnology. 35: 1165-1173.

Petrof E O, Gloor G B, Vanner S J, Weese S J, Carter D, Daigneault M C, Brown E M, Schroeter K, Allen-Vercoe E 2013. Stool substitute transplant therapy for the eradication of *Clostridium difficile* infection: 'RePOOPulating' the gut. Microbiome 2013 1:3. DOI: 10.1186/2049-2618-1-3

Pruesse, E., Quast, C., Knittel, K., Fuchs, B. M., Ludwig, W., Peplies, J., & Glöckner, F. O. (2007). SILVA a comprehensive online resource for quality checked and aligned ribosomal RNA sequence data compatible with ARB. Nucleic Acids Research, 35(21), 7188-7196. http://doi.org/0.1093/nar/gknn864

Rossi O, van Berkel L A, Chain F, Tanweer Khan M, Taverne N, Sokol H, Duncan S H, Flint H J, Harmsen H J, Langella P, Samsom J N, Wells J M. (2016). *Faecalibacterium prausnitzii* A2-165 has a high capacity to induce IL-10 in human and murine dendritic cells and modulates T cell responses. Sci Rep. January 4; 6:18507. doi: 10.1038/srep18507

Schloss, P. D., Westcott, S. L., Ryabin, T., Hall, J. R., Hartmann, M., Hollister, E. B., . . . Weber, C. F. (2009). Introducing mothur: Open-source, platform-independent, community-supported software for describing and comparing microbial communities. Applied and Environmental Microbiology, 75(23), 7537-7541. http://doi.org/10.1128/AEM.01541-09

Schloss, P. D., Gevers, D. & Westcott, S. L. (2011) Reducing the Effects of PCR Amplification and Sequencing Artifacts on 16S rRNA-Based Studies. PLoS ONE, 6: e27310.

Schloss, P. D. (2014). Microbiology: An integrated view of the skin microbiome. Nature. 514 (7520): 44-45. doi: 10.1038/514044a.

Schmidt T S B, Matias Rodrigues J F, von Mering C (2014) Ecological Consistency of SSU rRNA-Based Operational Taxonomic Units at a Global Scale. PLoS Comput Biol 10(4): e1003594. doi:10.1371/journal.pcbi.1003594

Schnorr et al. 2014. Gut microbiome of the Hadza hunter-gatherers. 5: 3654. DOI: 10.1038/ncomms4654

Shannon, C. E. (1948) A mathematical theory of communication. The Bell System Technical Journal, 27, 379-423 and 623-656.

Schuijs M J, Hartmann S, Selkirk M E, Roberts L B, Openshaw P J, Schnoeller C. The Helminth-Derived Immunomodulator AvCystatin Reduces Virus Enhanced Inflammation by Induction of Regulatory IL-10+ T Cells. PLoS One. 2016 Aug. 25; 11(8):e0161885.

Sokol H, Pigneur B, Watterlot L, Lakhdari O, Bermúdez-Humarán L G, Gratadoux J J, Blugeon S, Bridonneau C, Furet J P, Corthier G, Grangette C, Vasquez N, Pochart P, Trugnan G, Thomas G, Blottière H M, Doré J, Marteau P, Seksik P, Langella P. (2008). *Faecalibacterium prausnitzii* is an anti-inflammatory commensal bacterium identified by gut microbiota analysis of Crohn disease patients. Proc Natl Acad Sci USA. October 28; 105(43): 16731-6. doi: 10.1073/pnas.0804812105

Stein M M, Hrusch C L, Gozdz J, Igartue C, Pivniouk V, Murray S E, Ledford J G, dos Santos M M, Anderson R L, Metwali N, Neilson J W, Maier R M, Gilbert J A, Holbreich M, Thorne P S, Martinez F D, von Mutius E, Vercelli D, Ober C, Sperling Al 2016. Innate immunity and asthma risk in amish and hutterite farm children. New Engl. J. Med. 375: 411-421.

Stewart, E. J. (2012). Growing unculturable bacteria. Journal of Bacteriology, 194(16), 4151-60. http://doi.org/10.1128/JB.00345-12

Sung H, Kim S W, Hong M, Suk K T. Microbiota-based treatments in alcoholic liver disease. World J Gastroenterol. 2016 Aug. 7; 22(29):6673-82.

Taylor L H, Latham S M, Woolhouse M E J (2001) Risk factors for human disease emergence. Phil. Trans. R. Soc. Lond. B 356, 983-989.

Wang Q, Garrity G M, Tiedje J M, Cole J R (2007) Naive Bayesian classifier for rapid assignment of rRNA sequences into the new bacterial taxonomy. Appl Environ Microbial 73: 5261-5267.

Yatsunenko et al. 2012. Human gut microbiome viewed across age and geography. Nature 486, 222-227.

---

The invention claimed is:

1. A topical composition comprising a microbial community of non-culturable bacteria having non-human origin, wherein
   i. the microbial diversity of the immunomodulatory composition is at least 3 at Shannon diversity index;
   ii. the microbial richness of the immunomodulatory composition is at least 130 operational taxonomic units;
   iii. the microbial abundance of the immunomodulatory composition is at least 1,000,000 bacterial 16S copies $g^{-1}$ ww;
   and
the abundance of pathogens in the immunomodulatory composition is below 500 16S gene sequences per 0.25 g sample in bacterial genera *Acinetobacter, Actinomyces, Aerococcus, Aeromonas, Arcobacter, Bacillus, Bacteroides, Bifidobacterium, Brevibacillus, Brevundimonas, Chryseobacterium, Corynebacterium, Fibrobacter, Finegoldia, Gemella, Lactobacillus, Legionella, Leptotrichia, Moraxella, Mycobacterium, Myroides, Neisseria, Nocardia, Paenibacillus, Prevotella, Pseudomonas, Pseudonocardia, Psychrobacter, Rhodococcus, Rickettsia, Saccharomonospora, Sphingomonas, Stenotrophomonas, Streptococcus*, and *Treponema*; wherein the composition is selected from a lotion, cream, gel, powder, conditioner, shampoo, soap, or liquid soap.

2. The topical composition of claim 1, wherein the microbial community comprises viable non-culturable bacteria or components of the viable non-culturable bacteria in the form of inactivated or killed bacteria.

3. The topical composition of claim 1, wherein the spatial variation of the microbial community is homogeneous.

4. The topical composition of claim 1, further comprising material from at least one eukaryote or virus selected from Fungi, bacteriophages, plant viruses, Amoeba, Ecdysozoa including Nematoda, Arachnida, Acari, insects and other multicellular but microscopic soil organisms and unicellular eukaryotes such as Amoebozoa and unicellular fungi.

5. The topical composition of claim 1, wherein the topical composition induces an immunoregulatory IL-10 response in white blood cells.

6. A method for maintaining and strengthening immune system and immunological regulation of a subject, the method comprising exposing the subject to the topical composition according to claim 1, wherein the subject is exposed to the topical composition for at least 2 weeks, and wherein the exposure is carried out sequentially at intervals of not more than 7 days.

7. The method according to claim 6, wherein the exposure is carried out daily.

8. The method according to claim 6, wherein exposing comprises bringing an area on the skin of the subject in contact with the topical composition for at least 1 second.

9. A method for treating allergy comprising exposing the subject to the topical composition of claim 1, wherein the immunomodulatory composition is mediated by IL-10.

10. The method according to claim 6, wherein
   a. the subject has a decreased microbial diversity, richness and/or abundance compared to a reference subject;
   b. exposing is carried out at least until the microbial diversity, richness and/or abundance returns towards a level corresponding to the level of a reference subject or closer to the level of the reference subject; and c. the reference subject is a subject having a microbial diversity, richness and/or abundance corresponding to a level observed for subjects living in a non-urban environment.

11. The method according to claim 6, wherein the subject is a human subject having a disorder of immunity or a human subject living in an urban environment wherein microbial diversity, richness and/or abundance is lower than in the material derived from nature.

12. A method for treating allergy comprising exposing the subject to the topical composition of claim 1, wherein the effect of the immunomodulatory composition is mediated by TGF-$\beta$.

13. The topical composition of claim 1, wherein the topical composition induces a TGF-beta mediated immunomodulatory effect.

\* \* \* \* \*

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: oligont

<400> SEQUENCE: 1
aaactcaaag gaattgacgg                                                   20

<210> SEQ ID NO 2
<211> LENGTH: 20
<212> TYPE: DNA
<213> ORGANISM: Artificial Sequence
<220> FEATURE:
<223> OTHER INFORMATION: oligont

<400> SEQUENCE: 2
acgagctgac gacagccatg                                                   20

<210> SEQ ID NO 3
<211> LENGTH: 19
<212> TYPE: DNA
<213> ORGANISM: Artificial Sequence
<220> FEATURE:
<223> OTHER INFORMATION: oligont

<400> SEQUENCE: 3
gtgccagcmg ccgcggtaa                                                    19

<210> SEQ ID NO 4
<211> LENGTH: 20
<212> TYPE: DNA
<213> ORGANISM: Artificial Sequence
<220> FEATURE:
<223> OTHER INFORMATION: oligont

<400> SEQUENCE: 4
ggactachvg ggtwtctaat                                                   20
```

```
<210> SEQ ID NO 5
<211> LENGTH: 57
<212> TYPE: DNA
<213> ORGANISM: Artificial sequence
<220> FEATURE:
<223> OTHER INFORMATION: oligont

<400> SEQUENCE: 5
atctacactc tttccctaca cgacgctctt ccgatctaga gtttgatcmt ggctcag      57

<210> SEQ ID NO 6
<211> LENGTH: 52
<212> TYPE: DNA
<213> ORGANISM: Artificial sequence
<220> FEATURE:
<223> OTHER INFORMATION: oligont

<400> SEQUENCE: 6
gtgactggag ttcagacgtg tgctcttccg atctgtatta ccgcggctgc tg           52

<210> SEQ ID NO 7
<211> LENGTH: 20
<212> TYPE: DNA
<213> ORGANISM: Artificial sequence
<220> FEATURE:
<223> OTHER INFORMATION: oligont

<400> SEQUENCE: 7
agagtttgat cmtggctcag                                                20

<210> SEQ ID NO 8
<211> LENGTH: 23
<212> TYPE: DNA
<213> ORGANISM: Artificial sequence
<220> FEATURE:
<223> OTHER INFORMATION: oligont

<400> SEQUENCE: 8
tagagagttt gatcmtggct cag                                            23

<210> SEQ ID NO 9
<211> LENGTH: 24
<212> TYPE: DNA
<213> ORGANISM: Artificial sequence
<220> FEATURE:
<223> OTHER INFORMATION: oligont

<400> SEQUENCE: 9
ctctagagtt tgatcmtggc tcag                                           24

<210> SEQ ID NO 10
<211> LENGTH: 18
<212> TYPE: DNA
<213> ORGANISM: Artificial sequence
<220> FEATURE:
<223> OTHER INFORMATION: oligont

<400> SEQUENCE: 10
gtattaccgc ggctgctg                                                  18

<210> SEQ ID NO 11
<211> LENGTH: 19
<212> TYPE: DNA
<213> ORGANISM: Artificial sequence
<220> FEATURE:
<223> OTHER INFORMATION: oligont
```

```
<400> SEQUENCE: 11
cgtattaccg cggctgctg                                                19

<210> SEQ ID NO 12
<211> LENGTH: 20
<212> TYPE: DNA
<213> ORGANISM: Artificial sequence
<220> FEATURE:
<223> OTHER INFORMATION: oligont

<400> SEQUENCE: 12
tagtattacc gcggctgctg                                               20

<210> SEQ ID NO 13
<211> LENGTH: 37
<212> TYPE: DNA
<213> ORGANISM: Artificial sequence
<220> FEATURE:
<223> OTHER INFORMATION: oligont

<400> SEQUENCE: 13
atctacactc tttccctaca cgacgctctt ccgatct                            37

<210> SEQ ID NO 14
<211> LENGTH: 34
<212> TYPE: DNA
<213> ORGANISM: Artificial sequence
<220> FEATURE:
<223> OTHER INFORMATION: oligont

<400> SEQUENCE: 14
gtgactggag ttcagacgtg tgctcttccg atct                               34
```